United States Patent [19]
Dawson et al.

[11] Patent Number: 5,434,073
[45] Date of Patent: Jul. 18, 1995

[54] FIBRINOLYTIC AND ANTI-THROMBOTIC CLEAVABLE DIMERS

[75] Inventors: Keith Dawson, Marlow; Michael G. Hunter, Aylesbury; Lloyd G. Czaplewski, Didcot, all of United Kingdom

[73] Assignee: British Bio-Technology Limited, Oxford, England

[21] Appl. No.: 854,596

[22] PCT Filed: Dec. 7, 1990

[86] PCT No.: PCT/GB90/01911

§ 371 Date: Jun. 3, 1992

§ 102(e) Date: Jun. 3, 1992

[87] PCT Pub. No.: WO91/09125

PCT Pub. Date: Jun. 27, 1991

[30] Foreign Application Priority Data

Dec. 7, 1989 [GB] United Kingdom ............... 8927722

[51] Int. Cl.$^6$ .................. C12N 9/70; C07K 13/00
[52] U.S. Cl. ............................ 435/216; 530/350; 530/402; 435/69.7; 424/94.64
[58] Field of Search .............. 435/69.7, 216; 530/402, 530/350; 424/94.64

[56] References Cited

U.S. PATENT DOCUMENTS

| | | | |
|---|---|---|---|
| 4,752,581 | 6/1988 | Robinson et al. | 435/212 |
| 4,880,776 | 11/1989 | Robinson et al. | 435/215 |
| 4,944,943 | 7/1990 | Eschenfelder et al. | 424/94.64 |
| 4,992,274 | 2/1991 | Robinson et al. | 435/215 |
| 5,087,564 | 2/1992 | Mai et al. | 435/69.7 |
| 5,126,134 | 6/1992 | Heim et al. | 424/94.64 |
| 5,164,304 | 11/1992 | Johnson et al. | 435/69.1 |
| 5,200,340 | 4/1993 | Foster et al. | 435/212 |

FOREIGN PATENT DOCUMENTS 0323149 7/1989 European Pat. Off.
2160206 12/1985 United Kingdom.

OTHER PUBLICATIONS

Marder & Sherry, New Eeng. J. Med. 318:1512–1520 (1988).
Bloom, AL, Brit. J. Haemotol. 82:129 (1962).
Francis et al., J. Lab Clin. Med. 102:220 (1983).
Mirshahi et al., Blood 74:1025 (1989).
Mann et al., Meth. Enzy. 80:286–301 (1981).
Eaton et al., Biochem. 25:505–512 (1986).
Ni et al., Biochem. 28:3082–3094 (1989).
Chang et al., Eur. J. Biochem. 151:217–224 (1985).
Dodt et al., FEBS Lett. 165:180 (1984).
Malke, Rose, Ferretti, Gene 34:357–362 (1985).
Mann in "Progress in Hemostasis & Thrombosis" pp. 1–24 (ed. Spaet, TH. Grune & Stratton) 1984.
Magnusson et al., in "Proteases and Biological Control" pp. 123–149 (ed. Reich et al., Cold Spring Harbor Labs, N.Y.) 1975.
Takahashi et al "Primary structure of blood coagulation factor XIII a ... " *PNAS* 83:8019–8023 (Nov. 1986).
Lijnen et al, *Thrombosis Research* 57:333–342, Feb. 1, 1990.
Klessen et al, *Mol. Gen. Genet.* 212:295–300, 1988.
Fortkamp et al, *DNA* 5:511–517, 1986.

*Primary Examiner*—Stephen G. Walsh
*Attorney, Agent, or Firm*—Allegretti & Witcoff, Ltd.

[57] ABSTRACT

Relatively inactive fusion proteins are activatable by enzymes of the clotting cascade to have fibrinolytic and/or clot formation inhibition activity. For example, a fusion protein comprising two hirudin or streptokinase molecules, linked by a cleavable linkage sequence, may be cleaved to yield anti-thrombotic hirudin or fibrinolytic streptokinase by thrombin or Factor Xa. Fibrinolytic or clot formation inhibition activity is therefore directed to the site of clot formation. Cleavable streptokinase/hirudin heterodimers are claimed.

1 Claim, 7 Drawing Sheets

FIG. 1

```
AGCTT- - - - - -BB2011- - - - - -P          P- - - - - -BB2013- - - - - -P          P- - - - - -BB2015- - - - - -P
    A- - - - - -BB2012- - - - - -P                     BB2014- - - - - -P                     BB2016- - - - - -P

P- - - - - -BB2017- - - - - -P          P- - - - - -BB2019- - - - - -P          P- - - - - -BB2021- - - - - -G
           BB2018- - - - - -P                     BB2020- - - - - -P                     BB2022- - - - - -CTTAA
```

FIG. 7

FIBRINOLYTIC AND ANTI-THROMBOTIC CLEAVABLE DIMERS

This application is the US national stage under 37 CFR 371 of PCT/GB90/01911, filed 7 Dec. 1990.

This invention relates to proteinaceous compounds which can be cleaved to release fibrinolytic and/or anti-thrombotic activity. It also relates to nucleic acid (DNA and RNA) coding for all or part of such compounds. In preferred embodiments, the invention relates to fusion proteins produced by linking together fibrinolytic and/or anti-thrombotic proteins with a cleavable linker, their preparation, pharmaceutical compositions containing them and their use in the treatment of thrombotic disease.

The fibrinolytic system is the natural counterpart to the clotting system in the blood. In the process of blood coagulation, a cascade of enzyme activities are involved in generating a fibrin network which forms the framework of a clot, or thrombus. Degradation of the fibrin network (fibrinolysis) is accomplished by the action of the enzyme plasmin. Plasminogen is the inactive precursor of plasmin and conversion of plasminogen to plasmin is accomplished by cleavage of the peptide bond between arginine 561 and valine 562 of plasminogen. Under physiological conditions this cleavage is catalysed by tissue-type plasminogen activator (tPA) or by urokinase-type plasminogen activator (uPA).

If the balance between the clotting and fibrinolytic systems becomes locally disturbed, intravascular clots may form at inappropriate locations leading to conditions such as coronary thrombosis and myocardial infarction, deep vein thrombosis, stroke, peripheral arterial occlusion and embolism. In such cases, the administration of fibrinolytic and anti-thrombotic agents has been shown to be a beneficial therapy for the promotion of clot dissolution.

Fibrinolytic therapy has become relatively widespread with the availability of a number of plasminogen activators such as tPA, uPA, streptokinase and the anisoylated plasminogen streptokinase activator complex, APSAC. Each of these agents has been shown to promote clot lysis, but all have deficiencies in their activity profile which makes them less than ideal as therapeutic agents for the treatment of thrombosis (reviewed by Marder and Sherry, *New England Journal of Medicine* 1989, 318: 1513-1520).

A major problem shared by all of these agents is that at clinically useful doses, they are not thrombus specific as they activate plasminogen in the general circulation. The principal consequence of this is that proteins such as fibrinogen involved in blood clotting are destroyed and dangerous bleeding can occur. This also occurs with tPA despite the fact that, at physiological concentrations, it binds to fibrin and shows fibrin selective plasminogen activation.

Another important shortcoming in the performance of existing plasminogen activators is that re-occlusion of the reperfused blood vessel commonly occurs after cessation of administration of the thrombolytic agent. This is thought to be due to the persistence of thrombogenic material at the site of thrombus dissolution. Anti-thrombotic proteins may be used in the treatment or prophylaxis of thrombosis either alone or as an adjunct to fibrinolytic agents. Suitable anti-thrombotic proteins include hirudin, activated protein C and anti-thrombin III.

An alternative approach to enhancing fibrinolysis and inhibition of blood clotting has now been devised which is based on the use of fusion proteins cleavable to achieve release of fibrinolytic and/or anti-thrombotic activity at the site of blood clotting. To achieve this, proteins involved in fibrinolysis or inhibition of coagulation are joined by a linker region which is cleavable by an enzyme involved in blood clotting. Examples of proteins which may be incorporated into such a cleavable protein include tPA, uPA, streptokinase, plasminogen, activated protein C, hirudin and anti-thrombin III. Fusion of such proteins to a protein with a favourable property not directly related to dissolution of blood clots, for example albumin which has a long plasma half-life, may also be beneficial. An advantage of this approach is that thrombus selectivity of fibrinolytic or inhibition of clot formation activity is achieved by way of the thrombus-specific localisation of the cleaving enzymes.

According to a first aspect of the invention, there is provided a fusion protein comprising a first sequence and a second sequence, the fusion protein being cleavable between the first and second sequences by an enzyme involved in blood clotting, wherein after the fusion protein is so cleaved the first and second sequences, or either of them, has greater fibrinolytic and/or anti-thrombotic activity than the uncleaved fusion protein.

The fusion protein may be a cleavable dimer of two fibrinolytic and/or anti-thrombotic proteins, such as hirudin or streptokinase. It may be a homodimer or a heterodimer. The fusion protein may have substantially reduced or no fibrinolytic and/or anti-thrombotic activity compared to the cleavage products, but a certain amount of activity in the fusion protein can be tolerated. It is not necessary for both the cleavage products to have fibrinolytic and/or anti-thrombotic activity, but it is preferred for them to do so.

The fusion protein is not restricted to being a dimer; it may have any number (such as three, four or more) sequences which are cleavable one from the other, compatible with the therapeutic utility of the protein. At least one, and preferably more than one or even all, of the sequences resulting from the cleavage will have greater activity than the fusion protein, or a combination of some or all of the cleavage products will collectively have such greater activity. In any event, cleavage will result in a net increase in or release of activity.

Proteinaceous compounds in accordance with the first aspect of the invention, are therefore cleaved to release activity in at least one of two ways. First, a compound may be cleaved to release fibrinolytic activity. Secondly, a compound may be cleaved to release anti-thrombotic activity. Conceivably, a compound may be cleaved to release both functions. It should be noted that a released fragment of the fusion protein may have fibrinolytic activity directly (in that it lyses fibrin) or indirectly (in that it causes activation of a molecule which leads to lysis of fibrin).

One preferred proteinaceous compound which is cleavable to have enhanced anti-thrombotic activity is a fusion protein of two hirudin molecules linked (for example carboxy terminus to amino terminus) by a linker amino acid sequence cleavable, for example, by Factor Xa.

Hirudins are naturally occurring polypeptides of 65 or 66 amino acids in length that are produced by the leech *Hirudo medicinalis*. Hirudin is an anticoagulating agent which binds to thrombin and prevents blood coagulation by inhibiting thrombin from catalysing the conversion of fibrinogen to fibrin, thus preventing the formation of the protein framework of blood clots. The binding of hirudin also prevents other prothrombic activities of thrombin, including activation of factors V, VII, XIII and platelets. There are three principal variants of hirudin (named HV-1, HV-2 and HV-3).

Another preferred fusion protein comprises two streptokinase molecules linked (for example carboxy terminus to amino terminus) by a linker amino acid sequence cleavable, for example, by thrombin.

Streptokinase is a 414 amino acid, 47 kDa protein secreted by many pathogenic streptococci of different serogroups. It is a plasminogen activator but, unlike mammalian plasminogen activators, it is not a protease and it activates plasminogen by forming a binary complex with plasminogen (SK-plasminogen) which functions as an activator of free plasminogen. Streptokinase is effective in inducing clot lysis in the treatment of myocardial infarction and is widely used for this indication.

Cleavable fusion proteins within the scope of this invention may have reduced fibrinolytic and/or anti-thrombotic activity compared to their component molecules; cleavage releases the component molecules which possess to an adequate degree the activity of their wild-type parent molecules.

The blood coagulation mechanism comprises a series of enzyme reactions which culminate in the production of insoluble fibrin, which forms the mesh-like protein framework of blood clots. Thrombin is the enzyme responsible for the conversion of soluble fibrinogen to fibrin. Conversion of prothrombin, the inactive precursor of thrombin, to thrombin is catalysed by activated Factor X (Factor Xa). (Thrombin is also known as Factor IIa, and prothrombin as Factor II.)

Factor Xa is generated from Factor X extrinsically or intrinsically. In the extrinsic route, Factor VII is activated to Factor VIIa, which generates Factor Xa from Factor X. In the intrinsic route, the activation of Factor X to Factor Xa is catalysed by Factor IXa. Factor IXa is generated from Factor IX by the action of Factor XIa, which in turn is generated by the action of Factor XIIa on Factor XI. Factor XIIa is generated from Factor XII by the action of Kallikrein. Factors VIIIa and Va are thought to act as cofactors in the activation of Factors X and II, respectively.

Fibrin, as first formed from fibrinogen, is in the loose form. Loose fibrin is converted to tight fibrin by the action of Factor XIIIa, which crosslinks fibrin molecules.

Activated protein C is an anticoagulant serine protease generated in the area of clot formation by the action of thrombin, in combination with thrombomodulin, on protein C. Activated protein C regulates clot formation by cleaving and inactivating the pro-coagulant cofactors Va and VIIIa.

The term "enzyme involved in blood clotting" as used in this specification therefore includes kallikrein Factors XIIa, XIa, IXa, VIIa, Xa and thrombin (Factor IIa), which are directly involved in the formation of fibrin and activated protein C, which is involved in the control of blood clotting. The most preferred enzymes are Factor Xa and thrombin because they are most immediately involved with fibrin formation.

Generation and activity of at least Factor Xa and thrombin is tightly regulated to ensure that thrombus generation is restricted to the site of the thrombogenic stimulus. This localisation is achieved by the combined operation of at least two control mechanisms: the blood clotting enzymes function as complexes intimately associated with the phospholipid cellular membranes of platelets and endothelial cells at the site of vascular injury (Mann, K. G., 1984, in:

"Progress in Hemostasis and Thrombosis", 1–24, ed Spaet, T. H. Grune and Stratton); and, free thrombin or Factor Xa released from the thrombus site into the circulation is rapidly inactivated by the action of proteinase inhibitors such as anti-thrombin III.

Thus, the activity of the penultimate (Factor Xa) and the final (thrombin) enzymes in the clotting cascade are particularly well localised to the site of thrombus generation and for this reason are preferred. Thrombin has been found to remain associated with thrombi and to bind non-covalently to fibrin. On digestion of thrombi with plasmin, active thrombin is liberated and is thought to contribute to the reformation of thrombi and the re-occlusion of vessels which commonly occurs following thrombolytic treatment with plasminogen activators (Bloom A. L., 1962, *Br. J. Haematol,* 82 129; Francis et al, 1983, *J. Lab. Clin. Med.,* 102, 220; Mirshahi et al, 1989, Blood 74, 1025).

For these reasons, it is preferred in certain embodiments of the invention to produce fusion proteins activatable by thrombin or Factor Xa thereby to create a preferred class of thrombus-selective, fibrinolytic proteins. The most preferred of these fusion proteins regains the favourable properties of the parent molecules upon cleavage and exhibit thrombus selectivity by the novel property of being cleaved to release the component proteins of the fusion protein at the site of new thrombus formation by the action of one of the enzymes involved in generation of the thrombus and preferably localised there. Factor Xa (E.C.3.4.21.6) is a serine protease which converts human prothrombin to thrombin by specific cleavage of the Arg(273)-Thr(274) and Arg(322)-Ile(323) peptide bonds (Mann et al 1981, *Methods in Enzymology* 80 286–302). In human prothrombin, the Arg(273)-Thr(274) site is preceded by the tripeptide Ile-Glu-Gly and the Arg(322)-Ile(323) site is preceded by the tripeptide Ile-Asp-Gly. The structure required for recognition by Factor Xa appears to be determined by the local amino acid sequence preceding the cleavage site (Magnusson et al, 1975, in: "Proteases and Biological Control", 123–149 eds., Reich et al, Cold Spring Harbor Laboratory, New York). Specificity for the Ile-Glu-Gly-Arg and Ile-Asp-Gly-Arg sequence is not absolute as Factor Xa has been found to cleave other proteins, for example Factor VIII at positions 336, 372, 1689 and 1721, where the preceding amino acid sequence differs significantly from this format (Eaton et al, 1986 *Biochemistry* 25 505–512). As the principal natural substrate for Factor Xa is prothrombin, preferred recognition sequences are those in which arginine and glycine occupy the P1 and P2 positions, respectively, an acidic residue (aspartic or glutamic acid) occupies the P3 position and isoleucine or another small hydrophobic residue (such as alanine, valine, leucine or methionine) occupies the P4 position. However, as Factor Xa can cleave sequences which differ from this format, other sequences cleavable by Factor Xa may be used in the invention, as can other sequences cleavable by other enzymes of the clotting cascade.

In order to make fusion proteins which are cleavable by these preferred enzymes, the amino acid sequence linking the components of the fusion protein must be recognised as a cleavage site for these preferred enzymes. To make fusion proteins which are cleaved by, for example, Factor Xa, an amino acid sequence cleavable by Factor Xa may be used to link the two components (that is, the first and second, and possibly other, sequences) of the fusion protein. The sequence Ile-Glu-Gly-Arg SEQ ID NO: 71, which is at one of the sites in prothrombin cleaved by Factor Xa, may be such a sequence. Other possibilities would be sequences or mimics of sequences cleaved by Factor Xa in other proteins or peptides. DNA coding for the Ile-Glu-Gly-Arg SEQ ID NO: 71 sequence as the carboxy-terminal part of a cleavable linker as a protein production aid is disclosed in UK Patent Application GB-A-2160206 but the use of an Ile-Glu-Gly-Arg SEQ ID NO: 71 sequence for the purpose of this invention is not disclosed in that specification.

Cleavage of fusion proteins by an enzyme of the clotting cascade such as thrombin or Factor Xa can be measured in a number of ways, for example by SDS-PAGE analysis, and by assaying for the functions of one or more of the cleavage products of the fusion protein.

Thrombin (E.C. 3.4.21.5) is a serine protease which catalyses the proteolysis of a number of proteins including fibrinogen (A alpha and B beta chains), Factor XIII, Factor V, Factor VII, Factor VIII, protein C and anti-thrombin III. The structure required for recognition by thrombin appears to be partially determined by the local amino acid sequence around the cleavage site but is also determined to a variable extent by sequence(s) remote from the cleavage site. For example, in the fibrinogen A alpha chain, residues P2 (Val), P9 (Phe) -and P10 (Asp) are crucial for α-thrombin-catalysed cleavage at the Arg(16)-Gly(17) peptide bond (Ni, F. et al 1989, *Biochemistry* 28 3082-3094). Comparative studies of several proteins and peptides which are cleaved by thrombin has led to the proposal that optimum cleavage sites for α-thrombin may have the structure of (i) P4-P3-Pro-Arg-P1'-P2' SEQ ID NO: 72, where each of P3 and P4 is independently a hydrophobic amino acid (such as valine) and each of P1' and P2' is independently a non-acidic amino acids, or (ii) P2-Arg-P1' where P2 or P1' is glycine (Chang, J. 1985, *Eur. J. Biochem.* 151 217-224). There are, however, exceptions to these general structures which are cleaved by thrombin and which may be used in the invention.

To produce a fusion protein which could be cleaved by thrombin, a linker sequence containing a site recognised and cleaved by thrombin may be used. An amino acid sequence such as that cleaved by thrombin in the fibrinogen A alpha chain may be used. Other possible sequences would include those involved in the cleavage by thrombin of fibrinogen B beta, Factor XIII, Factor V, Factor VII, Factor VIII, protein C, anti-thrombin III and other proteins whose cleavage is catalysed by thrombin. An example of a thrombin cleavable linker may be the sequence Gly-Pro-Arg which is identical to that found at positions 17-20 in fibrinogen A alpha. This is not the principal thrombin cleavage site in fibrinogen A alpha but thrombin can cleave the Arg(19)-Val(20) peptide bond. Another suitable thrombin cleavable linker sequence is Val-Glu-Leu-Gln-Gly-Val-Val-Pro-Arg which is identical to that found in Factor XIII.

In a preferred embodiment the invention relates to fusion proteins of streptokinase and/or hirudin linked by peptide sequences which are cleaved by thrombin, Factor Xa or other enzymes involved in blood clotting to release products with fibrinolytic and/or anti-thrombotic activity.

Fusion proteins in accordance with the invention may contain other modifications (as compared to wild-type counterparts of their components such as streptokinase and hirudin) which may be one or more additions, deletions or substitutions. An example of such a modification would be streptokinase variants in which inappropriate glycosylation during yeast expression was prevented by substitution of sequences recognised as glycosylation signals by yeast. Another example would be the addition of an Arg-Gly-Asp-Xaa sequence, where Xaa represents a variable amino acid such as Ser, to the carboxy terminus of the fusion to enhance its plasma lifetime.

Preferred features of fusion proteins within the scope of the invention also apply, where appropriate, to other compounds of the invention, *mutatis mutandis.*

Fusion proteins in accordance with the first aspect of the invention can be synthesised by any convenient route. According to a second aspect of the invention there is provided a process for the preparation of a proteinaceous compound as described above, the process comprising coupling successive amino acid residues together and/or ligating oligopeptides. Although proteins may in principle be synthesised wholly or partly by chemical means, the route of choice will be ribosomal translation, preferably in vivo, of a corresponding nucleic acid sequence. The protein may be glycosylated appropriately.

It is preferred to produce proteins in accordance with the invention by using recombinant DNA technology. DNA encoding each of the first and second sequences of the fusion protein may be from a cDNA or genomic clone or may be synthesised. Amino acid substitutions, additions or deletions are preferably introduced by site-specific mutagenesis. Suitable DNA sequences encoding streptokinase and hirudin and other polypeptide sequences useful in the scope of the invention may be obtained by procedures familiar to those having ordinary skill in genetic engineering. For several proteins, it is a routine procedure to obtain recombinant protein by inserting the coding sequence into an expression vector and transfecting or transforming the vector into a suitable host cell. A suitable host may be a bacterium such as *E. coli,* a eukaryotic microorganism such as yeast or a higher eukaryotic cell.

According to a third aspect of the invention, there is provided synthetic or recombinant nucleic acid coding for a proteinaceous compound as described above. The nucleic acid may be RNA or DNA. Preferred characteristics of this aspect of the invention are as for the first aspect.

According to a fourth aspect of the invention, there is provided a process for the preparation of nucleic acid in accordance with the third aspect, the process comprising coupling successive nucleotides together and/or ligating oligo- and/or polynucleotides.

Recombinant nucleic acid in accordance with the third aspect of the invention may be in the form of a vector, which may for example be a plasmid, cosmid or phage. The vector may be adapted to transfect or transform prokaryotic (for example bacterial) cells and/or eukaryotic (for example yeast or mammalian) cells. A vector will comprise a cloning site and usually at least one marker gene. An expression vector will have a promoter operatively linked to the sequence to be inserted into the cloning site and, preferably, a sequence enabling the protein product to be secreted. Expression vectors and cloning vectors (which need not be capable of expression) are included in the scope of the invention.

It is to be understood that the term "vector" is used in this specification in a functional sense and is not to be construed as necessarily being limited to a single nucleic acid molecule.

Using a vector, for example as described above, fusion proteins in accordance with the invention may be expressed and secreted into the cell culture medium in a biologically active form without the need for any additional biological or chemical procedures. Suitable cells or cell lines to be transformed may be mammalian cells which grow in continuous culture and which can be transfected or otherwise transformed by standard techniques. Examples of suitable cells include Chinese hamster ovary (CHO) cells, mouse myeloma cell lines such as P3X63-Ag8.653, COS cells, HeLa cells, BHK cells, melanoma cell lines such as the Bowes cell line, mouse L cells, human hepatoma cell lines such as Hep G2, mouse fibroblasts and mouse NIH 3T3 cells. Such cells may be particularly appropriate for expression when one or more of the protein sequences constituting the fusion protein is of mammalian derivation, such as tissue plasminogen activator (t-PA).

Yeast (for example *Pichia pastoris* or *Saccharomyces cerevisiae*) or bacteria (for example *Escherichia coli*) may be preferred for the expression of many of the fusion proteins of the invention, as may insect cells such as those which are Baculovirus-infected.

Compounds of the present invention may be used within pharmaceutical compositions for the prevention or treatment of thrombosis or other conditions where it is desired to produce local fibrinolytic and/or anticoagulant activity. Such conditions include myocardial and cerebral infarction, arterial and venous thrombosis, thromboembolism, post-surgical adhesions, thrombophlebitis and diabetic vasculopathies.

According to a fifth aspect of the invention, there is provided a pharmaceutical composition comprising one or more compounds in accordance with the first aspect of the invention and a pharmaceutically or veterinarily acceptable carrier. Such a composition may be adapted for intravenous administration and may thus be sterile. Examples of compositions in accordance with the invention include preparations of sterile fusion proteins in isotonic physiological saline and/or buffer. The composition may include a local anaesthetic to alleviate the pain of injection. Compounds of the invention may be supplied in unit dosage form, for example as a dry powder or water-free concentrate in a hermetically sealed container such as an ampoule or sachet indicating the quantity of protein. Where a compound is to be administered by infusion, it may be dispensed by means of an infusion bottle containing sterile water for injections or saline or a suitable buffer. Where it is to be administered by injections, it may be dispensed with an ampoule of water for injection, saline or a suitable buffer. The infusible or injectable composition may be made up by mixing the ingredients prior to administration. Where it is to be administered as a topical treatment, it may be dispensed in a suitable base.

The quantity of material to be administered will depend on the amount of fibrinolysis or inhibition of clotting required, the required speed of action, the seriousness of the thromboembolic position and the size of the clot. The precise dose to be administered will, because of the very nature of the condition which compounds of the invention are intended to treat, be determined by the physician. As a guideline, however, a patient being treated for a mature thrombus will generally receive a daily dose of a fusion protein of from 0.01 to 10 mg/kg of body weight either by injection in for example up to 5 doses or by infusion.

The invention may be used in a method for the treatment or prophylaxis of thrombosis, comprising the administration of an effective non-toxic amount of a compound in accordance with the first aspect. According to a further aspect of the invention, there is therefore provided the use of a compound as described above in the preparation of a thrombolytic and/or anticoagulant agent.

The invention concerns especially the DNAs, the vectors, the transformed host strains, the fusion proteins and the process for the preparation thereof as described in the examples.

The following examples of the invention are offered by way of illustration, and not by way of limitation. The examples refer to the accompanying drawings.

BRIEF DESCRIPTION OF THE DRAWINGS

FIG. 1 shows schematically the arrangement of a set of oligonucleotides used in the assembly of a synthetic hirudin gene (Preparation 1);

FIG. 7 shows complete nucleotide sequences corresponding to the schematic arrangement depicted in FIG. 1.

METHODOLOGY

Figure 2:
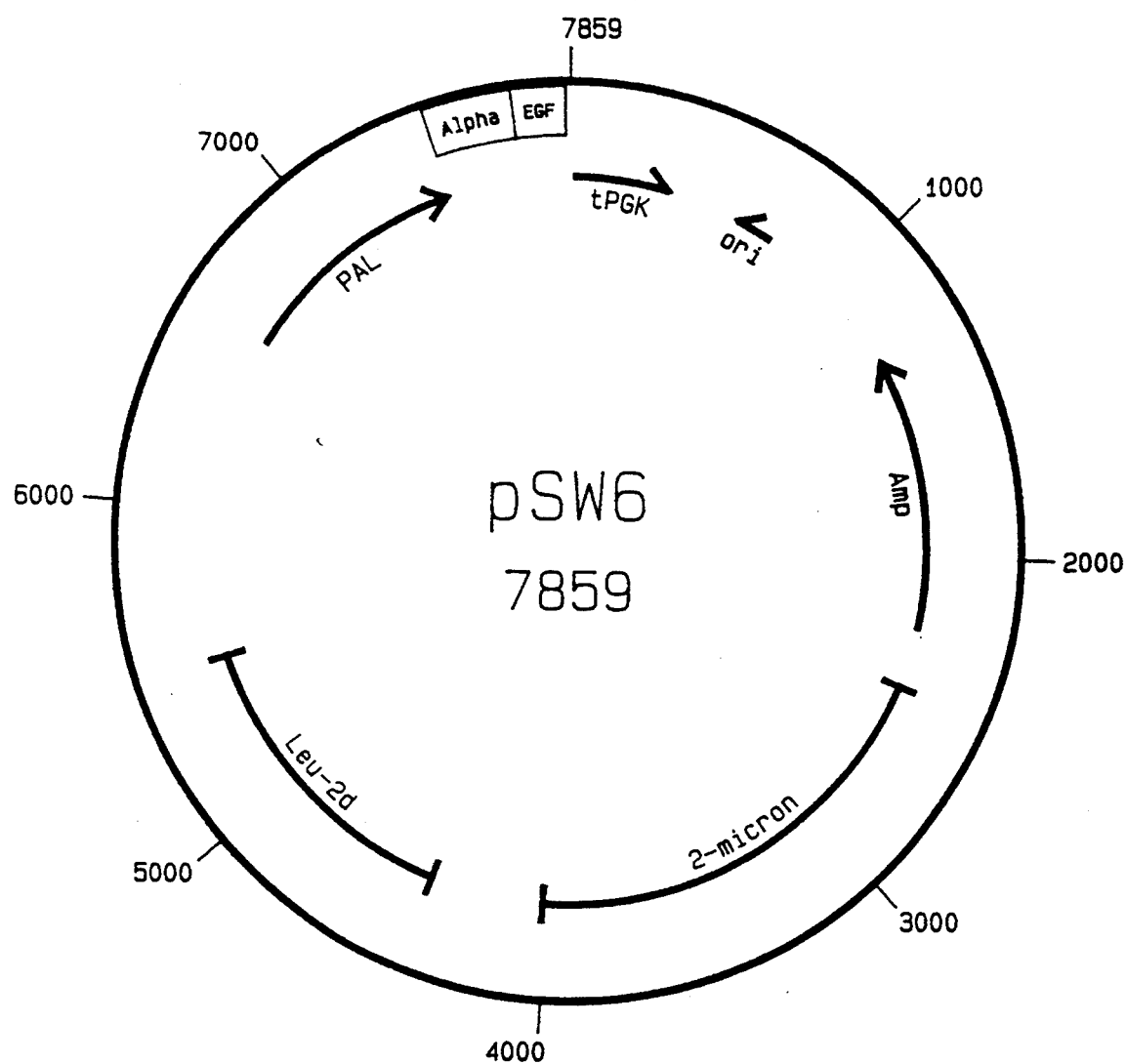
FIG. 2 shows a map of plasmid pSW6 (Preparation 2)

The techniques of genetic engineering and genetic manipulation used in the manufacture of the genes described and in their further manipulation for construction of expression vectors are well known to those skilled in the art. Descriptions of modern techniques can be found in the laboratory manuals "Current Protocols in Molecular Biology", Volumes 7 and 2, edited by F. M. Ausubel et al, published by Wiley-Interscience, New York and in "Molecular Cloning, A Laboratory Manual" (second edition) edited by Sambrook, Fritsch and Maniatis published by Cold Spring Harbor Laboratories, New York. M13mp18, M13mp19 and pUC19 DNAs were purchased from Pharmacia Ltd., Midsummer Boulevard, Central Milton Keynes, Bucks, MK9 3HP, United Kingdom. Restriction endonucleases were purchased either from Northumbria Biologicals Limited, South Nelson Industrial Estate, Cramlington, Northumberland, NE23 9HL, United Kingdom or from New England Biolabs, 32 Tozer Road, Beverly, Mass. 01915-5510 USA. *E. coli* HW1110 (lacIq) is used as expression host in certain of the following examples: a suitable commercially available alternative is JM109, available from Northumbria Biologicals Ltd.

PREPARATION 1

Construction of a Hirudin HV1 Gene

A. Gene Design

A synthetic hirudin HV-1 gene was designed based on the published amino acid sequence (Dodt J., et al *FEBS Letters* 65 180 (1984)). Unique restriction endonuclease target sites were incorporated to facilitate subsequent genetic manipulation (see SEQ. ID NO:1 and 2 in the Sequence Listings immediately before the claims). The codons selected were those favoured by either *S. cerevisiae* or *E. coli* and are thus suitable for expression in either organism.

B. Gene Construction

The gene sequence was divided into 12 oligodeoxyribonucleotides (see SEQ. ID NOS: 50 through 61) such that after annealing each complementary pair 2 oligonucleotides, they were left with cohesive ends either for or of 7 bases in length.

C. Oligonucleotide Synthesis

The oligonucleotides were synthesised by automated phosphoramidite chemistry on an Applied Bio-Systems 380B DNA Synthesiser, using cyanoethyl phosphoramidites. The methodology is now widely used and has already been described (Beaucage, S. L. and Caruthers, M. H. *Tetrahedron Letters* 24, 245 (1981) and Caruthers, M. H. *Science* 230, 281–285 (1985)).

D. Gene Assembly

Figure 7:
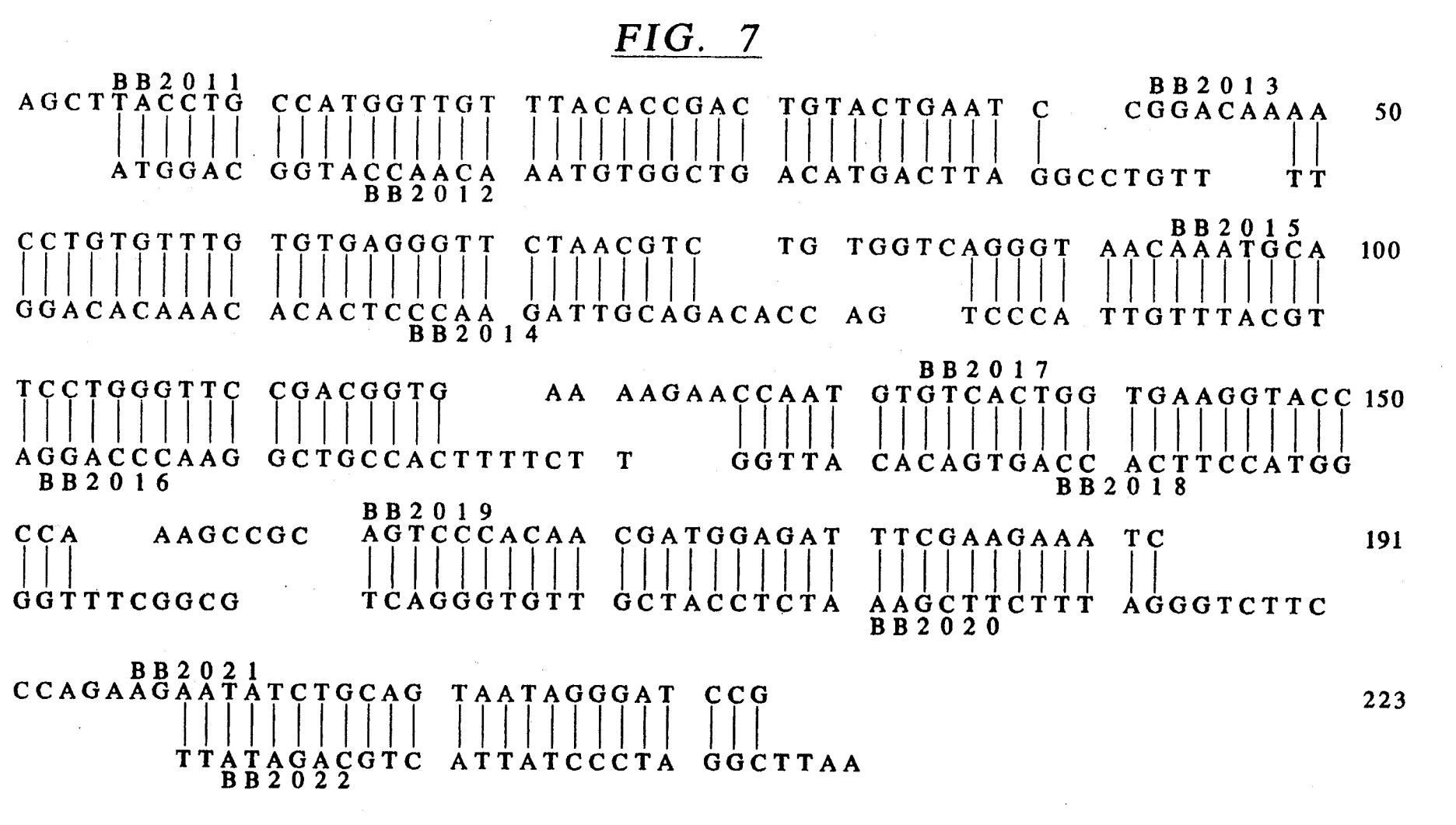

The oligonucleotides were kinased to provide them with a 5′ phosphate to allow their subsequent ligation. The oligonucleotides were assembled as shown in FIGS. 1 and 7.

Kinasing of Oligomers 100 pmole of oligomer was dried down and resuspended in 20 μl kinase buffer (70 mM Tris, pH 7.6, 10 mM MgCl₂, 1 mM ATP, 0.2 mM spermidine, 0.5 mM dithiothreitol (DTT)). T4 polynucleotide kinase (2 mcl. 10 000 U/ml) was added and the mixture was incubated at 37° C. for 30 minutes. The kinase was then inactivated by heating at 70° C for 10 minutes.

Complementary pairs of kinased oligonucleotides were annealed in pairs (90° C., 5 minutes, followed by slow cooling at room temperature). The 6 paired oligomers were then mixed together, incubated at 50 ° C. for 5 minutes and allowed to cool. They were then ligated overnight at 16° C. with T4 DNA ligase. The strategy is shown diagrammatically in FIGS. 1 and 7 (note P=5′-phosphate). To prevent possible multimerisation, oligomers designated BB2011 and BB2020 were not kinased. The sequences of the oligomers shown in FIGS. 1 and 7 correspond to those given in SEQ. ID NOS:50–61.

The ligation products were separated on a 2% low gelling temperature agarose gel and the DNA fragment of ca. 223 base pairs corresponding to the hirudin HV-1 gene was excised and extracted from the gel. The purified fragment was then ligated to HindIII and EcoRI treated pUC19 plasmid DNA. The transformation of *E. coli* host strains was accomplished using standard procedures. The strain used as a recipient in the transformation of plasmid vectors was HW87 which has the following genotype:

araD139 (ara-leu) DELTA7697 (lacIPOZY) DELTA74 galU
galK hsdR rpsL srl recA56

The use of HW87 was not critical: any suitable recipient strain could be used, for example, *E. coli* AG1, which is available from Northumbria Biologicals Ltd. The recombinant ligation products were transformed into *E. coli* K12 host strain HW87 and plated onto Luria-agar ampicillin (100 μg/ml) plates. Twelve ampicillin-resistant colonies were picked and used to prepare plasmid DNA for sequence analysis. Double stranded dideoxy sequence analysis using a universal sequencing primer BB22 (5′-CAGGGTTTTC-CCAGTCACG-3′), (SEQ ID NO:3) complementary to the universal primer region of pUC19 was used to identify a correct clone pUC19 HV-1. The pUC19 recombinant was used to construct an expression vector.

PREPARATION 2

Construction of a Hirudin HV1 Expression Vector

An expression vector was designed to enable the secretion of hirudin to the extracellular medium after expression in *S. cerevisiae*. Secretion of hirudin is desirable as this facilitates production of the protein with an authentic N-terminus. It also eases purification, limits intracellular proteolysis, reduces potential toxic effects on the yeast host and allows optimal protein folding and formation of native disulphide bonds. Secretion of hirudin through the yeast membrane was directed by fusion of hirudin to the yeast mating type alpha-factor pre-pro-peptide (a naturally secreted yeast peptide).

The yeast expression vector pSW6 (FIG. 2) is based on the 2μ circle from *S. cerevisiae*. (pSW6 was deposited in *S. cerevisiae* strain BJ2168 at The National Collection of Industrial and Marine Bacteria Limited, 23 St. Machar Drive, Aberdeen, AB2 1RY, Scotland, United Kingdom on 23rd Oct. 1990 under Accession No. NCIMB 40326. ) pSW6 is a shuttle vector capable of replication in both *E. coli* and *S. cerevisiae* and contains an origin of DNA replication for both organisms, the leu2 gene ( a selectable marker for plasmid maintenance in the yeast host ) and the ampicillin resistant locus for selection of plasmid maintenance in *E. coli*. (The DNA sequence of the vector has been determined; the *E. coli* sequences are derived from the *E. coli* ColE1-based replicon pAT153. ) The full sequence is given as SEQ-.ID:4. The ability to passage this vector through *E. coli* greatly facilitates its genetic manipulation and ease of purification. pSW6 contains an α-factor pre-pro-peptide gene fused in-frame to the gene for epidermal growth factor (EGF). The expression of this fusion is under the control of an efficient galactose regulated promoter which contains hybrid DNA sequences from the *S. cerevisiae* GAL 1-10 promoter and the *S. cerevisiae* phosphoglycerate kinase (PGK) promoter. Transcription of the EGF gene is terminated in this vector by the natural yeast PGK terminator. The EGF gene in pSW6 can be removed by digestion with restriction endonucleases HindIII and BamHI. This removes DNA encoding both EGF and 5 amino acids from the C-terminus of the α-factor pro-peptide. Genes to be inserted into the pSW6 expression vector must therefore have the general composition: HindIII site α-factor adaptor - gene-BamHI site.

Figure 3:
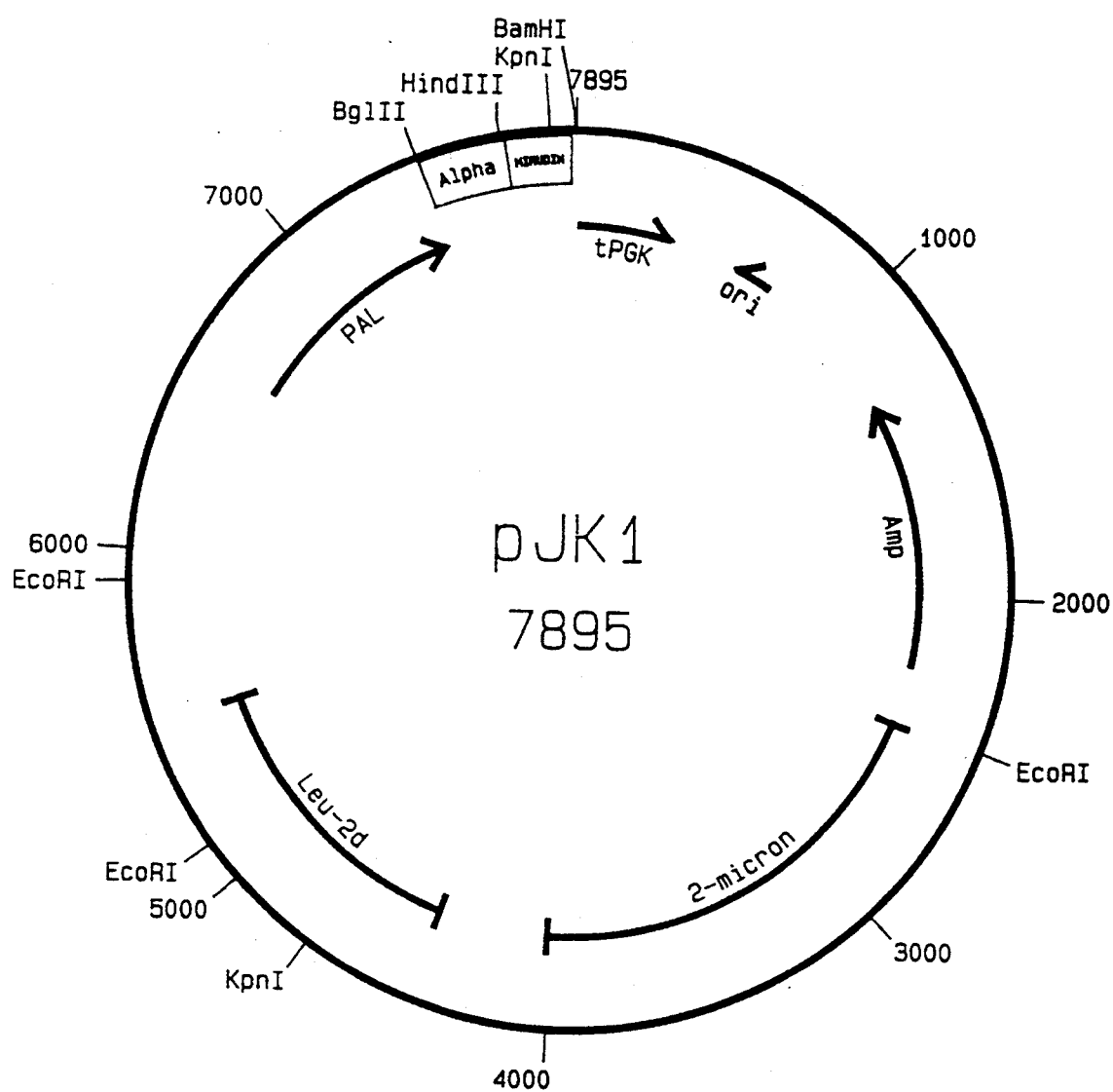
FIG. 3 shows a map of plasmid pJK1 (Preparation 2)

To rebuild the DNA encoding the amino acids at the C-terminal end of the α-factor pro-peptide and to fuse this to the synthetic hirudin gene, an oligonucleotide adapter (5'-AGCTTGGATAAAAGA-3' (top strand, SEQ. ID: 5), 5'-TCTTTTATCCA-3' (bottom strand, SEQ. ID: 6)) containing a HindIII site and codons encoding the Ser, Leu, Asp, Lys and Arg from the C-terminal end of the α-factor pro-peptide was constructed. The α-factor adaptor was ligated to the synthetic HV-1 gene such that the recombinant gene encoded an inframe α-factor pro-peptide fusion to hirudin. The pUC19 HV-1 plasmid DNA of Preparation 1 was first cleaved with BspMI and the overhanging ends were filled using DNA polymerase I Klenow fragment to create a blunt-ended linear DNA fragment. The linearised fragment was separated from uncut plasmid on a 1% low gelling temperature agarose gel, excised and extracted from the agarose gel matrix, then further treated with HindIII. The fragment was then ligated to the alpha-factor adaptor described above and annealed prior to ligation. The recombinant ligation products were transformed into competent cells of E. coli strain HW87 (Preparation 1). Ampicillin resistant transformants were analysed by preparation of plasmid DNA, digestion with HindIII and BamHI and agarose gel electrophoresis. A correct recombinant plasmid was called pJC80. The α-factor adaptor hirudin sequence was removed from pJC80 on a ca. 223 bp HindIII-BamHI DNA fragment (SEQ.ID:7). The fragment was purified on a low gelling temperature agarose gel and ligated to HindIII and BamHI treated pSW6 vector DNA. The recombinant ligation products were transformed into competent cells of E. coli strain HW87. Ampicillin resistant transformants were screened by preparation of plasmid DNA, restriction endonuclease analysis with HindIII and BamHI and agarose gel electrophoresis. A clone with the correct electrophoretic pattern pJK1 (FIG. 3) was identified. This plasmid is the basic vector used for wild-type hirudin HV-1 expression and was used to derive certain other yeast expression vectors as detailed in the remaining preparations and examples.

PREPARATION 3

Expression of Hirudin Synthetic Gene

Plasmid expression vector pJK1 of Preparation 2 was transformed into yeast (S. cerevisiae) strain BJ2168 which has the following genotype:prc-1-407, prb1-1122 pep4-3 leu2 trp1 ura3-52 cir+ using the method of Sherman F. et al (Methods in Yeast Genetics, Cold Spring Harbor Laboratory, (1986)). All yeast media was as described by Sherman et al. Using 2 liter shake flasks, cultures of yeast containing pJK1 were grown in 1 liter batches of 0.67% synthetic complete medium, yeast nitrogen base, with amino acids minus leucine and 1% glucose as a carbon source. After overnight growth at 30° C., the cells were harvested by centrifugation at 3000 rpm for 10 minutes and resuspended in the same synthetic complete medium except that 1% galactose and 0.2% glucose was used as the carbon source. This induces gene expression from the hybrid PGK promoter. Cells were grown in the induction medium for 3 days. After this period, the supernatant was harvested and assayed for hirudin activity as described in Example 2, Section D, below.

EXAMPLE 1

Construction of a Hirudin-IEGR-Hirudin Fusion Gene and a Vector for its Expression A factor Xa-cleavable hirudin fusion protein molecule has been engineered in which two full length hirudin molecules are joined by the peptide linker sequence Ile Glu Gly Arg (See SEQ.ID: NOS:8 and 9). The molecule is designed to be activatable by factor Xa cleavage. The strategy for construction of the hirudin-IEGR-hirudin gene is detailed below.

A gene encoding the hirudin-IEGR-hirudin molecule was constructed by oligonucleotide directed mutagenesis and molecular cloning. Mutagenesis was carried out according to the method of Kunkel et al., Methods in Enzymology, 54, 367-382 (1987). Host strains are described below.

E. coli strains

RZ1032 is a derivative of E. coli that lacks two enzymes of DNA metabolism: (a) dUTPase (dut), the lack of which results in a high concentration of intracellular dUTP, and (b) uracil N-glycosylase (ung) which is responsible for removing mis-incorporated uracils from DNA (Kunkel et al., loc. cit.). A suitable alternative strain is CJ236, available from Bio-Rad Laboratories, Watford WD1 8RP, United Kingdom. The principal benefit is that these mutations lead to a higher frequency of mutants in site directed mutagenesis. RZ1032 has the following genotype:

HfrKL16PO/45[lysA961-62), dut1, ung1, thi1, recA, Zbd-279::Tn10, supE44

JM103 is a standard recipient strain for manipulations involving M13 based vectors. The genotype of JM103 is DELTA (lac-pro), thi, supE,strA, endA, sbcB15, hsp4, F' traD36, proAB, lacIq, lacZDELTAM15. A suitable commercially available alternative E. coli strain is E. coli JM109, available from Northumbria Biologicals Ltd.

Mutagenesis

Prior to mutagenesis it was neccesary to juxtapose two adjacent hirudin genes in an M13 mutagenesis vector. This was accomplished as described below. pJK1 vector DNA of Preparation 2 was prepared and an aliquot treated with restriction endonucleases BglII and BamHI, a ca. 466 bp BglII-BamHI DNA fragment from this digestion was gel purified and ligated to BamHI treated and phosphatased pJC80 vector DNA of Preparation 2. The recombinant ligation products were transformed into competent cells of E. coli strain HW87 (Preparation 1). Ampicillin (100 μg/ml) resistant clones were analysed by plasmid DNA preparation, restriction endonuclease digestion and gel electrophoresis. Clones with inserts in the desired orientation were identified after digestion with KpnI which released a DNA fragment of ca. 465 bp in length. (The products of KpnI digestion were analysed on an agarose gel.) One of the correct clones, pJK002, was used for the remaining constructions, this vector contains a ca. 465 bp KpnI DNA fragment which encodes a C-terminal portion of a first hirudin gene, a complete α-factor pre-pro-peptide sequence and the N-terminal portion of a second hirudin gene. In order to delete the α-factor pre-pro-peptide sequence and to insert DNA encoding a factor Xa-cleavable amino acid linker sequence (IEGR), the ca. 465 bp KpnI DNA fragment was transferred into a bacteriophage mutagenesis vector M13mp18. Plasmid DNA of pJK002 was prepared and a portion was digested with KpnI. The ca. 465 bp KpnI DNA fragment from pJK002 was gel purified and ligated to KpnI treated and phosphatased M13mp18. The recombinant ligation products were transfected into competent cells of E. coli strain JM103. Single stranded DNAs from putative recombinant phage plaques were prepared and analysed by dideoxy sequence analysis using the M13 universal sequencing primer (SEQ. ID NO: 11; see below). A clone pGC609 containing the KpnI fragment in the correct orientation was identified. The α-factor pre-pro-peptide sequence between the two hirudin sequences of pGC609 was deleted and the DNA encoding the Factor Xa-cleavable amino acid linker (IEGR) inserted by site directed mutagenesis. Single stranded DNA of pGC609 was prepared from *E. coli* strain RZ1032 and was used as a template for mutagenesis with a 46mer oligonucleotide BB2988: (5'-CAGTCGGTGTAAACAACTCTTCCTT-CGATCTGCAGATATTCTTCTG-3') (SEQ. ID: NO:10). Single stranded DNAs were prepared from putative mutant plaques and were analysed by dideoxy DNA sequence analysis using an M13 universal sequencing primer (United States Biochemical Corporation. P.O. Box 22400, Cleveland, Ohio 44122. USA. Product No. 70763 5'-GTTTTCCCAGTCACGAC-3'), (SEQ. ID: NO:11). A correct clone, pGC610, was identified. To construct the full length hirudin-IEGR-hirudin gene the central core of the fusion molecule encoded on the ca. 210 bp KpnI fragment of pGC610 was cloned into the KpnI site of pJC80 of Preparation 2. Replicative form DNA of pGC610 was prepared and digested with KpnI. The ca. 210 bp KpnI DNA fragment encoding the central core of the hirudin-IEGR-hirudin protein was gel purified and ligated to KpnI treated and phosphatased pJC80 of Preparation 2. The recombinant ligation products were transformed into competent cells of *E. coli* strain HW87 (Preparation 1). Ampicillin (100 μg/ml) resistant transformants were analysed by preparation of plasmid DNA, restriction endonuclease digestion with PstI and agarose gel electrophoresis. A clone with the correct electrophoretic pattern pDB1 was identified as containing a ca. 210 bp DNA fragment after PstI digestion.

To create a vector for the expression of the factor Xa-cleavable hirudin-IEGR-hirudin fusion protein the gene was cloned into the yeast expression vector pSW6 of Preparation 2. Plasmid DNA of pDB1 was treated with HindIII and BamHI and the ca. 420 bp HindIII-BamHI DNA fragment containing the factor Xa-cleavable hirudin-IEGR-hirudin gene was gel purified and ligated to HindIII and BamHI treated pSW6 DNA of Preparation 2. The recombinant ligation products were transformed into competent cells of *E. coli* strain HW87. Ampicillin (100 μg/ml) resistant transformants were screened by preparation of plasmid DNA, restriction endonuclease analysis with HindIII and BamHI and agarose gel electrophoresis. A clone with the correct electrophoretic pattern pDB2 was identified. pDB2 contained the hirudin-IEGR-hirudin gene fused in frame to the yeast α-factor pre-pro-peptide sequence. pDB2 plasmid DNA was prepared and used to transform yeast strain BJ2168 (Preparation 3) according to the method of Sherman F. et al (Methods in Yeast Genetics, Cold Spring Harbor Laboratory, New York (1986)).

EXAMPLE 2

Purification of Hirudin and Hirudin-IEGR-Hirudin

The procedure of Preparation 3 was generally followed for the expression of hirudin and hirudin-IEGR-hirudin proteins. Hirudin and hirudin-IEGR-hirudin are purified from yeast culture broth. Cells were first removed by centrifugation at 3000 rpm for 10 minutes. The supernatant was then assayed for biological activity using a chromogenic assay (see below, section D). Production levels from shake flask cultures were routinely between 10–15 mg/liter of culture. The hirudin protein was purified by preparative HPLC (DYNAMAX (Trade Mark) C18, 300 angstroms). The column was first equilibrated in 15% acetonitrile, 0.1% trifluoro acetic acid. Then 2.5–3 mg of hirudin activity as determined by chromogenic assay (section D) was loaded onto the column. The protein was eluted using a 15–40% acetonitrile gradient at 3 ml/minute over 25 min. The purity of the isolated protein was assessed by analytical HPLC (VYDAC (Trade Mark) C18 reverse phase), N-terminal sequence analysis and mono Q FPLC as described below.

A. Assessing Purity by Analytical HPLC

Samples were analysed on a VYDAC (Trade Mark) C18 column (15×0.46 cm, particle size 5 micron) equilibrated with 10% acetonitrile, 0.1% trifluroacetic acid (TFA). Purified protein (20 μg) was loaded in 10% acetonitrile, 0.1% TFA. Protein was eluted at a flow rate of 1 ml/minute using an acetonitrile gradient from 10–40% in 0.1% TFA over 30 minutes. The eluted protein sample was monitored by absorbance at 280 nm.

B. Analysis of Purity by Mono Q FPLC

Samples were analysed on a Mono Q FPLC column (5×0.5 cm, Pharmacia) equilibrated in 20 mM Tris.HCl pH 7.5. Approximately 15 μg of lyophilised protein was reconstituted in 1 ml 20 mM Tris. HCl pH 7.5 and loaded onto the column. Protein was eluted using a gradient of 0–250 mM NaCl in 20 mM Tris. HCl buffer (pH 7.5) at a flow rate of 1 ml/minute over 30 minutes.

C. N-terminal Sequence Analysis

N-terminal sequence analysis was performed by automated Edman degradation using an Applied Biosystems Protein Sequencer, model 471 A (Applied Biosystems, Foster City, Calif.).

Purified material that was greater than 95% pure, was dried down in a SPEEDIVAC (trade mark of Savant Instruments Inc. Hicksville, N.Y. U.S.A.) and reconstituted in 0.5 ml of 0.9% (w/v) saline for assay.

D. Hirudin Anti-thrombin Chromogenic Activity Assay

The ability of hirudin and molecules containing hirudin to inhibit the thrombin catalysed hydrolysis of the chromogenic substrate tosyl-Gly-Pro-Arg-p-nitroanilide (CHROMOZYM TH (trade mark of Boehringer-Mannheim)) was used as an assay to determine their anti-thrombin activity. Protein samples (50 μl) diluted in 0.1M Tris.HCl pH8.5, 0.15M NaCl, 0.1% (w/v) PEG 6000 were mixed with 50 μl human thrombin (Sigma, 0.8 U/ml in the above buffer) and 50 μl CHROMOZYM TH (2.5 mM in water) in 96 well plates (Costar). The plates were incubated at room temperature for 30 minutes. The reaction was terminated by adding 50 μl 0.5M acetic acid and the absorbance read at 405 nm using an automatic plate reader (Dynatech). Quantitation was performed by comparison with a standard hirudin preparation (recombinant [Lys-47]-HV-2 purchased from Sigma: Sigma Chemical Co. Ltd, Fancy Road, Poole, Dorset BH11 7TG, United Kingdom).

EXAMPLE 3

Cleavage and Activation of Hirudin-IEGR-Hirudin Fusion Protein

Purified hirudin-IEGR-hirudin fusion protein was incubated with Factor Xa. The reaction was performed at 37° C. in a total volume of 150 μl of 0.1M Tris.HCl buffer pH 7.8 and contained 2.06 nmol fusion protein and 0.4 nmol Factor Xa. Analysis of the reaction mixture by sodium dodecyl sulphate-polyacrylamide gel electro- phoresis (SDS-PAGE) demonstrated cleavage to products of a similar size to native hirudin. Reverse phase HPLC analysis of the cleavage reaction as in Example 2, section A, demonstrated the appearance of two new species with retention times (RT) of 17 and 20 minutes compared to 22 minutes for the intact fusion protein.

Measurements of specific activity were made on the products isolated from a cleavage reaction. Using a chromogenic assay according to the method of Example 2, section D, to measure hirudin activity in antithrombin units and A 280 nm to determine protein concentration, the following results were obtained: product RT 17 min., 6125 U/mg; product RT 20 min., 5226 U/mg; intact hirudin-IEGR-hirudin, RT 22 min., 588 U/mg. Cleavage therefore produces an approximate 2-fold increase in specific activity, with the products displaying similar values to that recorded for a recombinant hirudin sample (6600 U/mg) as measured according to the method of Example 2, section D.

Purified cleavage products and the intact fusion protein were subjected to N-terminal sequence analysis.

In each case the sequence obtained was identical to that of native hirudin (HV-1), (VVYTD); SEQ ID NO: 70.

It has thus been demonstrated that the hirudin-IEGR-hirudin fusion protein can be cleaved by Factor Xa to produce two products with hirudin activated. Cleavage of the fusion protein is accompanied by activation as the products of cleavage have approximately double the specific activity of the fusion protein.

PREPARATION 4

Isolation of a Streptokinase Gene

Streptokinase is secreted by Lancefield's Group C streptococci and cloning of the streptokinase gene from *Streptococcus equisimilis* strain H46A has been described (Malke, H. and J. J. Ferretti, *P.N.A.S.* 81 3557-3561 (1984)). The nucleotide sequence of the cloned gene has been determined (Malke, H., Roe, B. and J. J. Ferretti, *Gene* 34 357-362 (1985)). A gene encoding streptokinase has been cloned from *S. equisimulis* (ATCC 9542 or ATCC 10009) for use in the current invention. Methods that can be used to isolate genes are well documented and the procedure used to isolate the streptokinase gene is summarized in the following protocol.

1. DNA was prepared either from *Streptococcus equisimilis* is (Lancefield's Group C) ATCC 10009 or from ATCC 9542 grown in brain-heart infusion medium (Difco-Bacto Laboratories, PO Box 14B, Central Avenue, E. Mosely, Surrey KT8 OSE, England) as standing cultures. Chromosomal DNA was isolated from approximately 1.5 ml of cells at a density of $1 \times 10^{11}$ cells/ml. The cells were harvested and washed in 1 ml buffer (0.1M potassium phosphate pH 6.2). The pellet was resuspended in 400 μl of the same buffer and 500 units of mutanolysin (Sigma Chemical Company Ltd, Fancy Road, Poole, Dorset BH17 7TG, UK) in 100 μl volume was added. This mix was incubated at 37° C. for 1 hour. The cells were harvested by centrifugation and again washed in buffer. The cells were resuspended in 500 μl of a solution containing 50 mM glucose, 10 mM EDTA and 25 mM Tris HCl pH 8.0 and incubated at 37° C. for approximately 1 hour with the mix being shaken gently to prevent the cells settling. A 500 μl aliquot of a solution containing 0.4% SDS and proteinase K (100 μg/ml) (Sigma Chemical Company Ltd) was added and the mix was incubated at 37° C. for 1 hour until it became viscous and clear. The mix was then extracted three times with phenol equilibrated with TE buffer (10 mM Tris HCl 1 mM EDTA pH 8.0). The aqueous phase was removed into an eppendorf tube, sodium acetate added to a final concentration of 0.3M and 2.5 volumes of ethanol added. The mix was incubated at −70° C. for 1 hour to precipitate the DNA. The DNA was pelleted by centrifugation, washed with 70% ethanol and then resuspended in 200 μl TE buffer.

2. The Polymerase Chain Reaction (PCR) was used to amplify the streptokinase sequence (Saiki R. et al *Science*, 239, 487-491 (1988)). Two primers were designed based on the published streptokinase sequences. The primer encoding the antisense strand at the 3' end of the gene was a 40mer BB1888 (5'GTTCATG-GATCCTTATTTGTCGTTAGGGTTATCAGG-TATA 3'), ( SEQ. ID: NO:12) which also encoded a BamHI site. The primer encoding the sense strand at the 5' end of the gene encoded an EcoRI site in addition to the streptokinase sequence and was the 40 mer BB1887 (5'TCAAGTGAATTCATGAAAAATTACT-TATCTTTTGGGATGT 3'), (SEQ ID: NO:13). Forty cycles of PCR were performed with the denaturation step at 95° C. for 2 minutes, followed by annealing of the primers for 3 minutes at 55° C. and extension at 70° C. for 4.5 minutes. A sample of the reaction product was analysed on a 0.8% agarose gel. A single amplified DNA fragment at c.a. 1.3 kB, which corresponds to the expected size of the streptokinase gene, was observed.

3. A 30 μl sample of the product was digested with the restriction endonucleases EcoRI and BamHI, analysed on a low gelling temperature agarose gel and the c.a. 1.3 kb DNA fragment was isolated from the gel. The band was extracted from the gel and ligated into the plasmid pUC19 which had been cleaved with EcoRI and BamHI to form the plasmid pUC19SK.

The entire ca. 1330 bp EcoRI-BamHI fragment from pUC19SK was sequenced by dideoxy sequence analysis. To facilitate the sequencing, The EcoRI-BamHI DNA fragment of pUC19SK was transferred to M13 sequencing vectors mp18 and mp19 in two halves. A ca. 830 bp EcoRI-HindIII DNA fragment was separately transferred into EcoRI and HindIII treated M13mp18 and M13mp19. The products from these two ligation events were separately transfected into competent cells of *E. coli* host JM103. Single stranded DNA was prepared and used for dideoxy sequence analysis using the primers listed in SEQ ID NOS: 62 to 68 and SEQ ID NO: 11. A ca. 490 bp HindIII-BamHI fragment was gel purified after treatment of pUC19SK with HindIII and BamHI. This DNA fragment was separately ligated to M13mp18 and M13mp19 which had been treated with HindIII and BamHI. The products of these two ligations was transfected into competent cells of *E. coli* host JM103. Single stranded DNA was prepared and used for dideoxy sequence analysis with the primers shown in SEQ ID NOS:62 to 68 and SEQ ID NO: 11. The entire sequence of the EcoRI-BamHI PCR derived DNA fragment is shown in SEQ ID NOS:14. and 15.

EXAMPLE 4

Construction of Streptokinase Expression Vectors

A number of alternative streptokinase expression vectors have been constructed for expression in either yeast S. cerevisiae or E. coli K12.

1) Vectors for secretion to the periplasm of E. coli K12

Two vectors were designed to enable the secretion of streptokinase to the periplasmic space after expression in E. coli K12. Secretion of streptokinase is desirable to facilitate production of protein with an authentic N-terminus, to ease purification, to reduce potential toxic effects and to limit intracellular proteolysis. Secretion of streptokinase through the E. coli cytoplasmic cell membrane was directed by either the streptokinase signal peptide or the E. coli major outer membrane protein A (OmpA) signal peptide (OmpAL).

A. Secretion using the streptokinase leader

Figure 4:
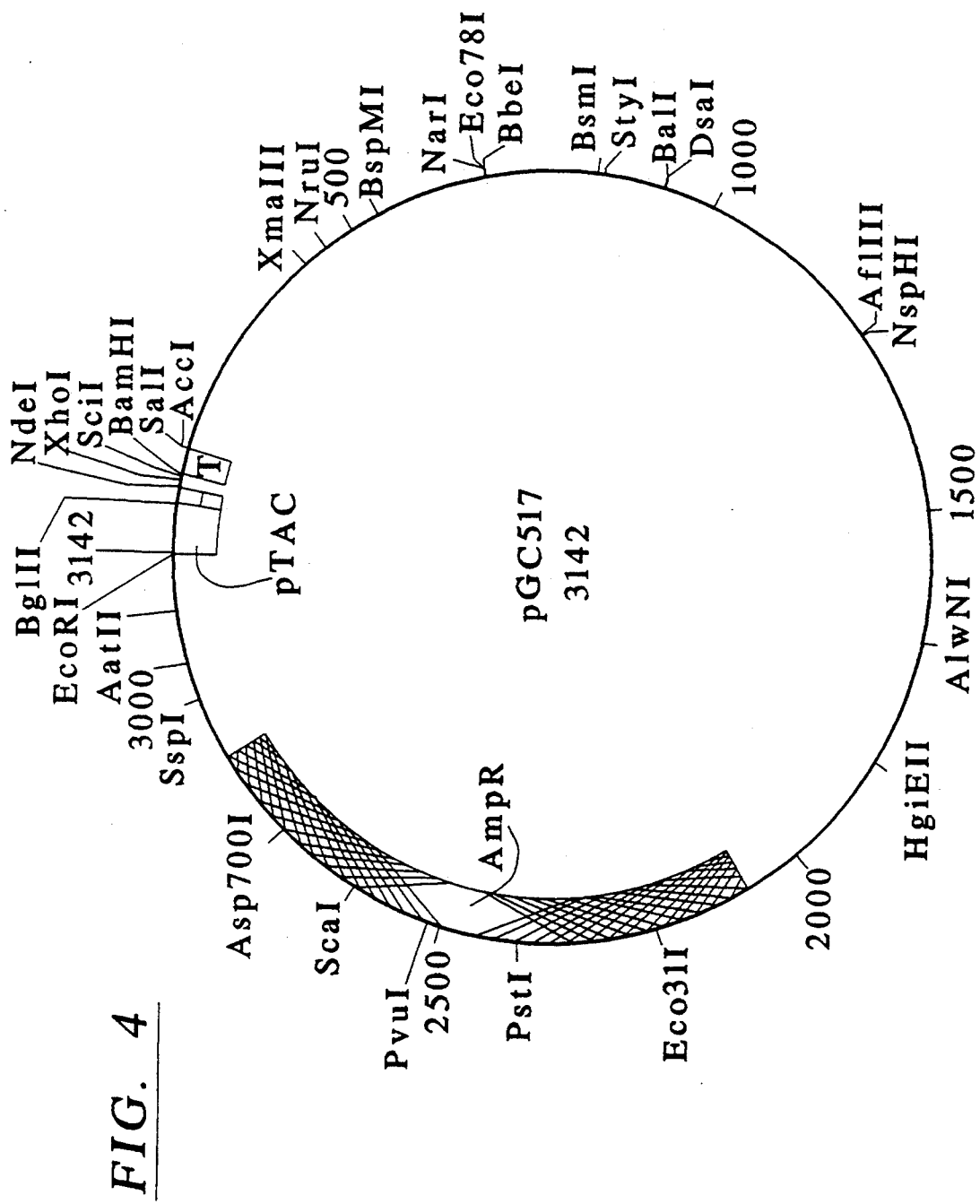
FIG. 4 shows a map of plasmid pGC517 (Example 4)

The streptokinase gene of Preparation 4 was transferred into the E. coli expression vector pGC517 (FIG. 4). pGC517 contains the regulatable ptac promoter, a ribosome binding site and a synthetic transcriptional terminator. pGC517 was deposited in E coli K12 at The National Collection of Industrial and Marine Bacteria Limited, 23 St. Machar Drive, Aberdeen, AB2 1RY, Scotland, United Kingdom on 5th December 1990 under Accession No. NCIMB 40343. Genes can be cloned into the expression site of pGC517 on NdeI-BamHI DNA fragments. It was necessary to engineer a NdeI site into the 5' end of the streptokinase gene to enable subsequent cloning into pGC517. The NdeI site was introduced by site-directed mutagenesis. To construct the vector for the site directed mutagenesis, plasmid DNA of vector pUC19SK of Preparation 4 was prepared and digested with EcoRI and BamHI and the ca. 1.3 Kb EcoRI-BamHI DNA fragment was gel purified and ligated to M13mp18 treated with EcoRI and BamHI. Recombinant ligation products were transfected into competent cells of E. coli strain JM103 (Example 1). Single stranded DNA was prepared from the putative recombinant plaques and analysed by dideoxy sequence analysis using the M13 universal sequencing primer (SEQ ID: NO: 11 of Example 1). One of the correct recombinant phages was called pGC611. Single stranded DNA of phage pGC611 was prepared from E. coli strain RZ1032 (Example 1) and used as a template for mutagenesis. An NdeI restriction site was introduced by site-directed mutagenesis at the 5' end of the streptokinase gene such that the NdeI site overlapped the streptokinase initiation codon. The mutagenesis was performed using a 26-mer BB2175 (5'-GATAAG-TAATTTTTCATATGAATTCG-3'), (SEQ ID: NO:16). Single stranded DNAs were prepared from putative mutant plaques and were screened by dideoxy sequence analysis using the 18mer sequencing primer BB2358 (5'-CATGAGCAGGTCGTGATG-3'), (SEQ ID: NO:17) and a correct clone pGC612 was identified.

To construct an expression vector, the streptokinase gene carrying the newly introduced NdeI site, was cloned into the pGC517 expression vector. Replicative form DNA was prepared from pGC612 and was digested with NdeI and BamHI and the ca. 1.3 kb NdeI-BamHI DNA fragment was gel purified. This fragment was then ligated to NdeI and BamHI treated pGC517 DNA. The recombinant ligation products were transformed into competent cells of E. coli strain JM103. Ampicillin (100 μg/ml) resistant transformants were analysed by plasmid DNA preparation, restriction endonuclease digestion with BglII and BamHI and agarose gel electrophoresis. One of the correct clones, pKJ2, was verified by dideoxy sequence analysis using the sequencing primer BB2358. This vector contains the entire streptokinase gene including the sequences encoding the streptokinase signal peptide leader region and was used for the expression of streptokinase in E. coli.

B. Secretion using the E. coli OmpA leader

As an alternative secretion signal, a DNA sequence encoding the major outer membrane protein A (OmpA) signal peptide (OmpAL) was fused to the DNA sequence encoding the mature streptokinase protein; see SEQ ID NOS: 18 and 19 A DNA fragment encoding streptokinase was obtained by preparing pUC19SK vector DNA, treating the DNA with EcoRI and filling-in the overhanging single stranded DNA ends with DNA polymerase I Klenow fragment to create a blunt-ended linear DNA fragment. The fragment was next digested with BamHI and the ca. 1.3 kb blunt-ended-BamHI DNA fragment containing the streptokinase gene was gel-purified. The DNA sequence encoding OmpAL is available on an expression vector pSD15. The pSD15 vector contains a gene encoding an insulin like growth factor II gene (IGF-II) fused to the OmpAL signal sequence. pSD15 was deposited in E. coli K12 at The National Collection of Industrial and Marine Bacteria Limited, 23 St. Machar Drive, Aberdeen, AB2 1RY, Scotland, United Kingdom on 5th December 1990 under Accession No. NCIMB 40342. In order to use pSD15 as a vector to provide the OmpAL DNA sequence, pSD15 vector DNA was treated with NheI, the single stranded DNA overhanging ends were filled-in with DNA polymerase I Klenow fragment to create a blunt-ended linear DNA fragment. The linear DNA fragment was next digested with BamHI which removed ca. 123 bp from the 3' end of the IGF-II gene in pSD15. After restriction endonuclease digestion the cleaved linear DNA fragment was treated with phosphatase, to prevent recircularisation of any partially cut vector DNA and was gel purified then ligated to the blunt-ended-BamHI DNA fragment containing the streptokinase gene. The ligated mixture was transformed into competent cells of E. coli strain HW87 (Preparation 1). Ampicillin (100 μg/ml) resistant recombinants carrying the streptokinase gene were characterised by preparation of plasmid DNA, restriction endonuclease analysis with BglII and HindIII and agarose gel electropohoresis. A construct of the correct electrophoretic pattern was called pKJ1. Vector pKJ1 contains the DNA encoding OmpAL and streptokinase separated by a region of DNA not required in further constructs. The sequence of the insert DNA in pKJ1 was confirmed by dideoxy sequence analysis with a 44-mer oligonucleotide BB58 (5'-AGCTCGTAGACACTCT-GCAGTTCGTTTGTGGTGACCGTGGCTTC-3') SEQ ID: NO:20. In order to create a DNA template for the deletion loopout mutagenesis of the unwanted DNA sequence, the BglII to HindIII DNA fragment from pKJ1 was cloned into a vector M13mp19. pKJ1 vector DNA was treated with BglII and HindIII to produce a ca. 1026 bp DNA fragment, which was gel purified and ligated into the polylinker region of M13mp19 replicative form DNA treated with BamHI and HindIII. Ligation products were transfected into competent cells of *E. coli* strain JM103. Single stranded DNAs were prepared from putative recombinant plaques and a correct clone (pGC600) identified by dideoxy sequence analysis using the M13 universal sequencing primer (SEQ ID: NO:11, Example 1).

Mutagenesis on template pGC600 was performed using a 30-mer oligonucleotide mutagenesis primer BB2658 (5'-ACCGTAGCGCAGGCCATTGCT-GGACCTGAG-3') SEQ ID: NO: 21. Single stranded DNAs were prepared from putative mutant plaques and a clone, pGC601, containing the required deletion was identified using dideoxy sequence analysis with the M13 universal sequencing primer (SEQ ID: NO: 11). pGC601 contains part of the OmpAL-streptokinase fusion required for the secretion of streptokinase from this signal peptide in *E. coli*, but DNA encoding the C-terminal portion of streptokinase is absent. In order to reconstruct the streptokinase gene, replicative form DNA from pGC601 was digested with restriction enzymes NdeI and HindIII and the ca. 810 bp NdeI-HindIII DNA fragment containing the DNA sequences encoding OmpAL leader peptide sequence fused to the N-terminal portion of streptokinase was gel purified. pJK2 vector DNA was treated with restriction enzymes NdeI and HindIII followed by treatment with phosphatase and the ca. 3620 bp NdeI-HindIII vector DNA fragment containing the essential vector sequences and the C-terminal portion of the streptokinase gene was gel purified. The ca. 810 bp NdeI-HindIII (pGC601) and ca. 3620 NdeI-HindIII (pKJ2) gel purified DNA fragments were ligated together and the recombinant ligation products were transformed into competent cells of *E. coli* strain HW1110 (lacIq). The lacIq mutation in this strain enhances repression of transcription from the tac promoter. Any other lacIq strain, for example JM103 could be used instead. The ampicillin resistant transformants were screened by preparation of plasmid DNA followed by restriction endonuclease analysis using NdeI and HindIII. Agarose gel electrophoresis of digestion products was used to identify a correct clone which was called pLGC1. The pLGC1 construct was verified by dideoxy sequence analysis using a 17-mer oligonucleotide BB2753 (5'-GACAC-CAACCGTATCAT-3'), (SEQ ID: NO: 22) to sequence through the BamHI site and primer BB3510 (5'-CACTATCAGTAGCAAAT-3'), (SEQ ID: NO:23) to sequence through the sequence encoding the OmpA leader.

2) Intracellular Expression in *E. coli*

As streptokinase contains no disulphide bonds there is no requirement for secretion to encourage native protein folding and although streptokinase is naturally secreted, intracellular expression offers several potential advantages such as high yield and inclusion body formation which may facilitate purification. As an alternative production route, an expression vector was designed for intracellular production of streptokinase in *E. coli*. DNA encoding the amino acids 2 to 21 of the OmpAL signal peptide sequence which was fused to mature streptokinase in pGC601 were deleted by loop-out site directed mutagenesis using single stranded DNA of pGC601 with a 31-mer mutagenesis oligonucleotide BB3802 (5'-GAAATACTTACATAT-GATTGCTGGACCTGAG-3'), (SEQ ID: NO:22). In addition to deleting the OmpAL signal peptide coding sequence, BB3802 fused the methionine codon (ATG) of the OmpAL signal peptide sequence to the first codon of mature streptokinase to create the 5' end of gene encoding a Methionyl-streptokinase fusion protein (see SEQ ID: NOS: 25 and 26). The ATG codon was used to allow initiation of translation at the correct position. Single stranded DNA was prepared from putative mutant plaques and a clone containing the desired mutation, pGC602 was identified using dideoxy sequence analysis with the M13 universal sequencing primer (SEQ ID: NO: 11). The C-terminal portion of the streptokinase gene is missing in pGC602. In order to reconstruct the intact mature streptokinase coding sequence, replicative form DNA from pGC602 was digested with restriction enzymes NdeI and HindIII and the ca. 755 bp NdeI-HindIII DNA fragment encoding the N-terminal portion of the Methionyl-streptokinase protein was gel purified and ligated to the gel purified ca. 3620 bp NdeI-HindIII pLGC2 vector DNA fragment described in Example 6 below. The recombinant ligation mixture was transformed into competent cells of *E. coli* strain HW1110 (lacIq). Ampicillin (100 μg/ml) resistant transformants were screened by plasmid DNA preparation, restriction endonuclease digestion and agarose gel electrophoresis. A clone, pGC603, with the correct electrophoretic pattern after NdeI and HindIII digestion, was identified. Vector pGC603 was used for the intracellular expression of Methionyl-streptokinase in *E. coli* strain HW1110.

3) Construction of Expression Vectors for the Secretion of Streptokinase from the Yeast *S. cerevisiae*

Expression vectors were designed to enable the secretion of streptokinase to the extracellular medium after expression in *S. cerevisiae*. Secretion of streptokinase is desirable to facilitate production of protein with an authentic N-terminus, to ease purification, to limit intracellular proteolysis and to reduce potential toxic effects on the yeast host. Secretion of streptokinase through the yeast membrane was directed by either the natural streptokinase signal peptide or by fusion of mature streptokinase to the yeast mating type alpha-factor pre-pro-peptide (a naturally secreted yeast peptide) see SEQ ID: NOS:27 and 28.

A) Secretion of Streptokinase using the Streptokinase Signal Peptide

The streptokinase gene with its natural signal peptide was cloned into the yeast expression vector pSW6 to allow its expression in the yeast *S. cerevisiae*. Vector DNAs of pKJ2 and pSW6 of Preparation 2 were prepared. Both DNAs were treated with restriction enzymes BglII and BamHI and the ca. 1420 bp DNA fragment from pKJ2 and the ca. 7460 bp vector DNA fragment from pSW6 were gel purified and ligated together. The recombinant ligation products were transformed into competent cells of *E. coli* strain DH5 (supE44, hsdR17, recA1, endA1, gyrA96, thi-1, relA1), but any other good transforming strain could be used, for example JM109 of Example 1. Ampicillin (100 μg/ml) resistant transformants were analysed by preparation of plasmid DNA, restriction endonuclease digestion with BamHI and HindIII and agarose gel electrophoresis. A clone with the correct electrophoretic pattern pSMD1/111 was used for the expression of streptokinase from its own signal peptide sequence from the yeast *S. cerevisiae*. Plasmid expression vector pSMD1/111 was transferred into yeast (*S. cerevisiae*) strain BJ2168 according to the method of Preparation 3.

B) Secretion of Streptokinase using the pre-pro-α-Factor Secretion Leader

A gene fusion to enable the streptokinase gene of Preparation 4 to be expressed in yeast and to be secreted by the yeast mating type α-factor pre-pro-peptide was designed and constructed using site-directed mutagenesis and molecular cloning see SEQ ID: NOS:27 and 28. The construction involved mutagenesis to create an α-factor-streptokinase fusion gene and molecular cloning to reconstruct the DNA sequences encoding the mature streptokinase protein sequence. Single stranded DNA of pGC600 prepared from *E. coli* strain RZ1032 (Example 1) was used as a mutagenesis template with the 36-mer oligonucleotide BB3624 (5'-GTCCAAGC-TAAGCTTGGATAAAAGAATTGCTGGACC-3') SEQ ID: NO:29. Single stranded DNA from putative mutant plaques were analysed by dideoxy sequence analysis using the M13 universal sequencing primer (SEQ ID: NO:11) and a mutant clone, pGC614, with the desired sequence was identified. In pGC614 the OmpA-IGFII-Streptokinase signal peptide encoding sequences of pGC600 have been deleted and the α-factor linker encoding the C-terminal 5 amino acids of the α-factor pro-peptide described in Preparation 2 have been inserted. To reconstruct the streptokinase gene in a yeast expression vector, two stages of genetic manipulation were required. First the C-terminal portion of streptokinase was cloned into a yeast expression vector and this new construct was used to clone in the N-terminal α-factor-streptokinase fusion portion of the gene, thus reconstructing a mature streptokinase coding region fused to the α-factor pre-propeptide gene. Vector DNAs of pKJ2 and pSW6 (Preparation 2) were prepared and digested with HindIII and BamHI and the ca. 485 bp. DNA fragment from pKJ2 and the ca. 7750 bp. vector DNA fragment from pSW6 were gel purified and ligated. Recombinant ligation products were transformed into competent cells of *E. coli* strain DH5. Ampicillin resistant transformants were screened by preparation of plasmid DNA, restriction endonuclease digestion with HindIII and BamHI and agarose gel electrophoresis. A clone with the correct electrophoretic pattern pSMD1/119 was isolated. It contains DNA encoding the C-terminal portion of streptokinase cloned into a yeast expression vector. The DNA encoding the N-terminal portion of streptokinase and the alpha-factor adaptor sequence were next cloned into pSMD1/119. Replicative form DNA of pGC614 was prepared and treated with HindIII and ligated to pSMD1/119 vector DNA which had been treated with HindIII and phosphatased. The recombinant ligation products were transformed into competent cells of *E. coli* strain DH5. Ampicillin (100 μg/ml) resistant transformants were screened by preparation of plasmid DNA, restriction endonuclease analysis with DraI and agarose gel electrophoresis. A clone with the correct electrophoretic pattern pSMD1/152 gave DraI digestion products of ca. 4750, 1940, 1520 and 700 bp. in length. pSMD1/152 was used for the expression and secretion of streptokinase using the alpha factor pre-pro-sequence from the yeast *S. cerevisiae*. Plasmid expression vector pSMD1/152 was transferred into yeast (*S. cerevisiae*) strain BJ2168 according to the method of Preparation 3.

EXAMPLE 5

Construction of a Gene Encoding a Core Streptokinase Protein

A gene encoding a truncated methionyl streptokinase molecule (aa 16-383) was designed and constructed by oligonucleotide directed loopout deletions and molecular cloning; see SEQ ID: NOS:30 and 31 DNA encoding the amino acids 2 to 21 of the OmpAL signal sequence, the DNA encoding IGF-II, the DNA encoding the streptokinase signal peptide and the first 15 amino acids of the mature streptokinase protein in pGC600 of Example 4B were deleted by loopout mutagenesis using a 33-mer oligonucleotide BB3862: 5'-GAAATACT-TACATATGAGCCAATTAGTTGTTAG-3'; SEQ ID: NO:32. Single stranded DNA was prepared from *E. coli* RZ1032 cells infected with pGC600 and used as the template for mutagenesis with primer BB3862. Single stranded DNA was prepared from putative mutant plaques and a clone pGC604 containing the desired deletion was identified by dideoxy sequence analysis using the M13 universal sequencing primer (SEQ ID: NO:10, Example 1).

Amino acids 384 to 414 were deleted from streptokinase by loopout mutagenesis using a 28-mer oligonucleotide BB3904: 5'-CCCGGGGATCCTTAGG-CTAAATGATAGC-3'; SEQ ID: NO: 33. The template for the mutagenesis was single stranded DNA of M13JK1 of Example 10 containing the ca. 500 bp HindIII-BamHI DNA fragment encoding the 3' end of the streptokinase gene from pUC19SK of Preparation 4. Single stranded DNA from putative mutant plaques was prepared and a clone pGC605 containing the desired deletion was identified by dideoxy sequence analysis using the M13 universal sequencing primer (SEQ ID: NO:11, Example 1).

The intact core streptokinase molecule was reconstructed from the two mutated halves by a two step ligation incorporating the NdeI-HindIII DNA fragment from pGC604 (containing the DNA encoding the N-terminal portion of the core streptokinase molecule) and the HindIII-BamHI DNA fragment from pGC605 (containing the DNA encoding the C-terminal portion of the core streptokinase molecule) into the vector DNA pLGC2 of Example 6 below. First the pGC604 DNA was digested with NdeI and HindIII. A DNA fragment of ca. 710 bp. was gel purified. Vector DNA was prepared from pLGC2 of Example 6 and treated with NdeI and HindIII and phosphatased. The linear vector DNA was gel purified and the two fragments were ligated together. The recombinant ligation products were transformed into competent cells of *E. coli* strain HW1110. Ampicillin (100 μg/ml) resistant transformants were screened for the required clone by preparation of plasmid DNA, restriction endonuclease analysis with NdeI and HindIII followed by agarose gel electrophoresis of the digestion products. One construct with the correct electrophoretic pattern, pGC617, was identified.

To clone the DNA encoding the C-terminal portion, the same vector DNA (pLGC2) was treated with HindIII and BamHI and phosphatased. The pGC605 DNA was treated with HindIII and BamHI and a ca. 402 bp DNA fragment was gel purified and ligated into the HindIII and BamHI treated pLGC2 vector DNA. The recombinant ligation products were transformed into competent cells of *E. coli* strain HW1110. Ampicillin (100 μg/ml) resistant transformants were screened for the required clone by preparation of plasmid DNA, restriction endonuclease analysis with BamHI and HindIII, and agarose gel electrophoresis of the digestion products. One construct with the correct electrophoretic pattern pGC618 was identified. Finally, to reconstruct the intact core streptokinase gene from the two halves, pGC617 DNA was treated with HindIII and BamHI and the ca. 402 bp HindIII-BamHI fragment from pGC618 ligated to it. pGC618 DNA was digested with HindIII and BamHI and a ca. 402 bp HindIII-BamHI DNA fragment was gel purified. pGC617 vector DNA was also treated with HindIII and BamHI and a ca. 402 bp HindIII-BamHI DNA fragment from pGC618 was ligated into it. The ligation products were transformed into competent cells of E. coli strain HW1110. Ampicillin resistant transformants were screened by preparation of plasmid DNA restriction endonuclease analysis with BamHI and HindIII and agarose gel electrophoresis. A correct construct, pGC606, was identified.

EXAMPLE 6

Construction of Expression vectors containing a Thrombin Cleavable Streptokinase-Streptokinase Fusion Gene 1) Construction of a Secretion Vector for the Expression of a Thrombin Cleavable Streptokinase-Streptokinase Fusion A gene encoding an OmpAL streptokinase-streptokinase fusion linked by a thrombin cleavable linker sequence VELQGVVPRG, identical to that at the thrombin cleavage site in Factor XIII, was designed and constructed by site directed mutagenesis and molecular cloning (SEQ ID: NOS:34 and 35). A ca. 1.3 Kb EcoRI-BamHI DNA fragment containing a streptokinase gene was gel purified after treatment of the pUC19SK vector DNA of Preparation 4 with EcoRI and BamHI. A second DNA fragment encoding a streptokinase gene was gel purified after BglII and SalI digestion of the pKJ1 vector DNA of Example 4. A trimolecular ligation was carried out between these two fragments and EcoRI and SalI treated pGC517 vector DNA described in Example 4, section 1A. The recombinant ligation products were transformed into competent cells of E. coli strain HW1110 (laqIq). Ampicillin (100 μg/ml) resistant transformants were screened by preparation of plasmid DNA, restriction endonuclease analysis with EcoRI and SalI and agarose gel electrophoresis. A clone with the correct electrophoretic pattern (pSD93) was identifed. pSD93 contains two tandem copies of the streptokinase gene separated by a sequence containing the bacteriophage lambda gene cII ribosome binding site, and encoding the OmpA signal peptide sequence, the streptokinase signal peptide sequence and the 5' part of the IGF-II sequence from pKJ1. To remove this unwanted intervening sequence and to replace it with the desired thrombin cleavable linker sequence a part of pSD93 was transferred into an M13 mutagenesis vector for mutagenesis. Plasmid pSD93 DNA was digested with HindIII and a ca. 1530 bp DNA fragment gel purified and ligated to HindIII treated and phosphatased replicative form M13mp18 DNA. The recombinant ligation products were transformed into competent cells of E. coli strain JM103 (Example 1). There are two possible fragment orientations in such a construction. The orientation of the clones was determined by preparation of replicative form DNA and analysing the DNA fragments produced after XmnI digestion and agarose gel electrophoresis. One of the clones pSD95 which contained the fragment in an inverted orienation (thus preventing translation readthrough by virtue of fusion to the α-fragment of β-galactosidase expressed from the M13 mutagenesis vector) was used for mutagenesis. Single stranded DNA template was prepared from pSD95 and used for site directed mutagenesis. The primer used was a 63-mer oligonucleotide BB2938: (5'-GATAACC-CTAACGACAAAGTAGAGCTGCAGGGAG-TAGTTCCTCGTGGAATTGCTGGACCTGAG-3') (SEQ ID: NO:36) designed to loop out the gene cII ribosome binding site, the OmpAL IGF-II sequence, the streptokinase signal peptide sequence in pSD95 and to insert a DNA sequence encoding a thrombin cleavable amino acid sequence. Single stranded DNAs were prepared from putative mutant plaques and a correct mutant pGC607 was identified using dideoxy sequence analysis with primer BB2753 (SEQ ID: NO:22) of Example 4. Replicative form DNA of pGC607 was prepared and was digested with HindIII and the ca. 1277 bp HindIII DNA fragment gel purified and ligated to HindIII treated and phosphatased pLGC1 vector DNA of Example 4. The recombinant ligation products were transformed into competent cells of E. coli strain HW1110. Ampicillin resistant transformants were screened by preparation of plasmid DNA, restriction endonuclease analysis using HindIII and agarose gel electrophoresis. This cloning rebuilds the gene encoding a thrombin cleavable streptokinase-streptokinase fusion in an expression vector. A clone (pLGC2) carrying the insert in the sense orientation was identified by dideoxy sequence analysis using primers BB2754 (5'-GCTATCGGTGACACCAT-3') SEQ ID: NO:37 and BB3639 (5'-GCTGCAGGGAGTAGTTC-3') SEQ ID: NO:38. pLGC2 was used for the expression of thrombin cleavable streptokinase-streptokinase fusion protein in E. coli HW1110.

2) Construction of a Vector for the Intracellular Expression of a Thrombin Cleavable Streptokinase-Streptokinase Fusion Gene.

A thrombin cleavable methionyl-streptokinase-streptokinase gene was designed and constructed by molecular cloning. The gene was constructed from the methionyl-streptokinase gene of Example 4 and the HindIII DNA fragment from pGC607 of Example 6, encoding the C-terminal portion of a first streptokinase molecule, a thrombin cleavable linker and an N-terminal portion of a second streptokinase molecule.

Replicative form DNA of pGC607 was prepared and was digested with HindIII and the ca. 1277 bp HindIII DNA fragment was gel purified and ligated to HindIII treated and phosphatased pGC603 vector DNA of Example 4. The recombinant ligation products were transformed into competent cells of E. coli strain HW1110 (lacIq). Ampicillin (100 μg/ml) resistant transformants were screened by preparation of plasmid DNA, restriction endonuclease analysis with HindIII, BamHI and PstI and agarose gel electrophoresis of the digestion products. One construct with the correct electrophoretic pattern pLGC3, was used for the intracellular expression of a thrombin cleavable methionyl-streptokinase-streptokinase fusion protein.

EXAMPLE 7

Construction of a Thrombin Cleavable Core Streptokinase-core Streptokinase Fusion Gene A gene encoding a core methionyl -streptokinase-core streptokinase fusion linked by a thrombin cleavable linker sequence VELQGVVPRG (SEQ ID: NO: 69), identical to that at the thrombin cleavage site in Factor XIII, was designed and constructed by site directed mutagenesis and molecular cloning see SEQ ID: NOS:39 and 40 The core streptokinase-core streptokinase fusion gene was constructed from the core streptokinase monomer gene of Example 5 and a HindIII DNA fragment containing the C-terminal portion of a core streptokinase gene, a thrombin-cleavable linker and an N-terminal portion of a core streptokinase gene. To construct the HindIII DNA fragment containing the appropriate deletions and encoding a thrombin-cleavable linker, pGC607 of Example 6 was used as a template for oligonucleotide directed mutagenesis. A 61-mer oligonucleotide BB3861: (5'-GCTATCATTTAGCC-GTAGAGCTGCAGGGAGTAGTTCCTCGT-GGAAGCCAATTAGTTGTTAG-3') SEQ ID: NO:41 was used to delete the streptokinase amino acids 384 to 414, to reconstruct the thrombin cleavable linker sequence VELQGVVPRG and to delete the first 15 amino acids of the N-terminus of streptokinase. Single stranded DNA from putative mutant plaques was prepared and a correct clone, pGC608, was identified by dideoxy sequence analysis using sequencing primer BB2753 of example 8. Replicative form DNA was prepared from pGC608 and used in further construction.

To construct an intact core methionyl-streptokinase-core-streptokinase fusion, pGC608 DNA was treated with HindIII and the ca. 1140 bp HindIII DNA fragment encoding the C-terminal portion of the core streptokinase molecule, the thrombin cleavable linker sequence and the N-terminal portion of a core streptokinase molecule, was gel purified and ligated to the vector DNA of pGC606 of Example 5 after treatment with HindIII and phosphatase. The recombinant ligation products were transformed into competent cells of E. coli strain HW1110 (lacIq). Ampicillin (100 μg/ml) resistant transformants were analysed by zymography as described in Example 11 below. A correct clone pLGC4, was identified.

EXAMPLE 8

Construction of a Factor Xa-Cleavable Hirudin-IEGR-Streptokinase Fusion Gene A hirudin-streptokinase fusion has been designed in which a full length hirudin molecule is joined to full length streptokinase via an IEGR linker sequence cleavable by factor Xa; see SEQ ID: NOS:42 and 43 The gene encoding the hirudin-streptokinase protein was constructed by site directed mutagenesis and molecular cloning. In order to juxtapose the hirudin and streptokinase genes, the DNA fragments encoding these genes were ligated together. The streptokinase gene from plasmid pKJ2 of Example 4 was isolated by gel purification of a ca. 1.4 kbp DNA fragment after digestion of pKJ2 vector DNA with BglII and BamHI. This DNA fragment contains all of the streptokinase gene together with the DNA encoding the streptokinase signal peptide sequence. This DNA fragment was then ligated to BamHI treated pJK1 DNA of Preparation 2 which contains the hirudin encoding DNA sequence. The recombinant ligation products were transformed into competent cells of E. coli strain HW1110 (lacIq). Ampicillin (100 μg/ml) resistant transformants were screened by preparation of plasmid DNA, restriction endonuclease digestion with HindIII and agarose gel electrophoresis. There are two possible orientations for the insert in this cloning event and correct clones were identified as those which released a ca. 1080 bp DNA fragment after HindIII digestion as analysed on agarose gels. One such clone pJK3, which contains the hirudin gene separated from the streptokinase gene by the streptokinase signal peptide sequence, was used in subsequent manipulations. To create a template for mutagenesis to delete the intervening sequences and to insert the DNA encoding the factor Xa cleavable linker sequence, the hirudin-streptokinase portion of pJK3 was transferred to a mutagenesis vector M13mp18. Plasmid DNA of pJK3 was digested with KpnI and BamHI and the ca. 1490 bp DNA fragment gel purified and ligated to KpnI and BamHI treated M13mp18 replicative form DNA. The recombinant ligation products were transfected into competent cells of E. coli JM103 (Example 1). Single stranded DNA was prepared from putative recombinant plaques and a correct clone pSMD1/100 ( 1.1 ) was identified. To delete the streptokinase signal peptide sequence and to insert the DNA encoding the factor Xa linker sequence single stranded DNA of pSMD1/100 (1.1) was used as a template for mutagenesis with a 46-mer oligonucleotide BB3317: (5'-CACT-CAGGTCCAGCAATTCTACCTTCGATCT-GCAGATATTCTTCTG-3') SEQ ID: NO:44. Single stranded DNA from putative mutant plaques were prepared and a mutant pGC615 was identified by DNA sequence analysis using the sequencing primer BB3510 (5'-CACTATCAGTAGCAT-3') SEQ ID: NO:45. pGC615 contains the C-terminal portion of the hirudin gene linked to the mature streptokinase protein coding sequence. In order to reconstruct the hirudin gene, replicative form DNA of pGC615 was treated with KpnI and BamHI, the ca. 1320 bp DNA fragment gel purified and ligated to KpnI and BamHI treated pJC80 of Preparation 2. The recombinant ligation products were transformed into competent cells of E. coli strain DH5 (Example 4). Ampicillin (100 μg/ml) resistant transformants were screened by preparation of plasmid DNA, restriction endonuclease analysis with KpnI, BamHI and HindIII and agarose gel electrophoresis. A clone with the correct electrophoretic pattern pSMD1/139 was identified. This plasmid contains DNA encoding the complete factor Xa cleavable hirudin-streptokinase fusion molecule.

EXAMPLE 9

Construction of a Vector for the Expression of a Factor Xa Cleavable Hirudin-IEGR-Streptokinase Fusion Molecule To construct a vector for the expression of the hirudin-IEGR-streptokinase gene, DNA of pSMD1/139 of Example 8 was treated with HindIII and a ca. 963 bp DNA fragment encoding part of the yeast alpha factor secretion signal, all of hirudin, the factor Xa linker and the 5' part of streptokinase as far as the internal HindIII site in the streptokinase sequence was gel purified. This fragment was then ligated to HindIII treated and phosphatased DNA of pSMD1/119 of Example 4. The recombinant ligation products were transformed into competent cells of E. coli strain DH5 (Example 4). Ampicillin resistant transformants were screened by preparation of plasmid DNA, restriction endonuclease digestion with KpnI and BamHI and agarose gel electrophoresis. It is possible to obtain two orientations of the HindIII insert and one clone in the correct orientation pSMD1/146 was identified as releasing a ca. 1311 bp fragment after KpnI and BamHI treatment. pSMD1/146 contains the full length fusion gene under the control of the regulatable PAL promoter described in Preparation 2, and has been designed for the regulated expression and secretion of the factor Xa-cleavable hirudin-streptokinase fusion protein. pSMD1/146 plasmid DNA was prepared and used to transform yeast strain BJ2168 (Preparation 3) according to the method of Sherman, F. et al., (Methods in Yeast Genetics, Cold Spring Harbor Laboratory (1986)).

EXAMPLE 10

Construction of a Factor Xa Cleavable Streptokinase-IEGR-Hirudin Fusion Gene and its Expression Vector A gene encoding a streptokinase-hirudin fusion protein linked via a Factor Xa cleavage site (IEGR) was constructed by site-directed mutagenesis and molecular cloning SEQ ID: NOS:46 and 47 In order to juxtapose the streptokinase and hirudin genes, DNA fragments encoding these two gene were ligated together. The pUC19SK vector DNA of Preparation 4 was prepared and treated with HindIII and BamHI and the ca. 500 bp DNA fragment containing the 3' end of the streptokinase gene was gel purified. This fragment was ligated to M13mp19 replicative form DNA treated with HindIII and BamHI. The recombinant ligation mixture was transfected into competent cells of E. coli strain JM103 (Example 1). Single stranded DNA was prepared from putative recombinant plaques and the required clone M13JK1 identifed by dideoxy sequence analysis using the M13 universal sequencing primer (SEQ ID: NO:11, Example 1). M13JK1 contains the C-terminal portion of the streptokinase gene. The α-factor hirudin gene was then cloned into M13JK1 to juxtapose both sequences. Plasmid DNA of pJK1 of Preparation 2 was digested with BqlII and BamHI and a ca. 465bp DNA fragment encoding the α-factor hirudin fusion was gel purified. This DNA fragment was then ligated to BamHI treated replicative form DNA of M13JK1. The recombinant ligation products were transfected into competent cells of E. coli strain JM103. Single stranded DNA from putative recombinant plaques were prepared and a correct clone SMD1/100.3 identified by dideoxy sequence analysis using M13 universal sequencing primer (SEQ ID: NO:11, Example 1. SMD1/100.3 contains the C-terminal portion of the streptokinase gene and the complete hirudin gene separated by the α-factor encoding sequence described in Preparation 2. In order to delete this sequence and replace it with a factor Xa-cleavable linker sequence, SMD1/100.3 was used as a template for site-directed mutagenesis. Single stranded DNA of SMD1/100.3 was prepared and used for mutagenesis using a 47-mer mutagenesis primer BB3318: (5'-TCGGTGTAAACAACTCTTCTACCTT-CGATTTTGTCGTTAGGGTTATC-3") (SEQ ID: NO:49). Single stranded DNA from putative mutant plaques were prepared and the required mutation pGC616 identified by dideoxy sequence analysis using the sequencing primer BB2018: (5'-GCGGCTTTGGGGTACCTTCACCAGT-GACACATTGG-3') (SEQ ID: NO:57). pGC616 contains an additional mutation inadvertently introduced by the mutagenesis procedure. This was corrected by a further mutagenic step. Single stranded DNA of pGC616 was prepared and used as a template for mutagenesis with a 21-mer oligonucleotide BB3623 (5'-GTGTAAACAACTCTACCTTCG-3') (SEQ ID: NO:49). Single stranded DNA from putative mutant plaques was prepared and a correct clone pGC620 identified by dideoxy sequence analysis with the sequencing primer BB2018 (SEQ ID: NO:57). pGC620 contains the C-terminal portion of the streptokinase gene and the complete hirudin gene fused via DNA encoding a factor Xa-cleavable linker. The intact factor Xa-cleavable streptokinase-hirudin fusion gene was reconstructed in two steps. The C-terminal streptokinase-hirudin sequence from pGC620 was cloned into the yeast expression vector pSW6 of Preparation 2 and then the N-terminal portion of streptokinase was cloned into the new vector to create the full length streptokinase-hirudin fusion gene.

Replicative form DNA of pGC620 was treated with HindIII and BamHI and a ca. 710 bp HindIII-BamHI DNA fragment encoding the 3' end of streptokinase, the intervening factor Xa-cleavable linker DNA sequence and all of the hirudin gene was gel purified. This ca. 710 bp DNA fragment was ligated to pSW6 of Preparation 2 digested with HindIII and BamHI. The recombinant ligation products were transformed into competent cells of E. coli strain DH5 (Example 4). Ampicillin (100 μg/ml) resistant transformants were screened by preparation of plasmid DNA, restriction endonuclease analysis using HindIII and BamHI and agarose gel electrophoresis. A clone with the correct electrophoretic pattern pSMD1/143 was identified. The intact fusion gene was then constructed by cloning the N-terminal portion of α-factor-streptokinase into pSMD1/143. Replicative form DNA of pGC614 of Example 4 was treated with HindIII and the ca. 750 bp DNA fragment containing the N-terminal portion of α-factor-streptokinase gel purified and ligated to HindIII treated and phosphatased pSMD1/143 vector DNA. The recombinant ligation products were transformed into competent cells of E. coli strain DH5. Ampicillin (100 μg/ml) resistant transformants were screened by preparation of plasmid DNA, restriction endonuclease digestion with DraI and agarose gel electrophoresis. A clone in the correct orientation pSMD1/159 was identified as giving rise to 4 fragments of sizes of about 4750 bp, 2140 bp, 1526 bp, and 692 bp after DraI digestion. pSMD1/159 was used for the expression of the factor Xa-cleavable streptokinase-hirudin fusion protein. pSMD1/159 plasmid DNA was prepared and used to transform yeast strain BJ2168 (Preparation 5) according to the method of Sherman, F. et al., (Methods in Yeast Genetics, Cold Spring Harbour Laboratory (1986)).

EXAMPLE 11

Expression of Monomer Streptokinase Constructs

Expression

Competent cells of E. coli strain JM103 (Example 1) were transformed with DNA of the streptokinase expression vectors of Examples 4, 5, 6 and 7. The lacIq gene in the expression host is desirable to repress transcription from the tac promoter used in all of the E. coli expression constructs. All media for the growth of recombinant E. coli strains were as described in Maniatis et al. Using 1 liter shake flasks, cultures of recombinant *E. coli* containing streptokinase expression vectors were grown in 250 ml batches of 2TY medium containing 100 μg/ml of carbenicillin at 37° C. in an orbital shaker. The optical density of the cultures were monitored at 600 nm. When the culture reached an OD 600 nm of 0.5, expression from the tac promoter was induced by the addition of isopropyl-β-D-thiogalactoside (IPTG) to a final concentration of 1 mM. After growth for 30 to 240 min the cells were harvested by centrifugation. SDS-PAGE Separation The ability of the recombinant *E. coli* cells to express streptokinase was assayed using zymography. The quantity and molecular weight of streptokinase activity of an *E. coli* culture was estimated by the following protocol. A 1 ml aliquot of the culture was removed, the cells were harvested by centrifugation (14 000×g) for 5 mins and resuspended in 200 μl of loading buffer (125 mM Tris.HCl pH 6.8, 10% glycerol (w/v), 0.01% (w/v) bromophenol blue, 1% (v/v) 2-mercaptoethanol, 6M urea). An aliquot of this mixture was applied to an SDS-PAGE gel and the protein separated by electrophoresis. The quantity of protein loaded onto the gel was varied by altering the size of the aliquot according to the optical density of the culture upon harvesting. Generally, 10 μl of the mixture from a culture of OD 600 nm of 1.0 was used for each lane.

Zymography

After electrophoresis the polyacrylamide gel was washed in 2% (w/v) Triton X-100 (3×20 mins) followed by water washes (3×20 mins) to remove the SDS and allow renaturation of the streptokinase molecule.

The washed SDS-PAGE gel was then overlayed with an agarose mixture prepared as follows. 200 mg of agarose was dissolved in 18 ml distilled and deionised water (dH2O) and allowed to cool to 55°-60° C. To this 200 mg of MARVEL (trade mark of Premier Brands, U.K. Ltd. P.O. Box 171, Birmingham, B30 2NA, U.K.) (casein) dissolved in 2 ml of dH2O, ml of 1M Tris.HCl pH 8.0 and 600 μl of 5M NaCl were added. Just before pouring over the washed SDS-PAGE gel, 700 μl of plasminogen at 300 μg/ml (Sigma P-7397 10 mg/ml in 50 mM Tris. HCl pH 7.5) was added and mixed thoroughly. The mixture was poured over the gel and once set was incubated at 37° C. for 2 hours when it could be inspected. Plasminogen activator activity (streptokinase activity) was detected by plasmin digestion of the opaque casein containing overlay which produced clear zones. The position of the zones on the gel was directly related to the size of the active molecules.

Figure 5:
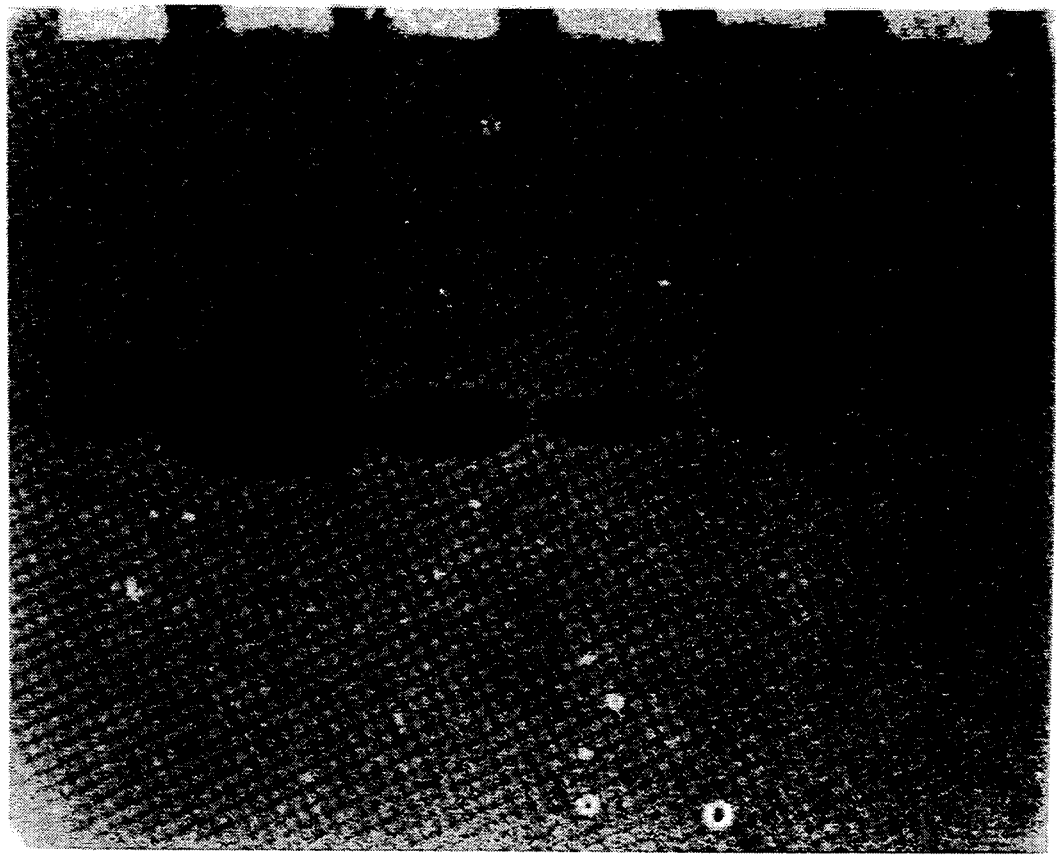
FIG. 5 shows a zymograph of *E. coli* strains expressing streptokinase activity (Example 11)

The recombinant *E. coli* JM103 strains containing monomer streptokinase expression vectors pKJ2 of Example 4 and pLGC1 of Example 4 both expressed streptokinase activity with a molecular weight of approximately 47 kDa (FIG. 5).

EXAMPLE 12

Expression of a Thrombin Cleavable Streptokinase-Streptokinase Fusion Protein.

A recombinant *E. coli* HW1110 (lacIq) strain (Example 1) containing pLGC2 of Example 6, the thrombin cleavable streptokinase- streptokinase fusion gene, was expressed and analysed according to the expression and zymography protocols of Example 11. The *E. coli* JM103/pLGC2 strain expressed streptokinase activities of several molecular weights, predominantly of 110 kDa and 47 kDa (FIG. 5). Cleavage analysis is described in Example 13 below.

EXAMPLE 13

Cleavage of the Thrombin Cleavable Streptokinase-streptokinase Fusion Protein by Thrombin Using 1 liter shake flasks, a 3 liter culture of *E. coli* JM103 (Example 1) containing pLGC2 of Example 6 was grown in 500 ml batches in 2TY medium containing 100 mcg/ml carbenicillin at 37° C. with vigorous shaking in an orbital shaker. When the optical density of the cultures reached an O.D. 600 nm of 0.5 the expression of the streptokinase-streptokinase fusion protein was induced by the addition of IPTG to a final concentration of 1 mM. The cultures were incubated at 37° C. with vigorous shaking for a further 4 hours when they were harvested by centrifugation at 8,000 r.p.m. for 10 mins. The cells were resuspended in 10 ml of ice cold TS buffer (10 mM Tris.HCl pH 7.5, 20% (w/v) sucrose). 348 μl of 0.5M EDTA was added and the mixture incubated on ice for 10 mins. The cells were harvested by centrifugation at 8,000 r.p.m. for 5 min at 4° C. and the supernatant discarded. The cells were resuspended in 6.25 ml of ice cold sterile H2O and incubated on ice for 10 min. The cells were harvested by centrifugation at 8,000 rpm. for 5 min at 15,000 g for 30 min at 4° C. and the supernatant discarded. The cells were resuspended in 48 ml of ARG buffer (20 mM Tris.HCl pH 7.5, 10 mM MgCl2, 10 mM 2-b-mercaptoethanol, 0.5 mM phenylmethyl sulphonyl fluoride, 12 mcM N-tosyl-L-phenylalanine chloromethyl ketone) and sonicated on ice (6×30 sec. bursts on maximum power, MSE SONI-PREP 150 (trade mark)). The cell sonicate was centrifuged at 15,000 g for 30 min at 4° C. The supernatant was decanted and assayed for streptokinase activity using the S2251 (KabiVitrum Ltd, KabiVitrum House, Riverside Way, Uxbridge, Middlesex, UB8 2YF, UK) chromogenic assay for the streptokinase activation of plasminogen. S2251 is a specific tripeptide chromogenic substrate for plasmin. 25 μl of 0.1M Tris. HCl pH 8.0 was placed in wells 2 to 12 of 96 well plates. Aliquots of the sample (25 μl) were placed in wells 1 and 2, and two-fold dilutions made by mixing and pipetting from wells 2 to 3, 3 to 4 and so on to well 11. A 100 μl aliquot of a plasminogen/S2251 mixture (40 μl plasminogen 300 μg/ml, 220 μl S2251 1 mg/ml, 1.04 ml 0.1M Tris. HCl pH 7.5) was added to each well and the plate incubated at 37° C. for 30 min. The reaction was terminated by the addition of 50 mcl of 0.5M acetic acid. The absorbance was read at 405 nM using an automatic plate reader. Quantification was performed by comparison with a standard streptokinase preparation. The analysis showed that the supernatant contained approximately 2560 u/ml of streptokinase activity.

Solid ammonium sulphate was slowly added to the supernatant to 15% saturation (4.03 g) and allowed to dissolve for 15 min at room temperature. The mixture was then centrifuged for 30 min at 15,000 g at room temperature. The supernatant was decanted and additional solid ammonium sulphate was added to 40% saturation (7.27 g), and allowed to dissolve. The mixture was centrifuged for 30 min at 15,000 g at room temperature and the supernatant discarded. The pelleted protein (the 15–40% cut), was resuspended in 10 ml of ARG buffer. A portion of the 15–40% cut was assayed using the S2251 chromgenic assay and was found to contain 18,432 u/ml of streptokinase activity.

Figure 6:
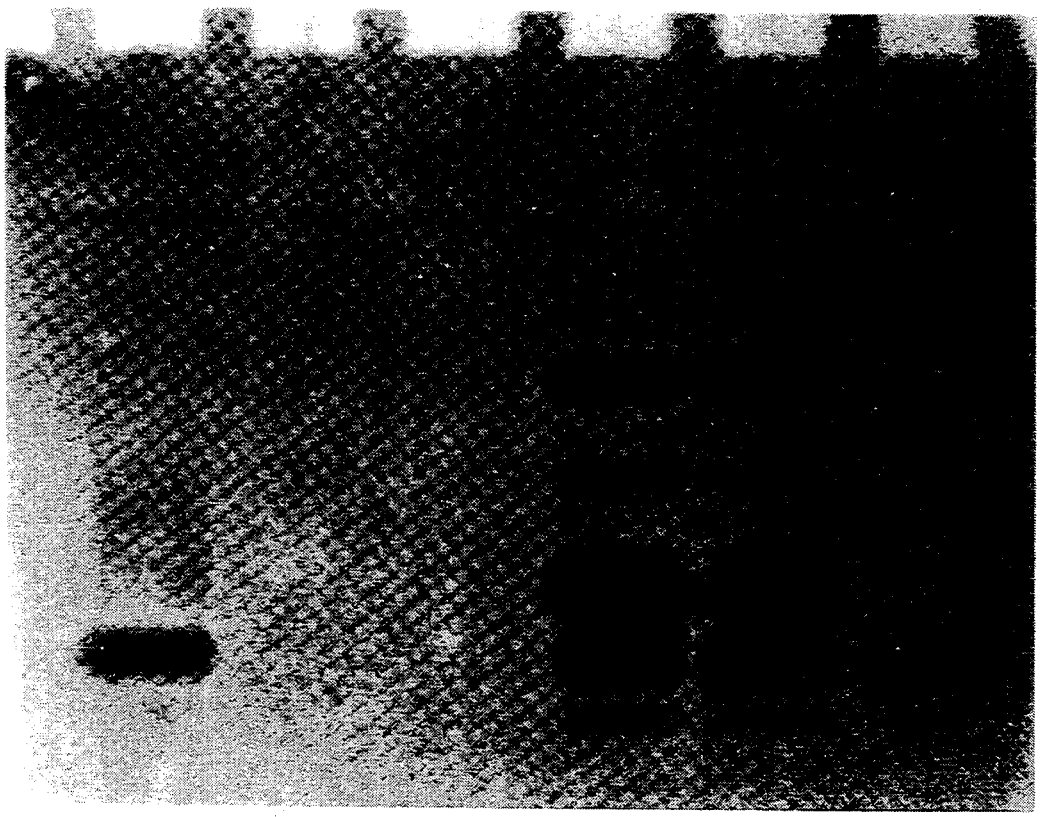
FIG. 6 shows a zymograph demonstrating cleavage of a streptokinase-streptokinase fusion protein by thrombin (Example 13).

The ability of thrombin to cleave the streptokinase-streptokinase fusion protein at the thrombin cleavable linker was assessed by an in vitro cleavage assay and zymography. A 5 µl aliquot of the 15–40% cut was mixed with 45 µl of ARG buffer to dilute the protein ten-fold. 10 µl of this mixture was incubated with 5 u/ml of thrombin in a final volume of 50 µl at 37° C. for 14 hours. Aliquots (10 µl) of the thrombin cleavage reactions were analysed by zymography according to the method of Example 11. The results are shown in FIG. 6. The streptokinase-streptokinase fusion protein (Mr 110 kDa), was quantitatively cleaved whilst the lower molecular weight streptokinase activity (Mr 47 kDa) was not cleaved by thrombin. Thus the streptokinase-streptokinase fusion protein is cleavable by thrombin.

EXAMPLE 14

Expression of a Factor Xa Cleavable Streptokinase-IEGR-hirudin Fusion Gene

Plasmid expression vector pSMD1/159 of Example 10 was transferred into yeast (*S. cerevisiae*) strain BJ2168 according to the method of Preparation 3. Using 500 ml shake flasks, cultures of yeast containing pSMD1/159 were grown in 100 ml batches of 0.67% synthetic complete medium yeast nitrogen base, with amino acids minus leucine and 1% glucose as a carbon source. After overnight growth at 30° C., the cells were harvested by centrifugation at 3,000 rpm for 10 min and resuspended in the same synthetic complete medium except having 1% galactose and 0.2% glucose as the carbon source and the addition of sodium phosphate (to 50 mM) pH 7.2. This induces the expression of the streptokinase-hirudin fusion gene from the hybrid PGK promoter. Cells were grown in the induction medium for 3 days. After this period, the supernatant was harvested by centrifugation. The broth was assayed for both streptokinase activity according to the S2251 assay procedure of Example 13 and hirudin activity according to the thrombin inhibition assay of Example 2. Both activities were detected and secreted to the medium.

EXAMPLE 15

Expression of a Factor Xa Cleavable Hirudin-IEGR-Streptokinase Fusion Gene

Plasmid expression vector pSMD1/146 of Example 9 was transferred into yeast (*S. cerevisiae*) strain BJ2168 according to the method of Preparation 3. The culture was incubated, expressed, harvested and the hirudin and streptokinase activities assayed according to the methods of Examples 2 and 13. Both streptokinase and hirudin activities were detected and secreted to the medium.

---

We claim:

1. A non-naturally occurring fusion protein suitable for use as a selectively acting fibrinolytic or anti-thrombotic agent comprising a first sequence, a second sequence, and a Factor Xa cleavable linker sequence, wherein the Factor Xa cleavable linker sequence is IEGR (SEQ ID: NO: 71) and the first sequence and second sequence are chosen from the group consisting of streptokinase, hirudin and their conservatively substituted analogues, provided that when either the first or second sequence is hirudin or its conservatively substituted analogue the other is streptokinase or its conservatively substituted analogue.

* * * * *

SEQUENCE LISTING ( 1 ) GENERAL INFORMATION:

( i i i ) NUMBER OF SEQUENCES: 73

( 2 ) INFORMATION FOR SEQ ID NO:1:

( i ) SEQUENCE CHARACTERISTICS:
        ( A ) LENGTH: 201 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..201
        ( D ) OTHER INFORMATION: /note="hirudin type HV-1 gene"

( i x ) FEATURE:
        ( A ) NAME/KEY: CDS
        ( B ) LOCATION: 1..195

( i x ) FEATURE:
        ( A ) NAME/KEY: mat_peptide
        ( B ) LOCATION: 1..195

( x i ) SEQUENCE DESCRIPTION: SEQ ID NO:1:

```
GTT  GTT  TAC  ACC  GAC  TGT  ACT  GAA  TCC  GGA  CAA  AAC  CTG  TGT  TTG  TGT        48
Val  Val  Tyr  Thr  Asp  Cys  Thr  Glu  Ser  Gly  Gln  Asn  Leu  Cys  Leu  Cys
 1              5                        10                       15

GAG  GGT  TCT  AAC  GTC  TGT  GGT  CAG  GGT  AAC  AAA  TGC  ATC  CTG  GGT  TCC        96
Glu  Gly  Ser  Asn  Val  Cys  Gly  Gln  Gly  Asn  Lys  Cys  Ile  Leu  Gly  Ser
              20                        25                       30

GAC  GGT  GAA  AAG  AAC  CAA  TGT  GTC  ACT  GGT  GAA  GGT  ACC  CCA  AAG  CCG       144
Asp  Gly  Glu  Lys  Asn  Gln  Cys  Val  Thr  Gly  Glu  Gly  Thr  Pro  Lys  Pro
              35                        40                       45

CAG  TCC  CAC  AAC  GAT  GGA  GAT  TTC  GAA  GAA  ATC  CCA  GAA  GAA  TAT  CTG       192
Gln  Ser  His  Asn  Asp  Gly  Asp  Phe  Glu  Glu  Ile  Pro  Glu  Glu  Tyr  Leu
```

CAG TAATAG                                                                            201
Gln
65

(2) INFORMATION FOR SEQ ID NO:2:

(i) SEQUENCE CHARACTERISTICS:
       (A) LENGTH: 65 amino acids
       (B) TYPE: amino acid
       (D) TOPOLOGY: linear (ii) MOLECULE TYPE: protein (xi) SEQUENCE DESCRIPTION: SEQ ID NO:2:

Val Val Tyr Thr Asp Cys Thr Glu Ser Gly Gln Asn Leu Cys Leu Cys
 1           5                  10                 15

Glu Gly Ser Asn Val Cys Gly Gln Gly Asn Lys Cys Ile Leu Gly Ser
            20                  25                 30

Asp Gly Glu Lys Asn Gln Cys Val Thr Gly Glu Gly Thr Pro Lys Pro
        35                  40                 45

Gln Ser His Asn Asp Gly Asp Phe Glu Glu Ile Pro Glu Glu Tyr Leu
    50                  55                 60

Gln
65

(2) INFORMATION FOR SEQ ID NO:3:

(i) SEQUENCE CHARACTERISTICS:
       (A) LENGTH: 19 base pairs
       (B) TYPE: nucleic acid
       (C) STRANDEDNESS: single
       (D) TOPOLOGY: linear (ii) MOLECULE TYPE: cDNA (ix) FEATURE:
       (A) NAME/KEY: misc_feature
       (B) LOCATION: 1..19
       (D) OTHER INFORMATION: /note="oligonucleotide universal
            primer for pUC19"

(xi) SEQUENCE DESCRIPTION: SEQ ID NO:3:

CAGGGTTTTC CCAGTCACG                                                                   19

(2) INFORMATION FOR SEQ ID NO:4:

(i) SEQUENCE CHARACTERISTICS:
       (A) LENGTH: 7859 base pairs
       (B) TYPE: nucleic acid
       (C) STRANDEDNESS: single
       (D) TOPOLOGY: circular (ii) MOLECULE TYPE: cDNA (ix) FEATURE:
       (A) NAME/KEY: misc_feature
       (B) LOCATION: 1..7859
       (D) OTHER INFORMATION: /note="sequence of plasmid pSW6"

(xi) SEQUENCE DESCRIPTION: SEQ ID NO:4:

TTCCCATGTC TCTACTGGTG GTGGTGCTTC TTTGGAATTA TTGGAAGGTA AGGAATTGCC      60

AGGTGTTGCT TTCTTATCCG AAAAGAAATA AATTGAATTG AATTGAAATC GATAGATCAA     120

TTTTTTTCTT TTCTCTTTCC CCATCCTTTA CGCTAAAATA ATAGTTTATT TTATTTTTTG     180

AATATTTTTT ATTTATATAC GTATATATAG ACTATTATTT ACTTTTAATA GATTATTAAG     240

ATTTTTATTA AAAAAAAATT CGTCCCTCTT TTTAATGCCT TTATGCAGT  TTTTTTTTCC     300

```
CATTCGATAT  TTCTATGTTC  GGGTTTCAGC  GTATTTTAAG  TTTAATAACT  CGAAAATTCT    360
GCGTTTCGAA  AAAGCTCTGC  ATTAATGAAT  CGGCCAACGC  GCGGGGAGAG  GCGGTTTGCG    420
TATTGGGCGC  TCTTCCGCTT  CCTCGCTCAC  TGACTCGCTG  CGCTCGGTCG  TTCGGCTGCG    480
GCGAGCGGTA  TCAGCTCACT  CAAAGGCGGT  AATACGGTTA  TCCACAGAAT  CAGGGGATAA    540
CGCAGGAAAG  AACATGTGAG  CAAAAGGCCA  GCAAAAGGCC  AGGAACCGTA  AAAAGGCCGC    600
GTTGCTGGCG  TTTTTCCATA  GGCTCCGCCC  CCTGACGAG   CATCACAAAA  ATCGACGCTC    660
AAGTCAGAGG  TGGCGAAACC  CGACAGGACT  ATAAAGATAC  CAGGCGTTTC  CCCCTGGAAG    720
CTCCCTCGTG  CGCTCTCCTG  TTCCGACCCT  GCCGCTTACC  GGATACCTGT  CCGCCTTTCT    780
CCCTTCGGGA  AGCGTGGCGC  TTTCTCATAG  CTCACGCTGT  AGGTATCTCA  GTTCGGTGTA    840
GGTCGTTCGC  TCCAAGCTGG  GCTGTGTGCA  CGAACCCCCC  GTTCAGCCCG  ACCGCTGCGC    900
CTTATCCGGT  AACTATCGTC  TTGAGTCCAA  CCCGGTAAGA  CACGACTTAT  CGCCACTGGC    960
AGCAGCCACT  GGTAACAGGA  TTAGCAGAGC  GAGGTATGTA  GGCGGTGCTA  CAGAGTTCTT   1020
GAAGTGGTGG  CCTAACTACG  GCTACACTAG  AAGGACAGTA  TTTGGTATCT  GCGCTCTGCT   1080
GAAGCCAGTT  ACCTTCGGAA  AAAGAGTTGG  TAGCTCTTGA  TCCGGCAAAC  AAACCACCGC   1140
TGGTAGCGGT  GGTTTTTTTG  TTTGCAAGCA  GCAGATTACG  CGCAGAAAAA  AAGGATCTCA   1200
AGAAGATCCT  TTGATCTTTT  CTACGGGGTC  TGACGCTCAG  TGGAACGAAA  ACTCACGTTA   1260
AGGGATTTTG  GTCATGAGAT  TATCAAAAAG  GATCTTCACC  TAGATCCTTT  TAAATTAAAA   1320
ATGAAGTTTT  AAATCAATCT  AAAGTATATA  TGAGTAAACT  TGGTCTGACA  GTTACCAATG   1380
CTTAATCAGT  GAGGCACCTA  TCTCAGCGAT  CTGTCTATTT  CGTTCATCCA  TAGTTGCCTG   1440
ACTCCCCGTC  GTGTAGATAA  CTACGATACG  GGAGGGCTTA  CCATCTGGCC  CCAGTGCTGC   1500
AATGATACCG  CGAGACCCAC  GCTCACCGGC  TCCAGATTTA  TCAGCAATAA  ACCAGCCAGC   1560
CGGAAGGGCC  GAGCGCAGAA  GTGGTCCTGC  AACTTTATCC  GCCTCCATCC  AGTCTATTAA   1620
TTGTTGCCGG  GAAGCTAGAG  TAAGTAGTTC  GCCAGTTAAT  AGTTTGCGCA  ACGTTGTTGC   1680
CATTGCTACA  GGCATCGTGG  TGTCACGCTC  GTCGTTTGGT  ATGGCTTCAT  TCAGCTCCGG   1740
TTCCCAACGA  TCAAGGCGAG  TTACATGATC  CCCCATGTTG  TGCAAAAAAG  CGGTTAGCTC   1800
CTTCGGTCCT  CCGATCGTTG  TCAGAAGTAA  GTTGGCCGCA  GTGTTATCAC  TCATGGTTAT   1860
GGCAGCACTG  CATAATTCTC  TTACTGTCAT  GCCATCCGTA  AGATGCTTTT  CTGTGACTGG   1920
TGAGTACTCA  ACCAAGTCAT  TCTGAGAATA  GTGTATGCGG  CGACCGAGTT  GCTCTTGCCC   1980
GGCGTCAACA  CGGGATAATA  CCGCGCCACA  TAGCAGAACT  TTAAAAGTGC  TCATCATTGG   2040
AAAACGTTCT  TCGGGGCGAA  AACTCTCAAG  GATCTTACCG  CTGTTGAGAT  CCAGTTCGAT   2100
GTAACCCACT  CGTGCACCCA  ACTGATCTTC  AGCATCTTTT  ACTTTCACCA  GCGTTTCTGG   2160
GTGAGCAAAA  ACAGGAAGGC  AAAATGCCGC  AAAAAAGGGA  ATAAGGGCGA  CACGGAAATG   2220
TTGAATACTC  ATACTCTTCC  TTTTTCAATA  TTATTGAAGC  ATTTATCAGG  GTTATTGTCT   2280
CATGAGCGGA  TACATATTTG  AATGTATTTA  GAAAAATAAA  CAAATAGGGG  TTCCGCGCAC   2340
ATTTCCCCGA  AAAGTGCCAC  CTGACGTCTA  AGAAACCATT  ATTATCATGA  CATTAACCTA   2400
TAAAAATAGG  CGTATCACGA  GGCCCTTTCG  TCTTCAAGAA  TTCTGAACCA  GTCCTAAAAC   2460
GAGTAAATAG  GACCGGCAAT  TCTTCAAGCA  ATAAACAGGA  ATACCAATTA  TTAAAAGATA   2520
ACTTAGTCAG  ATCGTACAAT  AAAGCTAGCT  TTGAAGAAAA  ATGCGCCTTA  TTCAATCTTT   2580
GCTATAAAAA  ATGGCCCAAA  ATCTCACATT  GGAAGACATT  TGATGACCTC  ATTTCTTTCA   2640
ATGAAGGGCC  TAACGGAGTT  GACTAATGTT  GTGGGAAATT  GGAGCGATAA  GCGTGCTTCT   2700
GCCGTGGCCA  GGACAACGTA  TACTCATCAG  ATAACAGCAA  TACCTGATCA  CTACTTCGCA   2760
```

```
CTAGTTTCTC GGTACTATGC ATATGATCCA ATATCAAAGG AAATGATAGC ATTGAAGGAT    2820
GAGACTAATC CAATTGAGGA GTGGCAGCAT ATAGAACAGC TAAAGGGTAG TGCTGAAGGA    2880
AGCATACGAT ACCCCGCATG GAATGGGATA ATATCACAGG AGGTACTAGA CTACCTTTCA    2940
TCCTACATAA ATAGACGCAT ATAAGTACGC ATTTAAGCAT AAACACGCAC TATGCCGTTC    3000
TTCTCATGTA TATATATATA CAGGCAACAC GCAGATATAG GTGCGACGTG AACAGTGAGC    3060
TGTATGTGCG CAGCTCGCGT TGCATTTTCG GAAGCGCTCG TTTTCGGAAA CGCTTTGAAG    3120
TTCCTATTCC GAAGTTCCTA TTCTCTAGAA AGTATAGGAA CTTCAGAGCG CTTTTGAAAA    3180
CCAAAAGCGC TCTGAAGACG CACTTTCAAA AACCAAAAA CGCACCGGAC TGTAACGAGC     3240
TACTAAAATA TTGCGAATAC CGCTTCCACA ACATTGCTC AAAAGTATCT CTTTGCTATA     3300
TATCTCTGTG CTATATCCCT ATATAACCTA CCCATCCACC TTTCGCTCCT GAACTTGCA     3360
TCTAAACTCG ACCTCTACAT TTTTTATGTT TATCTCTAGT ATTACTCTTT AGACAAAAA    3420
ATTGTAGTAA GAACTATTCA TAGAGTGAAT CGAAACAAT ACGAAAATGT AAACATTTCC     3480
TATACGTAGT ATATAGAGAC AAAATAGAAG AAACCGTTCA TAATTTTCTG ACCAATGAAG    3540
AATCATCAAC GCTATCACTT TCTGTTCACA AGTATGCGC AATCCACATC GGTATAGAAT     3600
ATAATCGGGG ATGCCTTTAT CTTGAAAAAA TGCACCCGCA GCTTCGCTAG TAATCAGTAA    3660
ACGCGGGAAG TGGAGTCAGG CTTTTTTTAT GGAAGAGAAA ATAGACACCA AGTAGCCTT    3720
CTTCTAACCT TAACGGACCT ACAGTGCAAA AAGTTATCAA GAGACTGCAT TATAGAGCGC    3780
ACAAGGAGA AAAAAGTAA TCTAAGATGC TTTGTTAGAA AAATAGCGCT CTCGGATGC      3840
ATTTTTGTAG AACAAAAAG AAGTATAGAT TCTTTGTTGG TAAAATAGCG CTCTCGCGTT     3900
GCATTTCTGT TCTGTAAAAA TGCAGCTCAG ATTCTTTGTT TGAAAAATTA GCGCTCTCGC    3960
GTTGCATTTT TGTTTTACAA AAATGAAGCA CAGATTCTTC GTTGGTAAAA TAGCGCTTTC    4020
GCGTTGCATT TCTGTTCTGT AAAAATGCAG CTCAGATTCT TTGTTGAAA AATTAGCGCT     4080
CTCGCGTTGC ATTTTTGTTC TACAAAATGA AGCACAGATG CTTCGTTAAC AAAGATATGC    4140
TATTGAAGTG CAAGATGGAA ACGCAGAAAA TGAACCGGGG ATGCGACGTG CAAGATTACC    4200
TATGCAATAG ATGCAATAGT TTCTCCAGGA ACCGAAATAC ATACATTGTC TTCCGTAAAG    4260
CGCTAGACTA TATATTATTA TACAGGTTCA AATATACTAT CTGTTTCAGG GAAAACTCCC    4320
AGGTTCGGAT GTTCAAAATT CAATGATGGG TAACAAGTAC GATCGTAAAT CTGTAAAACA    4380
GTTTGTCGGA TATTAGGCTG TATCTCCTCA AAGCGTATTC GAATATCATT GAGAAGCTGC    4440
ATTTTTTTTT TTTTTATAT ATATTTCAAG GATATACCAT TGTAATGCCT GCCCCTAAGA     4500
AGATCGTCGT TTTGCCAGGT GACCACGTTG GTCAAGAAAT CACAGCCGAA GCCATTAAGG    4560
TTCTTAAAGC TATTTCTGAT GTTCGTTCCA ATGTCAAGTT CGATTTCGAA AATCATTTAA    4620
TTGGTGGTGC TGCTATCGAT GCTACAGGTG TTCCACTTCC AGATGAGGCG CTGGAAGCCT    4680
CCAAGAAGGC TGATGCCGTT TGTTAGGTG CTGTGGGTGG TCCTAAATGG GGTACCGGTA     4740
GTGTTAGACC TGAACAAGGT TTACTAAAAA TCCGTAAAGA ACTTCAATTG TACGCCAACT    4800
TAAGACCATG TAACTTTGCA TCCGACTCTC TTTTAGACTT ATCTCCAATC AAGCCACAAT    4860
TTGCTAAAGG TACTGACTTC GTTGTTGTTA GAGAATTAGT GGGAGGTATT TACTTTGGTA    4920
AGAGAAAGGA AGACGATGGT GATGGTGTCG CTTGGGATAG TGAACAATAC ACCGTTCCAG    4980
AAGTGCAAAG AATCACAAGA ATGGCCGCTT TCATGGCCCT ACAACATGAG CCACCATTGC    5040
CTATTTGGTC CTTGGATAAA GCTAATGTTT TGGCCTCTTC AAGATTATGG AGAAAAACTG    5100
TGGAGGAAAC CATCAAGAAC GAATTCCCTA CATTGAAAGT TCAACATCAA TTGATTGATT    5160
CTGCCGCCAT GATCCTAGTT AAGAACCCAA CCCACCTAAA TGGTATTATA ATCACCAGCA    5220
```

| | | | | | |
|---|---|---|---|---|---|
| ACATGTTTGG | TGATATCATC | TCCGATGAAG | CCTCCGTTAT | CCCAGGCTCC | TTGGGTTTGT | 5280
| TGCCATCTGC | GTCCTTGGCC | TCTTTGCCAG | ACAAGAACAC | CGCATTTGGT | TTGTACGAAC | 5340
| CATGCCATGG | TTCCGCTCCA | GATTGCCAA | AGAATAAGGT | CAACCCTATC | GCCACTATCT | 5400
| TGTCTGCTGC | AATGATGTTG | AAATTGTCAT | TGAACTTGCC | TGAAGAAGGT | AAAGCCATTG | 5460
| AAGATGCAGT | TAAAAAGGTT | TTGGATGCAG | GTATCAGAAC | TGGTGATTTA | GGTGGTTCCA | 5520
| ACAGTACCAC | CGAAGTCGGT | GATGCTGTCG | CCGAAGAAGT | TAAGAAAATC | CTTGCTTAAA | 5580
| AAGATTCTCT | TTTTTTATGA | TATTTGTACA | AAAAAAAAAA | AAAAAAAAAA | AAAAAAAAA | 5640
| AAAAAAAAAA | AAAAAAAAAA | AAAATGCAGC | GTCACATCGG | ATAATAATGA | TGGCAGCCAT | 5700
| TGTAGAAGTG | CCTTTTGCAT | TTCTAGTCTC | TTTCTCGGTC | TAGCTAGTTT | TACTACATCG | 5760
| CGAAGATAGA | ATCTTAGATC | ACACTGCCTT | TGCTGAGCTG | GATCAATAGA | GTAACAAAAG | 5820
| AGTGGTAAGG | CCTCGTTAAA | GGACAAGGAC | CTGAGCGGAA | GTGTATCGTA | CAGTAGACGG | 5880
| AGTATACTAG | TATAGTCTAT | AGTCCGTGGA | ATTCTCATGT | TTGACAGCTT | ATCATCGATA | 5940
| AGCTAGCTTT | CTAACTGATC | TATCCAAAAC | TGAAAATTAC | ATTCTTGATT | AGGTTTATCA | 6000
| CAGGCAAATG | TAATTTGTGG | TATTTTGCCG | TTCAAAATCT | GTAGAATTTT | CTCATTGGTC | 6060
| ACATTACAAC | CTGAAAATAC | TTTATCTACA | ATCATACCAT | TCTTAATAAC | ATGTCCCCTT | 6120
| AATACTAGGA | TCAGGCATGA | ACGCATCACA | GACAAAATCT | TCTTGACAAA | CGTCACAATT | 6180
| GATCCCTCCC | CATCCGTTAT | CACAATGACA | GGTGTCATTT | TGTGCTCTTA | TGGGACGATC | 6240
| CTTATTACCG | CTTTCATCCG | GTGATTGACC | GCCACAGAGG | GGCAGAGAGC | AATCATCACC | 6300
| TGCAAACCCT | TCTATACACT | CACATCTACC | AGTGATCGAA | TTGCATTCAG | AAAACTGTTT | 6360
| GCATTCAAAA | ATAGGTAGCA | TACAATTAAA | ACATGGCGGG | CATGTATCAT | TGCCCTTATC | 6420
| TTGTGCAGTT | AGACGCGAAT | TTTTCGAAGA | AGTACCTTCA | AGAATGGGG | TCTTATCTTG | 6480
| TTTTGCAAGT | ACCACTGAGC | AGGATAATAA | TAGAAATGAT | AATATACTAT | AGTAGAGATA | 6540
| ACGTCGATGA | CTTCCCATAC | TGTAATTGCT | TTTAGTTGTG | TATTTTAGT | GTGCAAGTTT | 6600
| CTGTAAATCG | ATTAATTTTT | TTTCTTTCC | TCTTTTATT | AACCTTAATT | TTTATTTTAG | 6660
| ATTCCTGACT | TCAACTCAAG | ACGCACAGAT | ATTATAACAT | CTGCATAATA | GGCATTTGCA | 6720
| AGAATTACTC | GTGAGTAAGG | AAAGAGTGAG | GAACTATCGC | ATACCTGCAT | TTAAAGATGC | 6780
| CGATTTGGGC | GCGAATCCTT | TATTTTGGCT | TCACCCTCAT | ACTATTATCA | GGGCCAGAAA | 6840
| AAGGAAGTGT | TTCCCTCCTT | CTTGAATTGA | TGTTACCCTC | ATAAAGCACG | TGGCCTCTTA | 6900
| TCGAGAAAGA | AATTACCGTC | GCTCGTGATT | TGTTTGCAAA | AAGAACAAAA | CTGAAAAAAC | 6960
| CCAGACACGC | TCGACTTCCT | GTCTTCCTAT | TGATTGCAGC | TTCCAATTTC | GTCACACAAC | 7020
| AAGGTCCTAG | CGACGGCTCA | CAGGTTTTGT | AACAAGCAAT | CGAAGGTTCT | GGAATGGCGG | 7080
| GGAAAGGGTT | TAGTACCACA | TGCTATGATG | CCCACTGTGA | TCTCCAGAGC | AAAGTTCGTT | 7140
| CGATCGTACT | GTACTCTCTC | TCTTTCAAAC | AGAATTGTCC | GAATCGTGTG | ACAACAACAG | 7200
| CCTGTTCTCA | CACACTCTTT | TCTTCTAACC | AAGGGGGTGG | TTTAGTTTAG | TAGAACCTCG | 7260
| TGAAACTTAC | ATTTACATAT | ATATAAACTT | GCATAAATTG | GTCAATGGAA | GAAATACATA | 7320
| TTTGGTCTTT | TCTAATTCGT | AGTTTTTCAA | GTTCTTAGAT | GCTTTCTTTT | TCTCTTTTTT | 7380
| ACAGATCATC | AAGGAAGTAA | TTATCTACTT | TTTACAACAA | ATACAAAAGA | TCTATGAGAT | 7440
| TTCCTTCAAT | TTTTACTGCA | GTTTTATTCG | CAGCATCCTC | CGCATTAGCT | GCTCCAGTCA | 7500
| ACACTACAAC | AGAAGATGAA | ACGGCACAAA | TTCCGGCTGA | AGCTGTCATC | GGTTACTTAG | 7560
| ATTTAGAAGG | GGATTTCGAT | GTTGCTGTTT | TGCCATTTTC | CAACAGCACA | AATAACGGGT | 7620
| TATTGTTTAT | AAATACTACT | ATTGCCAGCA | TTGCTGCTAA | AGAAGAAGGG | GTAAGCTTGG | 7680

| ATAAAAGAAA | CAGCGACTCT | GAATGCCCGC | TGAGCCATGA | TGGCTACTGC | CTGCACGACG | 7740 |
| GTGTATGCAT | GTATATCGAA | GCTCTGGACA | AATACGCATG | CAACTGCGTA | GTTGGTTACA | 7800 |
| TCGGCGAACG | TTGCCAGTAC | CGCGACCTGA | AATGGTGGGA | GCTCCGTTAA | TAAGGATCC  | 7859 |

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..15
        ( D ) OTHER INFORMATION: /note="oligonucleotide top strand
        adapter to fuse C-terminal end of the a-factor
        pro-peptide to synthetic hirudin gene"

( x i ) SEQUENCE DESCRIPTION: SEQ ID NO:5:

AGCTTGGATA AAAGA                                                                        15

( 2 ) INFORMATION FOR SEQ ID NO:6:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..11
        ( D ) OTHER INFORMATION: /note="bottom strand of adapter to
        fuse c- terminal end of the a-factor pro-peptide to
        synthetic hirudin gene"

( x i ) SEQUENCE DESCRIPTION: SEQ ID NO:6:

TCTTTTATCC A                                                                            11

( 2 ) INFORMATION FOR SEQ ID NO:7:

( i ) SEQUENCE CHARACTERISTICS:
        ( A ) LENGTH: 223 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..223
        ( D ) OTHER INFORMATION: /note="hirudin type HV-1 gene with
        5 amino acid adapter (corresponding to C-terminus
        of alpha factor) at amino terminus"

( i x ) FEATURE:
        ( A ) NAME/KEY: misc_feature
        ( B ) LOCATION: 1..6
        ( D ) OTHER INFORMATION: /note="HindIII site"

( i x ) FEATURE:
        ( A ) NAME/KEY: misc_feature
        ( B ) LOCATION: 218..223
        ( D ) OTHER INFORMATION: /note="BamHI site"

( x i ) SEQUENCE DESCRIPTION: SEQ ID NO:7:

AAGCTTGGAT AAAAGAGTTG TTTACACCGA CTGTACTGAA TCCGGACAAA ACCTGTGTTT           60

| | | | | |
|---|---|---|---|---|
| GTGTGAGGGT | TCTAACGTCT | GTGGTCAGGG | TAACAAATGC | ATCCTGGGTT CCGACGGTGA | 120 |
| AAAGAACCAA | TGTGTCACTG | GTGAAGGTAC | CCCAAAGCCG | CAGTCCCACA ACGATGGAGA | 180 |
| TTTCGAAGAA | ATCCCAGAAG | AATATCTGCA | GTAATAGGGA | TCC | 223 |

(2) INFORMATION FOR SEQ ID NO:8:

(i) SEQUENCE CHARACTERISTICS:
        (A) LENGTH: 420 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..420
        (D) OTHER INFORMATION: /note="Factor Xa-cleavable Hirudin-IEGR- Hirudin"

(ix) FEATURE:
        (A) NAME/KEY: CDS
        (B) LOCATION: 1..402

(ix) FEATURE:
        (A) NAME/KEY: mat_peptide
        (B) LOCATION: 1..402

(xi) SEQUENCE DESCRIPTION: SEQ ID NO:8:

```
GTT GTT TAC ACC GAC TGT ACT GAA TCC GGA CAA AAC CTG TGT TTG TGT        48
Val Val Tyr Thr Asp Cys Thr Glu Ser Gly Gln Asn Leu Cys Leu Cys
 1               5                  10                  15

GAG GGT TCT AAC GTC TGT GGT CAG GGT AAC AAA TGC ATC CTG GGT TCC        96
Glu Gly Ser Asn Val Cys Gly Gln Gly Asn Lys Cys Ile Leu Gly Ser
                20                  25                  30

GAC GGT GAA AAG AAC CAA TGT GTC ACT GGT GAA GGT ACC CCA AAG CCG       144
Asp Gly Glu Lys Asn Gln Cys Val Thr Gly Glu Gly Thr Pro Lys Pro
            35                  40                  45

CAG TCC CAC AAC GAT GGA GAT TTC GAA GAA ATC CCA GAA GAA TAT CTG       192
Gln Ser His Asn Asp Gly Asp Phe Glu Glu Ile Pro Glu Glu Tyr Leu
        50                  55                  60

CAG ATC GAA GGA AGA GTT GTT TAC ACC GAC TGT ACT GAA TCC GGA CAA       240
Gln Ile Glu Gly Arg Val Val Tyr Thr Asp Cys Thr Glu Ser Gly Gln
65                  70                  75                  80

AAC CTG TGT TTG TGT GAG GGT TCT AAC GTC TGT GGT CAG GGT AAC AAA       288
Asn Leu Cys Leu Cys Glu Gly Ser Asn Val Cys Gly Gln Gly Asn Lys
                85                  90                  95

TGC ATC CTG GGT TCC GAC GGT GAA AAG AAC CAA TGT GTC ACT GGT GAA       336
Cys Ile Leu Gly Ser Asp Gly Glu Lys Asn Gln Cys Val Thr Gly Glu
            100                 105                 110

GGT ACC CCA AAG CCG CAG TCC CAC AAC GAT GGA GAT TTC GAA GAA ATC       384
Gly Thr Pro Lys Pro Gln Ser His Asn Asp Gly Asp Phe Glu Glu Ile
        115                 120                 125

CCA GAA GAA TAT CTG CAG TAATAGGGAT CCGAATTC                           420
Pro Glu Glu Tyr Leu Gln
        130
```

(2) INFORMATION FOR SEQ ID NO:9:

(i) SEQUENCE CHARACTERISTICS:
        (A) LENGTH: 134 amino acids
        (B) TYPE: amino acid
        (D) TOPOLOGY: linear (ii) MOLECULE TYPE: protein (xi) SEQUENCE DESCRIPTION: SEQ ID NO:9:

```
Val Val Tyr Thr Asp Cys Thr Glu Ser Gly Gln Asn Leu Cys Leu Cys
```

|  1 | | |  | 5 | | | | | 10 | | | | | 15 |
|---|---|---|---|---|---|---|---|---|---|---|---|---|---|---|
| Glu | Gly | Ser | Asn | Val | Cys | Gly | Gln | Gly | Asn | Lys | Cys | Ile | Leu | Gly | Ser |
|  |  |  | 20 |  |  |  |  |  | 25 |  |  |  | 30 |  |  |
| Asp | Gly | Glu | Lys | Asn | Gln | Cys | Val | Thr | Gly | Glu | Gly | Thr | Pro | Lys | Pro |
|  |  |  | 35 |  |  |  |  | 40 |  |  |  |  | 45 |  |  |
| Gln | Ser | His | Asn | Asp | Gly | Asp | Phe | Glu | Glu | Ile | Pro | Glu | Glu | Tyr | Leu |
|  |  | 50 |  |  |  | 55 |  |  |  |  |  | 60 |  |  |  |
| Gln | Ile | Glu | Gly | Arg | Val | Val | Tyr | Thr | Asp | Cys | Thr | Glu | Ser | Gly | Gln |
| 65 |  |  |  |  | 70 |  |  |  |  | 75 |  |  |  |  | 80 |
| Asn | Leu | Cys | Leu | Cys | Glu | Gly | Ser | Asn | Val | Cys | Gly | Gln | Gly | Asn | Lys |
|  |  |  |  | 85 |  |  |  |  | 90 |  |  |  |  | 95 |  |
| Cys | Ile | Leu | Gly | Ser | Asp | Gly | Glu | Lys | Asn | Gln | Cys | Val | Thr | Gly | Glu |
|  |  |  |  | 100 |  |  |  |  | 105 |  |  |  |  | 110 |  |
| Gly | Thr | Pro | Lys | Pro | Gln | Ser | His | Asn | Asp | Gly | Asp | Phe | Glu | Glu | Ile |
|  |  |  | 115 |  |  |  |  | 120 |  |  |  |  | 125 |  |  |
| Pro | Glu | Glu | Tyr | Leu | Gln |  |  |  |  |  |  |  |  |  |  |
|  |  |  | 130 |  |  |  |  |  |  |  |  |  |  |  |  |

( 2 ) INFORMATION FOR SEQ ID NO:10:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..46
        ( D ) OTHER INFORMATION: /note="oligonucleotide BB2988"

( x i ) SEQUENCE DESCRIPTION: SEQ ID NO:10:

CAGTCGGTGT AAACAACTCT TCCTTCGATC TGCAGATATT CTTCTG    46

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..17
        ( D ) OTHER INFORMATION: /note="M13 universal primer from
            USB, Cleveland, OH"

( x i ) SEQUENCE DESCRIPTION: SEQ ID NO:11:

GTTTTCCCAG TCACGAC    17

( 2 ) INFORMATION FOR SEQ ID NO:12:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..40
        ( D ) OTHER INFORMATION: /note="oligonucleotide BB1888"

( x i ) SEQUENCE DESCRIPTION: SEQ ID NO:12:

GTTCATGGAT CCTTATTTGT CGTTAGGGTT ATCAGGTATA                                                                40

( 2 ) INFORMATION FOR SEQ ID NO:13:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..40
        ( D ) OTHER INFORMATION: /note="oligonucleotide BB1887"

( x i ) SEQUENCE DESCRIPTION: SEQ ID NO:13:

TCAAGTGAAT TCATGAAAAA TTACTTATCT TTTGGGATGT                                                                40

( 2 ) INFORMATION FOR SEQ ID NO:14:

( i ) SEQUENCE CHARACTERISTICS:
        ( A ) LENGTH: 1335 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..1335
        ( D ) OTHER INFORMATION: /note="Streptokinase gene from S. equisimilis"

( i x ) FEATURE:
        ( A ) NAME/KEY: CDS
        ( B ) LOCATION: 7..1326

( i x ) FEATURE:
        ( A ) NAME/KEY: mat_peptide
        ( B ) LOCATION: 7..1326

( x i ) SEQUENCE DESCRIPTION: SEQ ID NO:14:

```
GAATTC ATG AAA AAT TAC TTA TCT TTT GGG ATG TTT GCA CTG CTG TTT         48
       Met Lys Asn Tyr Leu Ser Phe Gly Met Phe Ala Leu Leu Phe
        1            5                  10

GCA CTA ACA TTT GGA ACA GTC AAT TCT GTC CAA GCT ATT GCT GGA CCT         96
Ala Leu Thr Phe Gly Thr Val Asn Ser Val Gln Ala Ile Ala Gly Pro
 15              20                  25                      30

GAG TGG CTG CTA GAC CGT CCA TCT GTC AAC AAC AGC CAA TTA GTT GTT        144
Glu Trp Leu Leu Asp Arg Pro Ser Val Asn Asn Ser Gln Leu Val Val
                 35                  40                  45

AGC GTT GCT GGT ACT GTT GAG GGG ACG AAT CAA GAC ATT AGT CTT AAA        192
Ser Val Ala Gly Thr Val Glu Gly Thr Asn Gln Asp Ile Ser Leu Lys
             50                  55                  60

TTT TTT GAA ATT GAC CTA ACA TCA CGA CCT GCT CAT GGA GGA AAG ACA        240
Phe Phe Glu Ile Asp Leu Thr Ser Arg Pro Ala His Gly Gly Lys Thr
         65                  70                  75

GAG CAA GGC TTA AGT CCA AAA TCA AAA CCA TTT GCT ACT GAT AGT GGC        288
Glu Gln Gly Leu Ser Pro Lys Ser Lys Pro Phe Ala Thr Asp Ser Gly
     80                  85                  90

GCG ATG CCA CAT AAA CTT GAA AAA GCT GAC TTA CTA AAG GCT ATT CAA        336
Ala Met Pro His Lys Leu Glu Lys Ala Asp Leu Leu Lys Ala Ile Gln
 95             100                 105                     110

GAA CAA TTG ATC GCT AAC GTC CAC AGT AAC GAC GAC TAC TTT GAG GTC        384
Glu Gln Leu Ile Ala Asn Val His Ser Asn Asp Asp Tyr Phe Glu Val
```

|  |  |  |  |  |  |  |  |  |  |  |  |  |  |  |  |
|---|---|---|---|---|---|---|---|---|---|---|---|---|---|---|---|
|  |  |  |  | 115 |  |  |  |  | 120 |  |  |  |  | 125 |  |

```
ATT GAT TTT GCA AGC GAT GCA ACC ATT ACT GAT CGA AAC GGC AAG GTC     432
Ile Asp Phe Ala Ser Asp Ala Thr Ile Thr Asp Arg Asn Gly Lys Val
            130                 135                 140

TAC TTT GCT GAC AAA GAT GGT TCG GTA ACC TTG CCG ACC CAA CCT GTC     480
Tyr Phe Ala Asp Lys Asp Gly Ser Val Thr Leu Pro Thr Gln Pro Val
            145                 150                 155

CAA GAA TTT TTG CTA AGC GGA CAT GTG CGC GTT AGA CCA TAT AAA GAA     528
Gln Glu Phe Leu Leu Ser Gly His Val Arg Val Arg Pro Tyr Lys Glu
    160                 165                 170

AAA CCA ATA CAA AAT CAA GCG AAA TCT GTT GAT GTG GAA TAT ACT GTA     576
Lys Pro Ile Gln Asn Gln Ala Lys Ser Val Asp Val Glu Tyr Thr Val
175                 180                 185                 190

CAG TTT ACT CCC TTA AAC CCT GAT GAC GAT TTC AGA CCA GGT CTC AAA     624
Gln Phe Thr Pro Leu Asn Pro Asp Asp Asp Phe Arg Pro Gly Leu Lys
                195                 200                 205

GAT ACT AAG CTA TTG AAA ACA CTA GCT ATC GGT GAC ACC ATC ACA TCT     672
    Asp Thr Lys Leu Leu Lys Thr Leu Ala Ile Gly Asp Thr Ile Thr Ser
                    210                 215                 220

CAA GAA TTA CTA GCT CAA GCA CAA AGC ATT TTA AAC AAA ACC CAT CCA     720
Gln Glu Leu Leu Ala Gln Ala Gln Ser Ile Leu Asn Lys Thr His Pro
            225                 230                 235

GGC TAT ACG ATT TAT GAA CGT GAC TCC TCA ATC GTC ACT CAT GAC AAT     768
Gly Tyr Thr Ile Tyr Glu Arg Asp Ser Ser Ile Val Thr His Asp Asn
        240                 245                 250

GAC ATT TTC CGT ACG ATT TTA CCA ATG GAT CAA GAG TTT ACT TAC CAT     816
Asp Ile Phe Arg Thr Ile Leu Pro Met Asp Gln Glu Phe Thr Tyr His
255                 260                 265                 270

GTC AAA AAT CGG GAA CAA GCT TAT GAG ATC AAT AAA AAA TCT GGT CTG     864
Val Lys Asn Arg Glu Gln Ala Tyr Glu Ile Asn Lys Lys Ser Gly Leu
                275                 280                 285

AAT GAA GAA ATA AAC AAC ACT GAC CTG ATC TCT GAG AAA TAT TAC GTC     912
Asn Glu Glu Ile Asn Asn Thr Asp Leu Ile Ser Glu Lys Tyr Tyr Val
            290                 295                 300

CTT AAA AAA GGG GAA AAG CCG TAT GAT CCC TTT GAT CGC AGT CAC TTG     960
Leu Lys Lys Gly Glu Lys Pro Tyr Asp Pro Phe Asp Arg Ser His Leu
        305                 310                 315

AAA CTG TTC ACC ATC AAA TAC GTT GAT GTC AAC ACC AAC GAA TTG CTA    1008
Lys Leu Phe Thr Ile Lys Tyr Val Asp Val Asn Thr Asn Glu Leu Leu
    320                 325                 330

AAA AGC GAG CAG CTC TTA ACA GCT AGC GAA CGT AAC TTA GAC TTC AGA    1056
Lys Ser Glu Gln Leu Leu Thr Ala Ser Glu Arg Asn Leu Asp Phe Arg
335                 340                 345                 350

GAT TTA TAC GAT CCT CGT GAT AAG GCT AAA CTA CTC TAC AAC AAT CTC    1104
Asp Leu Tyr Asp Pro Arg Asp Lys Ala Lys Leu Leu Tyr Asn Asn Leu
                355                 360                 365

GAT GCT TTT GGT ATT ATG GAC TAT ACC TTA ACT GGA AAA GTA GAA GAT    1152
Asp Ala Phe Gly Ile Met Asp Tyr Thr Leu Thr Gly Lys Val Glu Asp
            370                 375                 380

AAT CAC GAT GAC ACC AAC CGT ATC ATA ACC GTT TAT ATG GGC AAG CGA    1200
Asn His Asp Asp Thr Asn Arg Ile Ile Thr Val Tyr Met Gly Lys Arg
        385                 390                 395

CCC GAA GGA GAG AAT GCT AGC TAT CAT TTA GCC TAT GAT AAA GAT CGT    1248
Pro Glu Gly Glu Asn Ala Ser Tyr His Leu Ala Tyr Asp Lys Asp Arg
    400                 405                 410

TAT ACC GAA GAA GAA CGA GAA GTT TAC AGC TAC CTG CGT TAT ACA GGG    1296
Tyr Thr Glu Glu Glu Arg Glu Val Tyr Ser Tyr Leu Arg Tyr Thr Gly
415                 420                 425                 430

ACA CCT ATA CCT GAT AAC CCT AAC GAC AAA TAAGGATCC                   1335
    Thr Pro Ile Pro Asp Asn Pro Asn Asp Lys
                435                 440
```

( 2 ) INFORMATION FOR SEQ ID NO:15:

( i ) SEQUENCE CHARACTERISTICS:
        ( A ) LENGTH: 440 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Met Lys Asn Tyr Leu Ser Phe Gly Met Phe Ala Leu Leu Phe Ala Leu
 1               5                  10                  15

Thr Phe Gly Thr Val Asn Ser Val Gln Ala Ile Ala Gly Pro Glu Trp
                20                  25                  30

Leu Leu Asp Arg Pro Ser Val Asn Ser Gln Leu Val Val Ser Val
            35                  40                  45

Ala Gly Thr Val Glu Gly Thr Asn Gln Asp Ile Ser Leu Lys Phe Phe
        50                  55                  60

Glu Ile Asp Leu Thr Ser Arg Pro Ala His Gly Gly Lys Thr Glu Gln
65                  70                  75                  80

Gly Leu Ser Pro Lys Ser Lys Pro Phe Ala Thr Asp Ser Gly Ala Met
                85                  90                  95

Pro His Lys Leu Glu Lys Ala Asp Leu Leu Lys Ala Ile Gln Glu Gln
               100                 105                 110

Leu Ile Ala Asn Val His Ser Asn Asp Asp Tyr Phe Glu Val Ile Asp
           115                 120                 125

Phe Ala Ser Asp Ala Thr Ile Thr Asp Arg Asn Gly Lys Val Tyr Phe
       130                 135                 140

Ala Asp Lys Asp Gly Ser Val Thr Leu Pro Thr Gln Pro Val Gln Glu
145                 150                 155                 160

Phe Leu Leu Ser Gly His Val Arg Val Arg Pro Tyr Lys Glu Lys Pro
               165                 170                 175

Ile Gln Asn Gln Ala Lys Ser Val Asp Val Glu Tyr Thr Val Gln Phe
           180                 185                 190

Thr Pro Leu Asn Pro Asp Asp Phe Arg Pro Gly Leu Lys Asp Thr
       195                 200                 205

Lys Leu Leu Lys Thr Leu Ala Ile Gly Asp Thr Ile Thr Ser Gln Glu
210                 215                 220

Leu Leu Ala Gln Ala Gln Ser Ile Leu Asn Lys Thr His Pro Gly Tyr
225                 230                 235                 240

Thr Ile Tyr Glu Arg Asp Ser Ser Ile Val Thr His Asp Asn Asp Ile
               245                 250                 255

Phe Arg Thr Ile Leu Pro Met Asp Gln Glu Phe Thr Tyr His Val Lys
           260                 265                 270

Asn Arg Glu Gln Ala Tyr Glu Ile Asn Lys Lys Ser Gly Leu Asn Glu
       275                 280                 285

Glu Ile Asn Asn Thr Asp Leu Ile Ser Glu Lys Tyr Tyr Val Leu Lys
290                 295                 300

Lys Gly Glu Lys Pro Tyr Asp Pro Phe Asp Arg Ser His Leu Lys Leu
305                 310                 315                 320

Phe Thr Ile Lys Tyr Val Asp Val Asn Thr Asn Glu Leu Leu Lys Ser
               325                 330                 335

Glu Gln Leu Leu Thr Ala Ser Glu Arg Asn Leu Asp Phe Arg Asp Leu
           340                 345                 350

Tyr Asp Pro Arg Asp Lys Ala Lys Leu Leu Tyr Asn Asn Leu Asp Ala
       355                 360                 365

Phe Gly Ile Met Asp Tyr Thr Leu Thr Gly Lys Val Glu Asp Asn His
```

|   | 370 |   |   |   | 375 |   |   |   |   | 380 |   |   |
|---|-----|---|---|---|-----|---|---|---|---|-----|---|---|

Asp Asp Thr Asn Arg Ile Ile Thr Val Tyr Met Gly Lys Arg Pro Glu
385                     390                 395                 400

Gly Glu Asn Ala Ser Tyr His Leu Ala Tyr Asp Lys Asp Arg Tyr Thr
            405             410             415

Glu Glu Glu Arg Glu Val Tyr Ser Tyr Leu Arg Tyr Thr Gly Thr Pro
            420             425             430

Ile Pro Asp Asn Pro Asn Asp Lys
        435             440

( 2 ) INFORMATION FOR SEQ ID NO:16:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..26
        ( D ) OTHER INFORMATION: /note="oligonucleotide BB2175"

( x i ) SEQUENCE DESCRIPTION: SEQ ID NO:16:

GATAAGTAAT TTTTCATATG AATTCG        26

( 2 ) INFORMATION FOR SEQ ID NO:17:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..18
        ( D ) OTHER INFORMATION: /note="oligonucleotide BB2358"

( x i ) SEQUENCE DESCRIPTION: SEQ ID NO:17:

CATGAGCAGG TCGTGATG        18

( 2 ) INFORMATION FOR SEQ ID NO:18:

( i ) SEQUENCE CHARACTERISTICS:
        ( A ) LENGTH: 1317 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..1317
        ( D ) OTHER INFORMATION: /note="OmpAL fused to mature
        streptokinase gene"

( i x ) FEATURE:
        ( A ) NAME/KEY: CDS
        ( B ) LOCATION: 4..1308

( i x ) FEATURE:
        ( A ) NAME/KEY: mat_peptide
        ( B ) LOCATION: 4..1308

( x i ) SEQUENCE DESCRIPTION: SEQ ID NO:18:

CAT ATG AAA AAG ACA GCT ATC GCG ATT GCA GTG GCA CTG GCT GGT TTC        48

|  | Met<br>1 | Lys | Lys | Thr | Ala<br>5 | Ile | Ala | Ile | Ala | Val<br>10 | Ala | Leu | Ala | Gly | Phe<br>15 |  |
|---|---|---|---|---|---|---|---|---|---|---|---|---|---|---|---|---|
| GCG<br>Ala | ACC<br>Thr | GTA<br>Val | GCG<br>Ala<br>20 | CAG<br>Gln | GCC<br>Ala | ATT<br>Ile | GCT<br>Ala | GGA<br>Gly | CCT<br>Pro<br>25 | GAG<br>Glu | TGG<br>Trp | CTG<br>Leu | CTA<br>Leu | GAC<br>Asp<br>30 | CGT<br>Arg | 96 |
| CCA<br>Pro | TCT<br>Ser | GTC<br>Val | AAC<br>Asn<br>35 | AAC<br>Asn | AGC<br>Ser | CAA<br>Gln | TTA<br>Leu | GTT<br>Val<br>40 | GTT<br>Val | AGC<br>Ser | GTT<br>Val | GCT<br>Ala | GGT<br>Gly<br>45 | ACT<br>Thr | GTT<br>Val | 144 |
| GAG<br>Glu | GGG<br>Gly | ACG<br>Thr<br>50 | AAT<br>Asn | CAA<br>Gln | GAC<br>Asp | ATT<br>Ile | AGT<br>Ser<br>55 | CTT<br>Leu | AAA<br>Lys | TTT<br>Phe | TTT<br>Phe | GAA<br>Glu<br>60 | ATT<br>Ile | GAC<br>Asp | CTA<br>Leu | 192 |
| ACA<br>Thr | TCA<br>Ser<br>65 | CGA<br>Arg | CCT<br>Pro | GCT<br>Ala | CAT<br>His | GGA<br>Gly<br>70 | GGA<br>Gly | AAG<br>Lys | ACA<br>Thr | GAG<br>Glu | CAA<br>Gln<br>75 | GGC<br>Gly | TTA<br>Leu | AGT<br>Ser | CCA<br>Pro | 240 |
| AAA<br>Lys<br>80 | TCA<br>Ser | AAA<br>Lys | CCA<br>Pro | TTT<br>Phe | GCT<br>Ala<br>85 | ACT<br>Thr | GAT<br>Asp | AGT<br>Ser | GGC<br>Gly | GCG<br>Ala<br>90 | ATG<br>Met | CCA<br>Pro | CAT<br>His | AAA<br>Lys | CTT<br>Leu<br>95 | 288 |
| GAA<br>Glu | AAA<br>Lys | GCT<br>Ala | GAC<br>Asp | TTA<br>Leu<br>100 | CTA<br>Leu | AAG<br>Lys | GCT<br>Ala | ATT<br>Ile | CAA<br>Gln<br>105 | GAA<br>Glu | CAA<br>Gln | TTG<br>Leu | ATC<br>Ile | GCT<br>Ala<br>110 | AAC<br>Asn | 336 |
| GTC<br>Val | CAC<br>His | AGT<br>Ser | AAC<br>Asn<br>115 | GAC<br>Asp | GAC<br>Asp | TAC<br>Tyr | TTT<br>Phe | GAG<br>Glu<br>120 | GTC<br>Val | ATT<br>Ile | GAT<br>Asp | TTT<br>Phe | GCA<br>Ala<br>125 | AGC<br>Ser | GAT<br>Asp | 384 |
| GCA<br>Ala | ACC<br>Thr | ATT<br>Ile<br>130 | ACT<br>Thr | GAT<br>Asp | CGA<br>Arg | AAC<br>Asn | GGC<br>Gly<br>135 | AAG<br>Lys | GTC<br>Val | TAC<br>Tyr | TTT<br>Phe | GCT<br>Ala<br>140 | GAC<br>Asp | AAA<br>Lys | GAT<br>Asp | 432 |
| GGT<br>Gly | TCG<br>Ser<br>145 | GTA<br>Val | ACC<br>Thr | TTG<br>Leu | CCG<br>Pro | ACC<br>Thr<br>150 | CAA<br>Gln | CCT<br>Pro | GTC<br>Val | CAA<br>Gln | GAA<br>Glu<br>155 | TTT<br>Phe | TTG<br>Leu | CTA<br>Leu | AGC<br>Ser | 480 |
| GGA<br>Gly<br>160 | CAT<br>His | GTG<br>Val | CGC<br>Arg | GTT<br>Val | AGA<br>Arg<br>165 | CCA<br>Pro | TAT<br>Tyr | AAA<br>Lys | GAA<br>Glu | AAA<br>Lys<br>170 | CCA<br>Pro | ATA<br>Ile | CAA<br>Gln | AAT<br>Asn | CAA<br>Gln<br>175 | 528 |
| GCG<br>Ala | AAA<br>Lys | TCT<br>Ser | GTT<br>Val | GAT<br>Asp<br>180 | GTG<br>Val | GAA<br>Glu | TAT<br>Tyr | ACT<br>Thr | GTA<br>Val<br>185 | CAG<br>Gln | TTT<br>Phe | ACT<br>Thr | CCC<br>Pro | TTA<br>Leu<br>190 | AAC<br>Asn | 576 |
| CCT<br>Pro | GAT<br>Asp | GAC<br>Asp | GAT<br>Asp<br>195 | TTC<br>Phe | AGA<br>Arg | CCA<br>Pro | GGT<br>Gly | CTC<br>Leu<br>200 | AAA<br>Lys | GAT<br>Asp | ACT<br>Thr | AAG<br>Lys | CTA<br>Leu<br>205 | TTG<br>Leu | AAA<br>Lys | 624 |
| ACA<br>Thr | CTA<br>Leu | GCT<br>Ala<br>210 | ATC<br>Ile | GGT<br>Gly | GAC<br>Asp | ACC<br>Thr | ATC<br>Ile<br>215 | ACA<br>Thr | TCT<br>Ser | CAA<br>Gln | GAA<br>Glu | TTA<br>Leu<br>220 | CTA<br>Leu | GCT<br>Ala | CAA<br>Gln | 672 |
| GCA<br>Ala | CAA<br>Gln<br>225 | AGC<br>Ser | ATT<br>Ile | TTA<br>Leu | AAC<br>Asn | AAA<br>Lys<br>230 | ACC<br>Thr | CAT<br>His | CCA<br>Pro | GGC<br>Gly | TAT<br>Tyr<br>235 | ACG<br>Thr | ATT<br>Ile | TAT<br>Tyr | GAA<br>Glu | 720 |
| CGT<br>Arg<br>240 | GAC<br>Asp | TCC<br>Ser | TCA<br>Ser | ATC<br>Ile | GTC<br>Val<br>245 | ACT<br>Thr | CAT<br>His | GAC<br>Asp | AAT<br>Asn | GAC<br>Asp<br>250 | ATT<br>Ile | TTC<br>Phe | CGT<br>Arg | ACG<br>Thr | ATT<br>Ile<br>255 | 768 |
| TTA<br>Leu | CCA<br>Pro | ATG<br>Met | GAT<br>Asp | CAA<br>Gln<br>260 | GAG<br>Glu | TTT<br>Phe | ACT<br>Thr | TAC<br>Tyr | CAT<br>His<br>265 | GTC<br>Val | AAA<br>Lys | AAT<br>Asn | CGG<br>Arg | GAA<br>Glu<br>270 | CAA<br>Gln | 816 |
| GCT<br>Ala | TAT<br>Tyr | GAG<br>Glu | ATC<br>Ile<br>275 | AAT<br>Asn | AAA<br>Lys | AAA<br>Lys | TCT<br>Ser | GGT<br>Gly<br>280 | CTG<br>Leu | AAT<br>Asn | GAA<br>Glu | GAA<br>Glu | ATA<br>Ile<br>285 | AAC<br>Asn | AAC<br>Asn | 864 |
| ACT<br>Thr | GAC<br>Asp | CTG<br>Leu<br>290 | ATC<br>Ile | TCT<br>Ser | GAG<br>Glu | AAA<br>Lys | TAT<br>Tyr<br>295 | TAC<br>Tyr | GTC<br>Val | CTT<br>Leu | AAA<br>Lys | AAA<br>Lys<br>300 | GGG<br>Gly | GAA<br>Glu | AAG<br>Lys | 912 |
| CCG<br>Pro | TAT<br>Tyr<br>305 | GAT<br>Asp | CCC<br>Pro | TTT<br>Phe | GAT<br>Asp | CGC<br>Arg<br>310 | AGT<br>Ser | CAC<br>His | TTG<br>Leu | AAA<br>Lys | CTG<br>Leu<br>315 | TTC<br>Phe | ACC<br>Thr | ATC<br>Ile | AAA<br>Lys | 960 |
| TAC<br>Tyr<br>320 | GTT<br>Val | GAT<br>Asp | GTC<br>Val | AAC<br>Asn | ACC<br>Thr<br>325 | AAC<br>Asn | GAA<br>Glu | TTG<br>Leu | CTA<br>Leu | AAA<br>Lys<br>330 | AGC<br>Ser | GAG<br>Glu | CAG<br>Gln | CTC<br>Leu | TTA<br>Leu<br>335 | 1008 |

```
ACA GCT AGC GAA CGT AAC TTA GAC TTC AGA GAT TTA TAC GAT CCT CGT    1056
Thr Ala Ser Glu Arg Asn Leu Asp Phe Arg Asp Leu Tyr Asp Pro Arg
            340                 345                 350

GAT AAG GCT AAA CTA CTC TAC AAC AAT CTC GAT GCT TTT GGT ATT ATG    1104
Asp Lys Ala Lys Leu Leu Tyr Asn Asn Leu Asp Ala Phe Gly Ile Met
            355                 360                 365

GAC TAT ACC TTA ACT GGA AAA GTA GAA GAT AAT CAC GAT GAC ACC AAC    1152
Asp Tyr Thr Leu Thr Gly Lys Val Glu Asp Asn His Asp Asp Thr Asn
            370                 375                 380

CGT ATC ATA ACC GTT TAT ATG GGC AAG CGA CCC GAA GGA GAG AAT GCT    1200
Arg Ile Ile Thr Val Tyr Met Gly Lys Arg Pro Glu Gly Glu Asn Ala
        385                 390                 395

AGC TAT CAT TTA GCC TAT GAT AAA GAT CGT TAT ACC GAA GAA GAA CGA    1248
Ser Tyr His Leu Ala Tyr Asp Lys Asp Arg Tyr Thr Glu Glu Glu Arg
400                 405                 410                 415

GAA GTT TAC AGC TAC CTG CGT TAT ACA GGG ACA CCT ATA CCT GAT AAC    1296
Glu Val Tyr Ser Tyr Leu Arg Tyr Thr Gly Thr Pro Ile Pro Asp Asn
                420                 425                 430

CCT AAC GAC AAA TAAGGATCC                                           1317
Pro Asn Asp Lys
            435
```

( 2 ) INFORMATION FOR SEQ ID NO:19:

( i ) SEQUENCE CHARACTERISTICS:
        ( A ) LENGTH: 435 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met Lys Lys Thr Ala Ile Ala Ile Ala Val Ala Leu Ala Gly Phe Ala
 1               5                  10                  15

Thr Val Ala Gln Ala Ile Ala Gly Pro Glu Trp Leu Leu Asp Arg Pro
                20                  25                  30

Ser Val Asn Asn Ser Gln Leu Val Val Ser Val Ala Gly Thr Val Glu
                35                  40                  45

Gly Thr Asn Gln Asp Ile Ser Leu Lys Phe Phe Glu Ile Asp Leu Thr
        50                  55                  60

Ser Arg Pro Ala His Gly Gly Lys Thr Glu Gln Gly Leu Ser Pro Lys
65                  70                  75                  80

Ser Lys Pro Phe Ala Thr Asp Ser Gly Ala Met Pro His Lys Leu Glu
                85                  90                  95

Lys Ala Asp Leu Leu Lys Ala Ile Gln Glu Gln Leu Ile Ala Asn Val
               100                 105                 110

His Ser Asn Asp Asp Tyr Phe Glu Val Ile Asp Phe Ala Ser Asp Ala
        115                 120                 125

Thr Ile Thr Asp Arg Asn Gly Lys Val Tyr Phe Ala Asp Lys Asp Gly
    130                 135                 140

Ser Val Thr Leu Pro Thr Gln Pro Val Gln Glu Phe Leu Leu Ser Gly
145                 150                 155                 160

His Val Arg Val Arg Pro Tyr Lys Glu Lys Pro Ile Gln Asn Gln Ala
                165                 170                 175

Lys Ser Val Asp Val Glu Tyr Thr Val Gln Phe Thr Pro Leu Asn Pro
                180                 185                 190

Asp Asp Asp Phe Arg Pro Gly Leu Lys Asp Thr Lys Leu Leu Lys Thr
        195                 200                 205

Leu Ala Ile Gly Asp Thr Ile Thr Ser Gln Glu Leu Leu Ala Gln Ala
    210                 215                 220
```

```
Gln  Ser  Ile  Leu  Asn  Lys  Thr  His  Pro  Gly  Tyr  Thr  Ile  Tyr  Glu  Arg
225                 230                      235                      240

Asp  Ser  Ser  Ile  Val  Thr  His  Asp  Asn  Asp  Ile  Phe  Arg  Thr  Ile  Leu
                    245                      250                      255

Pro  Met  Asp  Gln  Glu  Phe  Thr  Tyr  His  Val  Lys  Asn  Arg  Glu  Gln  Ala
               260                      265                 270

Tyr  Glu  Ile  Asn  Lys  Lys  Ser  Gly  Leu  Asn  Glu  Glu  Ile  Asn  Asn  Thr
          275                      280                      285

Asp  Leu  Ile  Ser  Glu  Lys  Tyr  Tyr  Val  Leu  Lys  Lys  Gly  Glu  Lys  Pro
     290                      295                 300

Tyr  Asp  Pro  Phe  Asp  Arg  Ser  His  Leu  Lys  Leu  Phe  Thr  Ile  Lys  Tyr
305                      310                      315                      320

Val  Asp  Val  Asn  Thr  Asn  Glu  Leu  Leu  Lys  Ser  Glu  Gln  Leu  Leu  Thr
                    325                      330                      335

Ala  Ser  Glu  Arg  Asn  Leu  Asp  Phe  Arg  Asp  Leu  Tyr  Asp  Pro  Arg  Asp
               340                      345                 350

Lys  Ala  Lys  Leu  Leu  Tyr  Asn  Asn  Leu  Asp  Ala  Phe  Gly  Ile  Met  Asp
          355                      360                 365

Tyr  Thr  Leu  Thr  Gly  Lys  Val  Glu  Asp  Asn  His  Asp  Asp  Thr  Asn  Arg
     370                      375                 380

Ile  Ile  Thr  Val  Tyr  Met  Gly  Lys  Arg  Pro  Glu  Gly  Glu  Asn  Ala  Ser
385                      390                 395                           400

Tyr  His  Leu  Ala  Tyr  Asp  Lys  Asp  Arg  Tyr  Thr  Glu  Glu  Glu  Arg  Glu
                    405                      410                      415

Val  Tyr  Ser  Tyr  Leu  Arg  Tyr  Thr  Gly  Thr  Pro  Ile  Pro  Asp  Asn  Pro
               420                      425                 430

Asn  Asp  Lys
          435
```

( 2 ) INFORMATION FOR SEQ ID NO:20:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..44
        ( D ) OTHER INFORMATION: /note="oligonucleotide BB58"

( x i ) SEQUENCE DESCRIPTION: SEQ ID NO:20:

```
AGCTCGTAGA CACTCTGCAG TTCGTTTGTG GTGACCGTGG CTTC                          44
```

( 2 ) INFORMATION FOR SEQ ID NO:21:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..30
        ( D ) OTHER INFORMATION: /note="oligonucleotide BB2658"

( x i ) SEQUENCE DESCRIPTION: SEQ ID NO:21:

```
ACCGTAGCGC AGGCCATTGC TGGACCTGAG                                          30
```

( 2 ) INFORMATION FOR SEQ ID NO:22:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_feature
    ( B ) LOCATION: 1..17
    ( D ) OTHER INFORMATION: /note="oligonucleotide BB2753"

( x i ) SEQUENCE DESCRIPTION: SEQ ID NO:22:

GACACCAACC GTATCAT                         17

( 2 ) INFORMATION FOR SEQ ID NO:23:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_feature
    ( B ) LOCATION: 1..17
    ( D ) OTHER INFORMATION: /note="oligonucleotide BB3510"

( x i ) SEQUENCE DESCRIPTION: SEQ ID NO:23:

CACTATCAGT AGCAAAT                          17

( 2 ) INFORMATION FOR SEQ ID NO:24:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_feature
    ( B ) LOCATION: 1..31
    ( D ) OTHER INFORMATION: /note="oligonucleotide BB3802"

( x i ) SEQUENCE DESCRIPTION: SEQ ID NO:24:

GAAATACTTA CATATGATTG CTGGACCTGA G               31

( 2 ) INFORMATION FOR SEQ ID NO:25:

( i ) SEQUENCE CHARACTERISTICS:
    ( A ) LENGTH: 1257 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_feature
    ( B ) LOCATION: 1..1257
    ( D ) OTHER INFORMATION: /note="Methionyl-streptokinase
      fusion protein"

( i x ) FEATURE:
    ( A ) NAME/KEY: CDS
    ( B ) LOCATION: 4..1248

( i x ) FEATURE:
  ( A ) NAME/KEY: mat_peptide
  ( B ) LOCATION: 4..1248

( x i ) SEQUENCE DESCRIPTION: SEQ ID NO:25:

| | | | | | | | | | | | | | | | | |
|---|---|---|---|---|---|---|---|---|---|---|---|---|---|---|---|---|
| CAT | ATG | ATT | GCT | GGA | CCT | GAG | TGG | CTG | CTA | GAC | CGT | CCA | TCT | GTC | AAC | 48 |
| | Met | Ile | Ala | Gly | Pro | Glu | Trp | Leu | Leu | Asp | Arg | Pro | Ser | Val | Asn | |
| | 1 | | | | 5 | | | | | 10 | | | | | 15 | |
| AAC | AGC | CAA | TTA | GTT | GTT | AGC | GTT | GCT | GGT | ACT | GTT | GAG | GGG | ACG | AAT | 96 |
| Asn | Ser | Gln | Leu | Val | Val | Ser | Val | Ala | Gly | Thr | Val | Glu | Gly | Thr | Asn | |
| | | | 20 | | | | | 25 | | | | | | 30 | | |
| CAA | GAC | ATT | AGT | CTT | AAA | TTT | TTT | GAA | ATT | GAC | CTA | ACA | TCA | CGA | CCT | 144 |
| Gln | Asp | Ile | Ser | Leu | Lys | Phe | Phe | Glu | Ile | Asp | Leu | Thr | Ser | Arg | Pro | |
| | | | 35 | | | | | 40 | | | | | 45 | | | |
| GCT | CAT | GGA | GGA | AAG | ACA | GAG | CAA | GGC | TTA | AGT | CCA | AAA | TCA | AAA | CCA | 192 |
| Ala | His | Gly | Gly | Lys | Thr | Glu | Gln | Gly | Leu | Ser | Pro | Lys | Ser | Lys | Pro | |
| | | 50 | | | | | 55 | | | | | 60 | | | | |
| TTT | GCT | ACT | GAT | AGT | GGC | GCG | ATG | CCA | CAT | AAA | CTT | GAA | AAA | GCT | GAC | 240 |
| Phe | Ala | Thr | Asp | Ser | Gly | Ala | Met | Pro | His | Lys | Leu | Glu | Lys | Ala | Asp | |
| | 65 | | | | | 70 | | | | | 75 | | | | | |
| TTA | CTA | AAG | GCT | ATT | CAA | GAA | CAA | TTG | ATC | GCT | AAC | GTC | CAC | AGT | AAC | 288 |
| Leu | Leu | Lys | Ala | Ile | Gln | Glu | Gln | Leu | Ile | Ala | Asn | Val | His | Ser | Asn | |
| 80 | | | | | 85 | | | | | 90 | | | | | 95 | |
| GAC | GAC | TAC | TTT | GAG | GTC | ATT | GAT | TTT | GCA | AGC | GAT | GCA | ACC | ATT | ACT | 336 |
| Asp | Asp | Tyr | Phe | Glu | Val | Ile | Asp | Phe | Ala | Ser | Asp | Ala | Thr | Ile | Thr | |
| | | | | 100 | | | | | 105 | | | | | 110 | | |
| GAT | CGA | AAC | GGC | AAG | GTC | TAC | TTT | GCT | GAC | AAA | GAT | GGT | TCG | GTA | ACC | 384 |
| Asp | Arg | Asn | Gly | Lys | Val | Tyr | Phe | Ala | Asp | Lys | Asp | Gly | Ser | Val | Thr | |
| | | | 115 | | | | | 120 | | | | | 125 | | | |
| TTG | CCG | ACC | CAA | CCT | GTC | CAA | GAA | TTT | TTG | CTA | AGC | GGA | CAT | GTG | CGC | 432 |
| Leu | Pro | Thr | Gln | Pro | Val | Gln | Glu | Phe | Leu | Leu | Ser | Gly | His | Val | Arg | |
| | | 130 | | | | | 135 | | | | | 140 | | | | |
| GTT | AGA | CCA | TAT | AAA | GAA | AAA | CCA | ATA | CAA | AAT | CAA | GCG | AAA | TCT | GTT | 480 |
| Val | Arg | Pro | Tyr | Lys | Glu | Lys | Pro | Ile | Gln | Asn | Gln | Ala | Lys | Ser | Val | |
| | 145 | | | | | 150 | | | | | 155 | | | | | |
| GAT | GTG | GAA | TAT | ACT | GTA | CAG | TTT | ACT | CCC | TTA | AAC | CCT | GAT | GAC | GAT | 528 |
| Asp | Val | Glu | Tyr | Thr | Val | Gln | Phe | Thr | Pro | Leu | Asn | Pro | Asp | Asp | Asp | |
| 160 | | | | | 165 | | | | | 170 | | | | | 175 | |
| TTC | AGA | CCA | GGT | CTC | AAA | GAT | ACT | AAG | CTA | TTG | AAA | ACA | CTA | GCT | ATC | 576 |
| Phe | Arg | Pro | Gly | Leu | Lys | Asp | Thr | Lys | Leu | Leu | Lys | Thr | Leu | Ala | Ile | |
| | | | 180 | | | | | 185 | | | | | 190 | | | |
| GGT | GAC | ACC | ATC | ACA | TCT | CAA | GAA | TTA | CTA | GCT | CAA | GCA | CAA | AGC | ATT | 624 |
| Gly | Asp | Thr | Ile | Thr | Ser | Gln | Glu | Leu | Leu | Ala | Gln | Ala | Gln | Ser | Ile | |
| | | | 195 | | | | | 200 | | | | | 205 | | | |
| TTA | AAC | AAA | ACC | CAT | CCA | GGC | TAT | ACG | ATT | TAT | GAA | CGT | GAC | TCC | TCA | 672 |
| Leu | Asn | Lys | Thr | His | Pro | Gly | Tyr | Thr | Ile | Tyr | Glu | Arg | Asp | Ser | Ser | |
| | | 210 | | | | | 215 | | | | | 220 | | | | |
| ATC | GTC | ACT | CAT | GAC | AAT | GAC | ATT | TTC | CGT | ACG | ATT | TTA | CCA | ATG | GAT | 720 |
| Ile | Val | Thr | His | Asp | Asn | Asp | Ile | Phe | Arg | Thr | Ile | Leu | Pro | Met | Asp | |
| | 225 | | | | | 230 | | | | | 235 | | | | | |
| CAA | GAG | TTT | ACT | TAC | CAT | GTC | AAA | AAT | CGG | GAA | CAA | GCT | TAT | GAG | ATC | 768 |
| Gln | Glu | Phe | Thr | Tyr | His | Val | Lys | Asn | Arg | Glu | Gln | Ala | Tyr | Glu | Ile | |
| 240 | | | | | 245 | | | | | 250 | | | | | 255 | |
| AAT | AAA | AAA | TCT | GGT | CTG | AAT | GAA | GAA | ATA | AAC | AAC | ACT | GAC | CTG | ATC | 816 |
| Asn | Lys | Lys | Ser | Gly | Leu | Asn | Glu | Glu | Ile | Asn | Asn | Thr | Asp | Leu | Ile | |
| | | | 260 | | | | | 265 | | | | | 270 | | | |
| TCT | GAG | AAA | TAT | TAC | GTC | CTT | AAA | AAA | GGG | GAA | AAG | CCG | TAT | GAT | CCC | 864 |
| Ser | Glu | Lys | Tyr | Tyr | Val | Leu | Lys | Lys | Gly | Glu | Lys | Pro | Tyr | Asp | Pro | |
| | | | | 275 | | | | | 280 | | | | | 285 | | |
| TTT | GAT | CGC | AGT | CAC | TTG | AAA | CTG | TTC | ACC | ATC | AAA | TAC | GTT | GAT | GTC | 912 |
| Phe | Asp | Arg | Ser | His | Leu | Lys | Leu | Phe | Thr | Ile | Lys | Tyr | Val | Asp | Val | |
| | | 290 | | | | | 295 | | | | | 300 | | | | |

| | | |
|---|---|---|
| AAC ACC AAC GAA TTG CTA AAA AGC GAG CAG CTC TTA ACA GCT AGC GAA<br>Asn Thr Asn Glu Leu Leu Lys Ser Glu Gln Leu Leu Thr Ala Ser Glu<br>305                          310                            315 | | 960 |
| CGT AAC TTA GAC TTC AGA GAT TTA TAC GAT CCT CGT GAT AAG GCT AAA<br>Arg Asn Leu Asp Phe Arg Asp Leu Tyr Asp Pro Arg Asp Lys Ala Lys<br>320                        325                      330                    335 | | 1008 |
| CTA CTC TAC AAC AAT CTC GAT GCT TTT GGT ATT ATG GAC TAT ACC TTA<br>Leu Leu Tyr Asn Asn Leu Asp Ala Phe Gly Ile Met Asp Tyr Thr Leu<br>                    340                      345                    350 | | 1056 |
| ACT GGA AAA GTA GAA GAT AAT CAC GAT GAC ACC AAC CGT ATC ATA ACC<br>Thr Gly Lys Val Glu Asp Asn His Asp Asp Thr Asn Arg Ile Ile Thr<br>                  355                      360                    365 | | 1104 |
| GTT TAT ATG GGC AAG CGA CCC GAA GGA GAG AAT GCT AGC TAT CAT TTA<br>Val Tyr Met Gly Lys Arg Pro Glu Gly Glu Asn Ala Ser Tyr His Leu<br>        370                            375                    380 | | 1152 |
| GCC TAT GAT AAA GAT CGT TAT ACC GAA GAA GAA CGA GAA GTT TAC AGC<br>Ala Tyr Asp Lys Asp Arg Tyr Thr Glu Glu Glu Arg Glu Val Tyr Ser<br>385                        390                             395 | | 1200 |
| TAC CTG CGT TAT ACA GGG ACA CCT ATA CCT GAT AAC CCT AAC GAC AAA<br>Tyr Leu Arg Tyr Thr Gly Thr Pro Ile Pro Asp Asn Pro Asn Asp Lys<br>400                        405                      410                    415 | | 1248 |
| TAAGGATCC | | 1257 |

( 2 ) INFORMATION FOR SEQ ID NO:26:

( i ) SEQUENCE CHARACTERISTICS:
        ( A ) LENGTH: 415 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Met Ile Ala Gly Pro Glu Trp Leu Leu Asp Arg Pro Ser Val Asn Asn
 1               5                  10                  15

Ser Gln Leu Val Val Ser Val Ala Gly Thr Val Glu Gly Thr Asn Gln
                20                  25                  30

Asp Ile Ser Leu Lys Phe Phe Glu Ile Asp Leu Thr Ser Arg Pro Ala
                35                  40                  45

His Gly Gly Lys Thr Glu Gln Gly Leu Ser Pro Lys Ser Lys Pro Phe
         50                  55                  60

Ala Thr Asp Ser Gly Ala Met Pro His Lys Leu Glu Lys Ala Asp Leu
 65                  70                  75                  80

Leu Lys Ala Ile Gln Glu Gln Leu Ile Ala Asn Val His Ser Asn Asp
                85                  90                  95

Asp Tyr Phe Glu Val Ile Asp Phe Ala Ser Asp Ala Thr Ile Thr Asp
                100                 105                 110

Arg Asn Gly Lys Val Tyr Phe Ala Asp Lys Asp Gly Ser Val Thr Leu
            115                 120                 125

Pro Thr Gln Pro Val Gln Glu Phe Leu Leu Ser Gly His Val Arg Val
    130                 135                 140

Arg Pro Tyr Lys Glu Lys Pro Ile Gln Asn Gln Ala Lys Ser Val Asp
145                 150                 155                 160

Val Glu Tyr Thr Val Gln Phe Thr Pro Leu Asn Pro Asp Asp Asp Phe
                165                 170                 175

Arg Pro Gly Leu Lys Asp Thr Lys Leu Leu Lys Thr Leu Ala Ile Gly
                180                 185                 190

Asp Thr Ile Thr Ser Gln Glu Leu Leu Ala Gln Ala Gln Ser Ile Leu
            195                 200                 205

Asn Lys Thr His Pro Gly Tyr Thr Ile Tyr Glu Arg Asp Ser Ser Ile
```

|     |     |     |     | 210 |     |     |     |     | 215 |     |     |     |     | 220 |     |
| --- | --- | --- | --- | --- | --- | --- | --- | --- | --- | --- | --- | --- | --- | --- | --- |
| Val | Thr | His | Asp | Asn | Asp | Ile | Phe | Arg | Thr | Ile | Leu | Pro | Met | Asp | Gln |
| 225 |     |     |     | 230 |     |     |     |     | 235 |     |     |     |     | 240 |     |
| Glu | Phe | Thr | Tyr | His | Val | Lys | Asn | Arg | Glu | Gln | Ala | Tyr | Glu | Ile | Asn |
|     |     |     |     | 245 |     |     |     |     | 250 |     |     |     |     | 255 |     |
| Lys | Lys | Ser | Gly | Leu | Asn | Glu | Glu | Ile | Asn | Asn | Thr | Asp | Leu | Ile | Ser |
|     |     |     |     | 260 |     |     |     |     | 265 |     |     |     |     | 270 |     |
| Glu | Lys | Tyr | Tyr | Val | Leu | Lys | Lys | Gly | Glu | Lys | Pro | Tyr | Asp | Pro | Phe |
|     |     |     | 275 |     |     |     |     | 280 |     |     |     |     | 285 |     |     |
| Asp | Arg | Ser | His | Leu | Lys | Leu | Phe | Thr | Ile | Lys | Tyr | Val | Asp | Val | Asn |
|     |     | 290 |     |     |     |     | 295 |     |     |     |     | 300 |     |     |     |
| Thr | Asn | Glu | Leu | Leu | Lys | Ser | Glu | Gln | Leu | Leu | Thr | Ala | Ser | Glu | Arg |
| 305 |     |     |     |     | 310 |     |     |     |     | 315 |     |     |     |     | 320 |
| Asn | Leu | Asp | Phe | Arg | Asp | Leu | Tyr | Asp | Pro | Arg | Asp | Lys | Ala | Lys | Leu |
|     |     |     |     | 325 |     |     |     |     | 330 |     |     |     |     | 335 |     |
| Leu | Tyr | Asn | Asn | Leu | Asp | Ala | Phe | Gly | Ile | Met | Asp | Tyr | Thr | Leu | Thr |
|     |     |     | 340 |     |     |     |     | 345 |     |     |     |     | 350 |     |     |
| Gly | Lys | Val | Glu | Asp | Asn | His | Asp | Asp | Thr | Asn | Arg | Ile | Ile | Thr | Val |
|     |     | 355 |     |     |     |     | 360 |     |     |     |     | 365 |     |     |     |
| Tyr | Met | Gly | Lys | Arg | Pro | Glu | Gly | Glu | Asn | Ala | Ser | Tyr | His | Leu | Ala |
|     | 370 |     |     |     |     | 375 |     |     |     |     | 380 |     |     |     |     |
| Tyr | Asp | Lys | Asp | Arg | Tyr | Thr | Glu | Glu | Glu | Arg | Glu | Val | Tyr | Ser | Tyr |
| 385 |     |     |     |     | 390 |     |     |     |     | 395 |     |     |     |     | 400 |
| Leu | Arg | Tyr | Thr | Gly | Thr | Pro | Ile | Pro | Asp | Asn | Pro | Asn | Asp | Lys |     |
|     |     |     |     | 405 |     |     |     |     | 410 |     |     |     |     | 415 |     |

( 2 ) INFORMATION FOR SEQ ID NO:27:

( i ) SEQUENCE CHARACTERISTICS:
        ( A ) LENGTH: 1512 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..1512
        ( D ) OTHER INFORMATION: /note="Streptokinase
        fused to a yeast alpha-factor"

( i x ) FEATURE:
        ( A ) NAME/KEY: CDS
        ( B ) LOCATION: 7..1503

( i x ) FEATURE:
        ( A ) NAME/KEY: mat_peptide
        ( B ) LOCATION: 7..1503

( x i ) SEQUENCE DESCRIPTION: SEQ ID NO:27:

| AGATCT | ATG | AGA | TTT | CCT | TCA | ATT | TTT | ACT | GCA | GTT | TTA | TTC | GCA | GCA |     | 48 |
| --- | --- | --- | --- | --- | --- | --- | --- | --- | --- | --- | --- | --- | --- | --- | --- | --- |
|     | Met | Arg | Phe | Pro | Ser | Ile | Phe | Thr | Ala | Val | Leu | Phe | Ala | Ala |     |    |
|     | 1   |     |     | 5   |     |     |     |     | 10  |     |     |     |     |     |     |    |
| TCC | TCC | GCA | TTA | GCT | GCT | CCA | GTC | AAC | ACT | ACA | ACA | GAA | GAT | GAA | ACG | 96 |
| Ser | Ser | Ala | Leu | Ala | Ala | Pro | Val | Asn | Thr | Thr | Thr | Glu | Asp | Glu | Thr |    |
| 15  |     |     |     | 20  |     |     |     |     | 25  |     |     |     |     | 30  |     |    |
| GCA | CAA | ATT | CCG | GCT | GAA | GCT | GTC | ATC | GGT | TAC | TTA | GAT | TTA | GAA | GGG | 144 |
| Ala | Gln | Ile | Pro | Ala | Glu | Ala | Val | Ile | Gly | Tyr | Leu | Asp | Leu | Glu | Gly |    |
|     |     |     |     | 35  |     |     |     |     | 40  |     |     |     |     | 45  |     |    |
| GAT | TTC | GAT | GTT | GCT | GTT | TTG | CCA | TTT | TCC | AAC | AGC | ACA | AAT | AAC | GGG | 192 |
| Asp | Phe | Asp | Val | Ala | Val | Leu | Pro | Phe | Ser | Asn | Ser | Thr | Asn | Asn | Gly |    |
|     |     |     | 50  |     |     |     |     | 55  |     |     |     |     | 60  |     |     |    |
| TTA | TTG | TTT | ATA | AAT | ACT | ACT | ATT | GCC | AGC | ATT | GCT | GCT | AAA | GAA | GAA | 240 |

| | | | | | | | | | | | | | | | | |
|---|---|---|---|---|---|---|---|---|---|---|---|---|---|---|---|---|
|Leu|Leu|Phe|Ile|Asn|Thr|Thr|Ile|Ala|Ser|Ile|Ala|Ala|Lys|Glu|Glu| |
| | |65| | | | |70| | | | |75| | | | |

```
GGG GTA AGC TTG GAT AAA AGA ATT GCT GGA CCT GAG TGG CTG CTA GAC     288
Gly Val Ser Leu Asp Lys Arg Ile Ala Gly Pro Glu Trp Leu Leu Asp
     80              85                  90

CGT CCA TCT GTC AAC AAC AGC CAA TTA GTT GTT AGC GTT GCT GGT ACT     336
Arg Pro Ser Val Asn Asn Ser Gln Leu Val Val Ser Val Ala Gly Thr
 95             100             105                 110

GTT GAG GGG ACG AAT CAA GAC ATT AGT CTT AAA TTT TTT GAA ATT GAC     384
Val Glu Gly Thr Asn Gln Asp Ile Ser Leu Lys Phe Phe Glu Ile Asp
                115             120                 125

CTA ACA TCA CGA CCT GCT CAT GGA GGA AAG ACA GAG CAA GGC TTA AGT     432
Leu Thr Ser Arg Pro Ala His Gly Gly Lys Thr Glu Gln Gly Leu Ser
            130             135                 140

CCA AAA TCA AAA CCA TTT GCT ACT GAT AGT GGC GCG ATG CCA CAT AAA     480
Pro Lys Ser Lys Pro Phe Ala Thr Asp Ser Gly Ala Met Pro His Lys
        145             150                 155

CTT GAA AAA GCT GAC TTA CTA AAG GCT ATT CAA GAA CAA TTG ATC GCT     528
Leu Glu Lys Ala Asp Leu Leu Lys Ala Ile Gln Glu Gln Leu Ile Ala
    160             165                 170

AAC GTC CAC AGT AAC GAC GAC TAC TTT GAG GTC ATT GAT TTT GCA AGC     576
Asn Val His Ser Asn Asp Asp Tyr Phe Glu Val Ile Asp Phe Ala Ser
175             180                 185                 190

GAT GCA ACC ATT ACT GAT CGA AAC GGC AAG GTC TAC TTT GCT GAC AAA     624
Asp Ala Thr Ile Thr Asp Arg Asn Gly Lys Val Tyr Phe Ala Asp Lys
            195                 200                 205

GAT GGT TCG GTA ACC TTG CCG ACC CAA CCT GTC CAA GAA TTT TTG CTA     672
Asp Gly Ser Val Thr Leu Pro Thr Gln Pro Val Gln Glu Phe Leu Leu
        210                 215                 220

AGC GGA CAT GTG CGC GTT AGA CCA TAT AAA GAA AAA CCA ATA CAA AAT     720
Ser Gly His Val Arg Val Arg Pro Tyr Lys Glu Lys Pro Ile Gln Asn
            225             230                 235

CAA GCG AAA TCT GTT GAT GTG GAA TAT ACT GTA CAG TTT ACT CCC TTA     768
Gln Ala Lys Ser Val Asp Val Glu Tyr Thr Val Gln Phe Thr Pro Leu
    240             245                 250

AAC CCT GAT GAC GAT TTC AGA CCA GGT CTC AAA GAT ACT AAG CTA TTG     816
Asn Pro Asp Asp Asp Phe Arg Pro Gly Leu Lys Asp Thr Lys Leu Leu
255             260                 265                 270

AAA ACA CTA GCT ATC GGT GAC ACC ATC ACA TCT CAA GAA TTA CTA GCT     864
Lys Thr Leu Ala Ile Gly Asp Thr Ile Thr Ser Gln Glu Leu Leu Ala
            275             280                 285

CAA GCA CAA AGC ATT TTA AAC AAA ACC CAT CCA GGC TAT ACG ATT TAT     912
Gln Ala Gln Ser Ile Leu Asn Lys Thr His Pro Gly Tyr Thr Ile Tyr
        290             295                 300

GAA CGT GAC TCC TCA ATC GTC ACT CAT GAC AAT GAC ATT TTC CGT ACG     960
Glu Arg Asp Ser Ser Ile Val Thr His Asp Asn Asp Ile Phe Arg Thr
        305             310                 315

ATT TTA CCA ATG GAT CAA GAG TTT ACT TAC CAT GTC AAA AAT CGG GAA    1008
Ile Leu Pro Met Asp Gln Glu Phe Thr Tyr His Val Lys Asn Arg Glu
    320             325                 330

CAA GCT TAT GAG ATC AAT AAA AAA TCT GGT CTG AAT GAA GAA ATA AAC    1056
Gln Ala Tyr Glu Ile Asn Lys Lys Ser Gly Leu Asn Glu Glu Ile Asn
335             340                 345                 350

AAC ACT GAC CTG ATC TCT GAG AAA TAT TAC GTC CTT AAA AAA GGG GAA    1104
Asn Thr Asp Leu Ile Ser Glu Lys Tyr Tyr Val Leu Lys Lys Gly Glu
            355             360                 365

AAG CCG TAT GAT CCC TTT GAT CGC AGT CAC TTG AAA CTG TTC ACC ATC    1152
Lys Pro Tyr Asp Pro Phe Asp Arg Ser His Leu Lys Leu Phe Thr Ile
        370             375                 380

AAA TAC GTT GAT GTC AAC ACC AAC GAA TTG CTA AAA AGC GAG CAG CTC    1200
Lys Tyr Val Asp Val Asn Thr Asn Glu Leu Leu Lys Ser Glu Gln Leu
            385             390                 395
```

| | | | | | | | | | | | | | | | |
|---|---|---|---|---|---|---|---|---|---|---|---|---|---|---|---|
|TTA|ACA|GCT|AGC|GAA|CGT|AAC|TTA|GAC|TTC|AGA|GAT|TTA|TAC|GAT|CCT|
|Leu|Thr|Ala|Ser|Glu|Arg|Asn|Leu|Asp|Phe|Arg|Asp|Leu|Tyr|Asp|Pro|
| |400| | | |405| | | | |410| | | | | |

1248

| | | | | | | | | | | | | | | | |
|---|---|---|---|---|---|---|---|---|---|---|---|---|---|---|---|
|CGT|GAT|AAG|GCT|AAA|CTA|CTC|TAC|AAC|AAT|CTC|GAT|GCT|TTT|GGT|ATT|
|Arg|Asp|Lys|Ala|Lys|Leu|Leu|Tyr|Asn|Asn|Leu|Asp|Ala|Phe|Gly|Ile|
|415| | | |420| | | | |425| | | | | |430|

1296

| | | | | | | | | | | | | | | | |
|---|---|---|---|---|---|---|---|---|---|---|---|---|---|---|---|
|ATG|GAC|TAT|ACC|TTA|ACT|GGA|AAA|GTA|GAA|GAT|AAT|CAC|GAT|GAC|ACC|
|Met|Asp|Tyr|Thr|Leu|Thr|Gly|Lys|Val|Glu|Asp|Asn|His|Asp|Asp|Thr|
| | | | |435| | | |440| | | | |445| | |

1344

| | | | | | | | | | | | | | | | |
|---|---|---|---|---|---|---|---|---|---|---|---|---|---|---|---|
|AAC|CGT|ATC|ATA|ACC|GTT|TAT|ATG|GGC|AAG|CGA|CCC|GAA|GGA|GAG|AAT|
|Asn|Arg|Ile|Ile|Thr|Val|Tyr|Met|Gly|Lys|Arg|Pro|Glu|Gly|Glu|Asn|
| | | |450| | | |455| | | | |460| | | |

1392

| | | | | | | | | | | | | | | | |
|---|---|---|---|---|---|---|---|---|---|---|---|---|---|---|---|
|GCT|AGC|TAT|CAT|TTA|GCC|TAT|GAT|AAA|GAT|CGT|TAT|ACC|GAA|GAA|GAA|
|Ala|Ser|Tyr|His|Leu|Ala|Tyr|Asp|Lys|Asp|Arg|Tyr|Thr|Glu|Glu|Glu|
| | |465| | | |470| | | |475| | | | | |

1440

| | | | | | | | | | | | | | | | |
|---|---|---|---|---|---|---|---|---|---|---|---|---|---|---|---|
|CGA|GAA|GTT|TAC|AGC|TAC|CTG|CGT|TAT|ACA|GGG|ACA|CCT|ATA|CCT|GAT|
|Arg|Glu|Val|Tyr|Ser|Tyr|Leu|Arg|Tyr|Thr|Gly|Thr|Pro|Ile|Pro|Asp|
| |480| | | |485| | | | |490| | | | | |

1488

| | | | | |
|---|---|---|---|---|
|AAC|CCT|AAC|GAC|AAA|TAAGGATCC|
|Asn|Pro|Asn|Asp|Lys|
|495| | | | |

1512

( 2 ) INFORMATION FOR SEQ ID NO:28:

( i ) SEQUENCE CHARACTERISTICS:
        ( A ) LENGTH: 499 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

| | | | | | | | | | | | | | | |
|---|---|---|---|---|---|---|---|---|---|---|---|---|---|---|
|Met|Arg|Phe|Pro|Ser|Ile|Phe|Thr|Ala|Val|Leu|Phe|Ala|Ala|Ser|Ser|
|1| | | |5| | | | |10| | | | |15|

| | | | | | | | | | | | | | | |
|---|---|---|---|---|---|---|---|---|---|---|---|---|---|---|
|Ala|Leu|Ala|Ala|Pro|Val|Asn|Thr|Thr|Thr|Glu|Asp|Glu|Thr|Ala|Gln|
| | | |20| | | | |25| | | | |30| | |

| | | | | | | | | | | | | | | |
|---|---|---|---|---|---|---|---|---|---|---|---|---|---|---|
|Ile|Pro|Ala|Glu|Ala|Val|Ile|Gly|Tyr|Leu|Asp|Leu|Glu|Gly|Asp|Phe|
| | |35| | | | |40| | | | |45| | | |

| | | | | | | | | | | | | | | |
|---|---|---|---|---|---|---|---|---|---|---|---|---|---|---|
|Asp|Val|Ala|Val|Leu|Pro|Phe|Ser|Asn|Ser|Thr|Asn|Asn|Gly|Leu|Leu|
| |50| | | | |55| | | | |60| | | | |

| | | | | | | | | | | | | | | |
|---|---|---|---|---|---|---|---|---|---|---|---|---|---|---|
|Phe|Ile|Asn|Thr|Thr|Ile|Ala|Ser|Ile|Ala|Ala|Lys|Glu|Glu|Gly|Val|
|65| | | | |70| | | | |75| | | | |80|

| | | | | | | | | | | | | | | |
|---|---|---|---|---|---|---|---|---|---|---|---|---|---|---|
|Ser|Leu|Asp|Lys|Arg|Ile|Ala|Gly|Pro|Glu|Trp|Leu|Leu|Asp|Arg|Pro|
| | | | |85| | | | |90| | | | |95|

| | | | | | | | | | | | | | | |
|---|---|---|---|---|---|---|---|---|---|---|---|---|---|---|
|Ser|Val|Asn|Asn|Ser|Gln|Leu|Val|Val|Ser|Val|Ala|Gly|Thr|Val|Glu|
| | | | |100| | | | |105| | | | |110|

| | | | | | | | | | | | | | | |
|---|---|---|---|---|---|---|---|---|---|---|---|---|---|---|
|Gly|Thr|Asn|Gln|Asp|Ile|Ser|Leu|Lys|Phe|Phe|Glu|Ile|Asp|Leu|Thr|
| | | |115| | | | |120| | | | |125| | |

| | | | | | | | | | | | | | | |
|---|---|---|---|---|---|---|---|---|---|---|---|---|---|---|
|Ser|Arg|Pro|Ala|His|Gly|Gly|Lys|Thr|Glu|Gln|Gly|Leu|Ser|Pro|Lys|
| | |130| | | | |135| | | | |140| | | |

| | | | | | | | | | | | | | | |
|---|---|---|---|---|---|---|---|---|---|---|---|---|---|---|
|Ser|Lys|Pro|Phe|Ala|Thr|Asp|Ser|Gly|Ala|Met|Pro|His|Lys|Leu|Glu|
|145| | | | |150| | | | |155| | | | |160|

| | | | | | | | | | | | | | | |
|---|---|---|---|---|---|---|---|---|---|---|---|---|---|---|
|Lys|Ala|Asp|Leu|Leu|Lys|Ala|Ile|Gln|Glu|Gln|Leu|Ile|Ala|Asn|Val|
| | | | |165| | | | |170| | | | |175|

| | | | | | | | | | | | | | | |
|---|---|---|---|---|---|---|---|---|---|---|---|---|---|---|
|His|Ser|Asn|Asp|Asp|Tyr|Phe|Glu|Val|Ile|Asp|Phe|Ala|Ser|Asp|Ala|
| | | |180| | | | |185| | | | |190| | |

| | | | | | | | | | | | | | | |
|---|---|---|---|---|---|---|---|---|---|---|---|---|---|---|
|Thr|Ile|Thr|Asp|Arg|Asn|Gly|Lys|Val|Tyr|Phe|Ala|Asp|Lys|Asp|Gly|
| | |195| | | | |200| | | | |205| | | |

| | | | | | | | | | | | | | | |
|---|---|---|---|---|---|---|---|---|---|---|---|---|---|---|
|Ser|Val|Thr|Leu|Pro|Thr|Gln|Pro|Val|Gln|Glu|Phe|Leu|Leu|Ser|Gly|
| |210| | | | |215| | | | |220| | | | |

| | | | | | | | | | | | | | | |
|---|---|---|---|---|---|---|---|---|---|---|---|---|---|---|
|His|Val|Arg|Val|Arg|Pro|Tyr|Lys|Glu|Lys|Pro|Ile|Gln|Asn|Gln|Ala|
|225| | | |230| | | |235| | | |240|

His Val Arg Val Arg Pro Tyr Lys Glu Lys Pro Ile Gln Asn Gln Ala
225                     230                 235                 240

Lys Ser Val Asp Val Glu Tyr Thr Val Gln Phe Thr Pro Leu Asn Pro
                245                 250                 255

Asp Asp Asp Phe Arg Pro Gly Leu Lys Asp Thr Lys Leu Leu Lys Thr
            260                 265                 270

Leu Ala Ile Gly Asp Thr Ile Thr Ser Gln Glu Leu Leu Ala Gln Ala
        275                 280                 285

Gln Ser Ile Leu Asn Lys His Pro Gly Tyr Thr Ile Tyr Glu Arg
    290                 295                 300

Asp Ser Ser Ile Val Thr His Asp Asn Asp Ile Phe Arg Thr Ile Leu
305                 310                 315                 320

Pro Met Asp Gln Glu Phe Thr Tyr His Val Lys Asn Arg Glu Gln Ala
            325                 330                 335

Tyr Glu Ile Asn Lys Lys Ser Gly Leu Asn Glu Glu Ile Asn Asn Thr
            340                 345                 350

Asp Leu Ile Ser Glu Lys Tyr Tyr Val Leu Lys Lys Gly Glu Lys Pro
        355                 360                 365

Tyr Asp Pro Phe Asp Arg Ser His Leu Lys Leu Phe Thr Ile Lys Tyr
    370                 375                 380

Val Asp Val Asn Thr Asn Glu Leu Leu Lys Ser Glu Gln Leu Leu Thr
385                 390                 395                 400

Ala Ser Glu Arg Asn Leu Asp Phe Arg Asp Leu Tyr Asp Pro Arg Asp
            405                 410                 415

Lys Ala Lys Leu Leu Tyr Asn Asn Leu Asp Ala Phe Gly Ile Met Asp
            420                 425                 430

Tyr Thr Leu Thr Gly Lys Val Glu Asp Asn His Asp Asp Thr Asn Arg
        435                 440                 445

Ile Ile Thr Val Tyr Met Gly Lys Arg Pro Glu Gly Glu Asn Ala Ser
    450                 455                 460

Tyr His Leu Ala Tyr Asp Lys Asp Arg Tyr Thr Glu Glu Glu Arg Glu
465                 470                 475                 480

Val Tyr Ser Tyr Leu Arg Tyr Thr Gly Thr Pro Ile Pro Asp Asn Pro
            485                 490                 495

Asn Asp Lys ( 2 ) INFORMATION FOR SEQ ID NO:29:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..36
        ( D ) OTHER INFORMATION: /note="oligonucleotide BB3624"

( x i ) SEQUENCE DESCRIPTION: SEQ ID NO:29:

GTCCAAGCTA AGCTTGGATA AAGAATTGC TGGACC     36

( 2 ) INFORMATION FOR SEQ ID NO:30:

( i ) SEQUENCE CHARACTERISTICS:
        ( A ) LENGTH: 1119 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
    ( A ) NAME/KEY: misc_feature
    ( B ) LOCATION: 1..1119
    ( D ) OTHER INFORMATION: /note="Truncated Met-streptokinase
        (a a 16-383)"

( i x ) FEATURE:
    ( A ) NAME/KEY: CDS
    ( B ) LOCATION: 4..1110

( i x ) FEATURE:
    ( A ) NAME/KEY: mat_peptide
    ( B ) LOCATION: 4..1110

( x i ) SEQUENCE DESCRIPTION: SEQ ID NO:30:

```
CAT ATG AGC CAA TTA GTT GTT AGC GTT GCT GGT ACT GTT GAG GGG ACG        48
    Met Ser Gln Leu Val Val Ser Val Ala Gly Thr Val Glu Gly Thr
    1           5                   10                  15

AAT CAA GAC ATT AGT CTT AAA TTT TTT GAA ATT GAC CTA ACA TCA CGA        96
Asn Gln Asp Ile Ser Leu Lys Phe Phe Glu Ile Asp Leu Thr Ser Arg
                20                  25                  30

CCT GCT CAT GGA GGA AAG ACA GAG CAA GGC TTA AGT CCA AAA TCA AAA       144
Pro Ala His Gly Gly Lys Thr Glu Gln Gly Leu Ser Pro Lys Ser Lys
            35                  40                  45

CCA TTT GCT ACT GAT AGT GGC GCG ATG CCA CAT AAA CTT GAA AAA GCT       192
Pro Phe Ala Thr Asp Ser Gly Ala Met Pro His Lys Leu Glu Lys Ala
        50                  55                  60

GAC TTA CTA AAG GCT ATT CAA GAA CAA TTG ATC GCT AAC GTC CAC AGT       240
Asp Leu Leu Lys Ala Ile Gln Glu Gln Leu Ile Ala Asn Val His Ser
    65                  70                  75

AAC GAC GAC TAC TTT GAG GTC ATT GAT TTT GCA AGC GAT GCA ACC ATT       288
Asn Asp Asp Tyr Phe Glu Val Ile Asp Phe Ala Ser Asp Ala Thr Ile
80                  85                  90                  95

ACT GAT CGA AAC GGC AAG GTC TAC TTT GCT GAC AAA GAT GGT TCG GTA       336
Thr Asp Arg Asn Gly Lys Val Tyr Phe Ala Asp Lys Asp Gly Ser Val
                100                 105                 110

ACC TTG CCG ACC CAA CCT GTC CAA GAA TTT TTG CTA AGC GGA CAT GTG       384
Thr Leu Pro Thr Gln Pro Val Gln Glu Phe Leu Leu Ser Gly His Val
            115                 120                 125

CGC GTT AGA CCA TAT AAA GAA AAA CCA ATA CAA AAT CAA GCG AAA TCT       432
Arg Val Arg Pro Tyr Lys Glu Lys Pro Ile Gln Asn Gln Ala Lys Ser
        130                 135                 140

GTT GAT GTG GAA TAT ACT GTA CAG TTT ACT CCC TTA AAC CCT GAT GAC       480
Val Asp Val Glu Tyr Thr Val Gln Phe Thr Pro Leu Asn Pro Asp Asp
    145                 150                 155

GAT TTC AGA CCA GGT CTC AAA GAT ACT AAG CTA TTG AAA ACA CTA GCT       528
Asp Phe Arg Pro Gly Leu Lys Asp Thr Lys Leu Leu Lys Thr Leu Ala
160                 165                 170                 175

ATC GGT GAC ACC ATC ACA TCT CAA GAA TTA CTA GCT CAA GCA CAA AGC       576
Ile Gly Asp Thr Ile Thr Ser Gln Glu Leu Leu Ala Gln Ala Gln Ser
                180                 185                 190

ATT TTA AAC AAA ACC CAT CCA GGC TAT ACG ATT TAT GAA CGT GAC TCC       624
Ile Leu Asn Lys Thr His Pro Gly Tyr Thr Ile Tyr Glu Arg Asp Ser
            195                 200                 205

TCA ATC GTC ACT CAT GAC AAT GAC ATT TTC CGT ACG ATT TTA CCA ATG       672
Ser Ile Val Thr His Asp Asn Asp Ile Phe Arg Thr Ile Leu Pro Met
        210                 215                 220

GAT CAA GAG TTT ACT TAC CAT GTC AAA AAT CGG GAA CAA GCT TAT GAG       720
Asp Gln Glu Phe Thr Tyr His Val Lys Asn Arg Glu Gln Ala Tyr Glu
    225                 230                 235

ATC AAT AAA AAA TCT GGT CTG AAT GAA GAA ATA AAC AAC ACT GAC CTG       768
Ile Asn Lys Lys Ser Gly Leu Asn Glu Glu Ile Asn Asn Thr Asp Leu
240                 245                 250                 255
```

| | | | | | | | | | | | | | | | | |
|---|---|---|---|---|---|---|---|---|---|---|---|---|---|---|---|---|
| ATC | TCT | GAG | AAA | TAT | TAC | GTC | CTT | AAA | AAA | GGG | GAA | AAG | CCG | TAT | GAT | 816 |
| Ile | Ser | Glu | Lys | Tyr | Tyr | Val | Leu | Lys | Lys | Gly | Glu | Lys | Pro | Tyr | Asp | |
| | | | | 260 | | | | | 265 | | | | | 270 | | |
| CCC | TTT | GAT | CGC | AGT | CAC | TTG | AAA | CTG | TTC | ACC | ATC | AAA | TAC | GTT | GAT | 864 |
| Pro | Phe | Asp | Arg | Ser | His | Leu | Lys | Leu | Phe | Thr | Ile | Lys | Tyr | Val | Asp | |
| | | | 275 | | | | | 280 | | | | | 285 | | | |
| GTC | AAC | ACC | AAC | GAA | TTG | CTA | AAA | AGC | GAG | CAG | CTC | TTA | ACA | GCT | AGC | 912 |
| Val | Asn | Thr | Asn | Glu | Leu | Leu | Lys | Ser | Glu | Gln | Leu | Leu | Thr | Ala | Ser | |
| | | 290 | | | | | 295 | | | | | 300 | | | | |
| GAA | CGT | AAC | TTA | GAC | TTC | AGA | GAT | TTA | TAC | GAT | CCT | CGT | GAT | AAG | GCT | 960 |
| Glu | Arg | Asn | Leu | Asp | Phe | Arg | Asp | Leu | Tyr | Asp | Pro | Arg | Asp | Lys | Ala | |
| | 305 | | | | | 310 | | | | | 315 | | | | | |
| AAA | CTA | CTC | TAC | AAC | AAT | CTC | GAT | GCT | TTT | GGT | ATT | ATG | GAC | TAT | ACC | 1008 |
| Lys | Leu | Leu | Tyr | Asn | Asn | Leu | Asp | Ala | Phe | Gly | Ile | Met | Asp | Tyr | Thr | |
| 320 | | | | | 325 | | | | | 330 | | | | | 335 | |
| TTA | ACT | GGA | AAA | GTA | GAA | GAT | AAT | CAC | GAT | GAC | ACC | AAC | CGT | ATC | ATA | 1056 |
| Leu | Thr | Gly | Lys | Val | Glu | Asp | Asn | His | Asp | Asp | Thr | Asn | Arg | Ile | Ile | |
| | | | | 340 | | | | | 345 | | | | | 350 | | |
| ACC | GTT | TAT | ATG | GGC | AAG | CGA | CCC | GAA | GGA | GAG | AAT | GCT | AGC | TAT | CAT | 1104 |
| Thr | Val | Tyr | Met | Gly | Lys | Arg | Pro | Glu | Gly | Glu | Asn | Ala | Ser | Tyr | His | |
| | | | 355 | | | | | 360 | | | | | 365 | | | |
| TTA | GCC | TAAGGATCC | | | | | | | | | | | | | | 1119 |
| Leu | Ala | | | | | | | | | | | | | | | |

( 2 ) INFORMATION FOR SEQ ID NO:31:

( i ) SEQUENCE CHARACTERISTICS:
        ( A ) LENGTH: 369 amino acids
        ( B ) TYPE: amino acid
        ( D ) TOPOLOGY: linear ( i i ) MOLECULE TYPE: protein ( x i ) SEQUENCE DESCRIPTION: SEQ ID NO:31:

| | | | | | | | | | | | | | | |
|---|---|---|---|---|---|---|---|---|---|---|---|---|---|---|
| Met | Ser | Gln | Leu | Val | Val | Ser | Val | Ala | Gly | Thr | Val | Glu | Gly | Thr | Asn |
| 1 | | | | 5 | | | | | 10 | | | | | 15 | |
| Gln | Asp | Ile | Ser | Leu | Lys | Phe | Phe | Glu | Ile | Asp | Leu | Thr | Ser | Arg | Pro |
| | | | 20 | | | | | 25 | | | | | 30 | | |
| Ala | His | Gly | Gly | Lys | Thr | Glu | Gln | Gly | Leu | Ser | Pro | Lys | Ser | Lys | Pro |
| | | 35 | | | | | 40 | | | | | 45 | | | |
| Phe | Ala | Thr | Asp | Ser | Gly | Ala | Met | Pro | His | Lys | Leu | Glu | Lys | Ala | Asp |
| | 50 | | | | | 55 | | | | | 60 | | | | |
| Leu | Leu | Lys | Ala | Ile | Gln | Glu | Gln | Leu | Ile | Ala | Asn | Val | His | Ser | Asn |
| 65 | | | | | 70 | | | | | 75 | | | | | 80 |
| Asp | Asp | Tyr | Phe | Glu | Val | Ile | Asp | Phe | Ala | Ser | Asp | Ala | Thr | Ile | Thr |
| | | | | 85 | | | | | 90 | | | | | 95 | |
| Asp | Arg | Asn | Gly | Lys | Val | Tyr | Phe | Ala | Asp | Lys | Asp | Gly | Ser | Val | Thr |
| | | | 100 | | | | | 105 | | | | | 110 | | |
| Leu | Pro | Thr | Gln | Pro | Val | Gln | Glu | Phe | Leu | Leu | Ser | Gly | His | Val | Arg |
| | | 115 | | | | | 120 | | | | | 125 | | | |
| Val | Arg | Pro | Tyr | Lys | Glu | Lys | Pro | Ile | Gln | Asn | Gln | Ala | Lys | Ser | Val |
| | 130 | | | | | 135 | | | | | 140 | | | | |
| Asp | Val | Glu | Tyr | Thr | Val | Gln | Phe | Thr | Pro | Leu | Asn | Pro | Asp | Asp | Asp |
| 145 | | | | | 150 | | | | | 155 | | | | | 160 |
| Phe | Arg | Pro | Gly | Leu | Lys | Asp | Thr | Lys | Leu | Leu | Lys | Thr | Leu | Ala | Ile |
| | | | | 165 | | | | | 170 | | | | | 175 | |
| Gly | Asp | Thr | Ile | Thr | Ser | Gln | Glu | Leu | Leu | Ala | Gln | Ala | Gln | Ser | Ile |
| | | | 180 | | | | | 185 | | | | | 190 | | |
| Leu | Asn | Lys | Thr | His | Pro | Gly | Tyr | Thr | Ile | Tyr | Glu | Arg | Asp | Ser | Ser |
| | | 195 | | | | | 200 | | | | | 205 | | | |

| | | | | | | | | | | | | | |
|---|---|---|---|---|---|---|---|---|---|---|---|---|---|
| Ile | Val 210 | Thr | His | Asp | Asn 215 | Asp | Ile | Phe | Arg | Thr 220 | Ile | Leu | Pro | Met | Asp |
| Gln 225 | Glu | Phe | Thr | Tyr | His 230 | Val | Lys | Asn | Arg | Glu 235 | Gln | Ala | Tyr | Glu | Ile 240 |
| Asn | Lys | Lys | Ser | Gly 245 | Leu | Asn | Glu | Glu | Ile 250 | Asn | Asn | Thr | Asp | Leu 255 | Ile |
| Ser | Glu | Lys | Tyr 260 | Tyr | Val | Leu | Lys | Lys 265 | Gly | Glu | Lys | Pro | Tyr 270 | Asp | Pro |
| Phe | Asp | Arg 275 | Ser | His | Leu | Lys | Leu 280 | Phe | Thr | Ile | Lys | Tyr 285 | Val | Asp | Val |
| Asn | Thr 290 | Asn | Glu | Leu | Leu | Lys 295 | Ser | Glu | Gln | Leu | Leu 300 | Thr | Ala | Ser | Glu |
| Arg 305 | Asn | Leu | Asp | Phe | Arg 310 | Asp | Leu | Tyr | Asp | Pro 315 | Arg | Asp | Lys | Ala | Lys 320 |
| Leu | Leu | Tyr | Asn | Asn 325 | Leu | Asp | Ala | Phe | Gly 330 | Ile | Met | Asp | Tyr | Thr 335 | Leu |
| Thr | Gly | Lys | Val 340 | Glu | Asp | Asn | His | Asp 345 | Asp | Thr | Asn | Arg | Ile 350 | Ile | Thr |
| Val | Tyr | Met 355 | Gly | Lys | Arg | Pro | Glu 360 | Gly | Glu | Asn | Ala | Ser 365 | Tyr | His | Leu |
| Ala | | | | | | | | | | | | | | | |

( 2 ) INFORMATION FOR SEQ ID NO:32:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..33
        ( D ) OTHER INFORMATION: /note="oligonucleotide BB3862"

( x i ) SEQUENCE DESCRIPTION: SEQ ID NO:32:

GAAATACTTA CATATGAGCC AATTAGTTGT TAG     33

( 2 ) INFORMATION FOR SEQ ID NO:33:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..28
        ( D ) OTHER INFORMATION: /note="oligonucleotide BB3904"

( x i ) SEQUENCE DESCRIPTION: SEQ ID NO:33:

CCCGGGGATC CTTAGGCTAA ATGATAGC     28

( 2 ) INFORMATION FOR SEQ ID NO:34:

( i ) SEQUENCE CHARACTERISTICS:
        ( A ) LENGTH: 2589 base pairs
        ( B ) TYPE: nucleic acid
        ( C ) STRANDEDNESS: single
        ( D ) TOPOLOGY: linear (i i) MOLECULE TYPE: cDNA (i x) FEATURE:
    (A) NAME/KEY: misc_feature
    (B) LOCATION: 1..2589
    (D) OTHER INFORMATION: /note=
    " OmpAL-Streptokinase-streptokinase fusion linked
    by thrombin- cleavable VELQGVVPRG"

(i x) FEATURE:
    (A) NAME/KEY: CDS
    (B) LOCATION: 4..2580

(i x) FEATURE:
    (A) NAME/KEY: mat_peptide
    (B) LOCATION: 4..2580

(x i) SEQUENCE DESCRIPTION: SEQ ID NO:34:

| | | | | | | | | | | | | | | | | |
|---|---|---|---|---|---|---|---|---|---|---|---|---|---|---|---|---|
| CAT | ATG | AAA | AAG | ACA | GCT | ATC | GCG | ATT | GCA | GTG | GCA | CTG | GCT | GGT | TTC | 48 |
| | Met | Lys | Lys | Thr | Ala | Ile | Ala | Ile | Ala | Val | Ala | Leu | Ala | Gly | Phe | |
| | 1 | | | | 5 | | | | | 10 | | | | | 15 | |
| GCG | ACC | GTA | GCG | CAG | GCC | ATT | GCT | GGA | CCT | GAG | TGG | CTG | CTA | GAC | CGT | 96 |
| Ala | Thr | Val | Ala | Gln | Ala | Ile | Ala | Gly | Pro | Glu | Trp | Leu | Leu | Asp | Arg | |
| | | | | 20 | | | | | 25 | | | | | 30 | | |
| CCA | TCT | GTC | AAC | AAC | AGC | CAA | TTA | GTT | GTT | AGC | GTT | GCT | GGT | ACT | GTT | 144 |
| Pro | Ser | Val | Asn | Asn | Ser | Gln | Leu | Val | Val | Ser | Val | Ala | Gly | Thr | Val | |
| | | | 35 | | | | | 40 | | | | | 45 | | | |
| GAG | GGG | ACG | AAT | CAA | GAC | ATT | AGT | CTT | AAA | TTT | TTT | GAA | ATT | GAC | CTA | 192 |
| Glu | Gly | Thr | Asn | Gln | Asp | Ile | Ser | Leu | Lys | Phe | Phe | Glu | Ile | Asp | Leu | |
| | | 50 | | | | | 55 | | | | | 60 | | | | |
| ACA | TCA | CGA | CCT | GCT | CAT | GGA | GGA | AAG | ACA | GAG | CAA | GGC | TTA | AGT | CCA | 240 |
| Thr | Ser | Arg | Pro | Ala | His | Gly | Gly | Lys | Thr | Glu | Gln | Gly | Leu | Ser | Pro | |
| | 65 | | | | | 70 | | | | | 75 | | | | | |
| AAA | TCA | AAA | CCA | TTT | GCT | ACT | GAT | AGT | GGC | GCG | ATG | CCA | CAT | AAA | CTT | 288 |
| Lys | Ser | Lys | Pro | Phe | Ala | Thr | Asp | Ser | Gly | Ala | Met | Pro | His | Lys | Leu | |
| 80 | | | | | 85 | | | | | 90 | | | | | 95 | |
| GAA | AAA | GCT | GAC | TTA | CTA | AAG | GCT | ATT | CAA | GAA | CAA | TTG | ATC | GCT | AAC | 336 |
| Glu | Lys | Ala | Asp | Leu | Leu | Lys | Ala | Ile | Gln | Glu | Gln | Leu | Ile | Ala | Asn | |
| | | | | 100 | | | | | 105 | | | | | 110 | | |
| GTC | CAC | AGT | AAC | GAC | GAC | TAC | TTT | GAG | GTC | ATT | GAT | TTT | GCA | AGC | GAT | 384 |
| Val | His | Ser | Asn | Asp | Asp | Tyr | Phe | Glu | Val | Ile | Asp | Phe | Ala | Ser | Asp | |
| | | | 115 | | | | | 120 | | | | | 125 | | | |
| GCA | ACC | ATT | ACT | GAT | CGA | AAC | GGC | AAG | GTC | TAC | TTT | GCT | GAC | AAA | GAT | 432 |
| Ala | Thr | Ile | Thr | Asp | Arg | Asn | Gly | Lys | Val | Tyr | Phe | Ala | Asp | Lys | Asp | |
| | | 130 | | | | | 135 | | | | | 140 | | | | |
| GGT | TCG | GTA | ACC | TTG | CCG | ACC | CAA | CCT | GTC | CAA | GAA | TTT | TTG | CTA | AGC | 480 |
| Gly | Ser | Val | Thr | Leu | Pro | Thr | Gln | Pro | Val | Gln | Glu | Phe | Leu | Leu | Ser | |
| | 145 | | | | | 150 | | | | | 155 | | | | | |
| GGA | CAT | GTG | CGC | GTT | AGA | CCA | TAT | AAA | GAA | AAA | CCA | ATA | CAA | AAT | CAA | 528 |
| Gly | His | Val | Arg | Val | Arg | Pro | Tyr | Lys | Glu | Lys | Pro | Ile | Gln | Asn | Gln | |
| 160 | | | | | 165 | | | | | 170 | | | | | 175 | |
| GCG | AAA | TCT | GTT | GAT | GTG | GAA | TAT | ACT | GTA | CAG | TTT | ACT | CCC | TTA | AAC | 576 |
| Ala | Lys | Ser | Val | Asp | Val | Glu | Tyr | Thr | Val | Gln | Phe | Thr | Pro | Leu | Asn | |
| | | | | 180 | | | | | 185 | | | | | 190 | | |
| CCT | GAT | GAC | GAT | TTC | AGA | CCA | GGT | CTC | AAA | GAT | ACT | AAG | CTA | TTG | AAA | 624 |
| Pro | Asp | Asp | Asp | Phe | Arg | Pro | Gly | Leu | Lys | Asp | Thr | Lys | Leu | Leu | Lys | |
| | | | 195 | | | | | 200 | | | | | 205 | | | |
| ACA | CTA | GCT | ATC | GGT | GAC | ACC | ATC | ACA | TCT | CAA | GAA | TTA | CTA | GCT | CAA | 672 |
| Thr | Leu | Ala | Ile | Gly | Asp | Thr | Ile | Thr | Ser | Gln | Glu | Leu | Leu | Ala | Gln | |
| | | 210 | | | | | 215 | | | | | 220 | | | | |
| GCA | CAA | AGC | ATT | TTA | AAC | AAA | ACC | CAT | CCA | GGC | TAT | ACG | ATT | TAT | GAA | 720 |
| Ala | Gln | Ser | Ile | Leu | Asn | Lys | Thr | His | Pro | Gly | Tyr | Thr | Ile | Tyr | Glu | |
| | 225 | | | | | 230 | | | | | 235 | | | | | |
| CGT | GAC | TCC | TCA | ATC | GTC | ACT | CAT | GAC | AAT | GAC | ATT | TTC | CGT | ACG | ATT | 768 |
| Arg | Asp | Ser | Ser | Ile | Val | Thr | His | Asp | Asn | Asp | Ile | Phe | Arg | Thr | Ile | |
| 240 | | | | | 245 | | | | | 250 | | | | | 255 | |

| | | | | | | | | | | | | | | | | |
|---|---|---|---|---|---|---|---|---|---|---|---|---|---|---|---|---|
| TTA | CCA | ATG | GAT | CAA | GAG | TTT | ACT | TAC | CAT | GTC | AAA | AAT | CGG | GAA | CAA | 816 |
| Leu | Pro | Met | Asp | Gln | Glu | Phe | Thr | Tyr | His | Val | Lys | Asn | Arg | Glu | Gln | |
| | | | | 260 | | | | | 265 | | | | | 270 | | |
| GCT | TAT | GAG | ATC | AAT | AAA | AAA | TCT | GGT | CTG | AAT | GAA | GAA | ATA | AAC | AAC | 864 |
| Ala | Tyr | Glu | Ile | Asn | Lys | Lys | Ser | Gly | Leu | Asn | Glu | Glu | Ile | Asn | Asn | |
| | | | 275 | | | | | 280 | | | | | 285 | | | |
| ACT | GAC | CTG | ATC | TCT | GAG | AAA | TAT | TAC | GTC | CTT | AAA | AAA | GGG | GAA | AAG | 912 |
| Thr | Asp | Leu | Ile | Ser | Glu | Lys | Tyr | Tyr | Val | Leu | Lys | Lys | Gly | Glu | Lys | |
| | | | 290 | | | | 295 | | | | | 300 | | | | |
| CCG | TAT | GAT | CCC | TTT | GAT | CGC | AGT | CAC | TTG | AAA | CTG | TTC | ACC | ATC | AAA | 960 |
| Pro | Tyr | Asp | Pro | Phe | Asp | Arg | Ser | His | Leu | Lys | Leu | Phe | Thr | Ile | Lys | |
| | 305 | | | | | 310 | | | | | 315 | | | | | |
| TAC | GTT | GAT | GTC | AAC | ACC | AAC | GAA | TTG | CTA | AAA | AGC | GAG | CAG | CTC | TTA | 1008 |
| Tyr | Val | Asp | Val | Asn | Thr | Asn | Glu | Leu | Leu | Lys | Ser | Glu | Gln | Leu | Leu | |
| 320 | | | | | 325 | | | | | 330 | | | | | 335 | |
| ACA | GCT | AGC | GAA | CGT | AAC | TTA | GAC | TTC | AGA | GAT | TTA | TAC | GAT | CCT | CGT | 1056 |
| Thr | Ala | Ser | Glu | Arg | Asn | Leu | Asp | Phe | Arg | Asp | Leu | Tyr | Asp | Pro | Arg | |
| | | | | 340 | | | | | 345 | | | | | 350 | | |
| GAT | AAG | GCT | AAA | CTA | CTC | TAC | AAC | AAT | CTC | GAT | GCT | TTT | GGT | ATT | ATG | 1104 |
| Asp | Lys | Ala | Lys | Leu | Leu | Tyr | Asn | Asn | Leu | Asp | Ala | Phe | Gly | Ile | Met | |
| | | | 355 | | | | | 360 | | | | | 365 | | | |
| GAC | TAT | ACC | TTA | ACT | GGA | AAA | GTA | GAA | GAT | AAT | CAC | GAT | GAC | ACC | AAC | 1152 |
| Asp | Tyr | Thr | Leu | Thr | Gly | Lys | Val | Glu | Asp | Asn | His | Asp | Asp | Thr | Asn | |
| | | 370 | | | | | 375 | | | | | 380 | | | | |
| CGT | ATC | ATA | ACC | GTT | TAT | ATG | GGC | AAG | CGA | CCC | GAA | GGA | GAG | AAT | GCT | 1200 |
| Arg | Ile | Ile | Thr | Val | Tyr | Met | Gly | Lys | Arg | Pro | Glu | Gly | Glu | Asn | Ala | |
| | 385 | | | | | 390 | | | | | 395 | | | | | |
| AGC | TAT | CAT | TTA | GCC | TAT | GAT | AAA | GAT | CGT | TAT | ACC | GAA | GAA | GAA | CGA | 1248 |
| Ser | Tyr | His | Leu | Ala | Tyr | Asp | Lys | Asp | Arg | Tyr | Thr | Glu | Glu | Glu | Arg | |
| 400 | | | | | 405 | | | | | 410 | | | | | 415 | |
| GAA | GTT | TAC | AGC | TAC | CTG | CGT | TAT | ACA | GGG | ACA | CCT | ATA | CCT | GAT | AAC | 1296 |
| Glu | Val | Tyr | Ser | Tyr | Leu | Arg | Tyr | Thr | Gly | Thr | Pro | Ile | Pro | Asp | Asn | |
| | | | | 420 | | | | | 425 | | | | | 430 | | |
| CCT | AAC | GAC | AAA | GTA | GAG | CTG | CAG | GGA | GTA | GTT | CCT | CGT | GGA | ATT | GCT | 1344 |
| Pro | Asn | Asp | Lys | Val | Glu | Leu | Gln | Gly | Val | Val | Pro | Arg | Gly | Ile | Ala | |
| | | | 435 | | | | | 440 | | | | | 445 | | | |
| GGA | CCT | GAG | TGG | CTG | CTA | GAC | CGT | CCA | TCT | GTC | AAC | AAC | AGC | CAA | TTA | 1392 |
| Gly | Pro | Glu | Trp | Leu | Leu | Asp | Arg | Pro | Ser | Val | Asn | Asn | Ser | Gln | Leu | |
| | | 450 | | | | | 455 | | | | | 460 | | | | |
| GTT | GTT | AGC | GTT | GCT | GGT | ACT | GTT | GAG | GGG | ACG | AAT | CAA | GAC | ATT | AGT | 1440 |
| Val | Val | Ser | Val | Ala | Gly | Thr | Val | Glu | Gly | Thr | Asn | Gln | Asp | Ile | Ser | |
| | 465 | | | | | 470 | | | | | 475 | | | | | |
| CTT | AAA | TTT | TTT | GAA | ATT | GAC | CTA | ACA | TCA | CGA | CCT | GCT | CAT | GGA | GGA | 1488 |
| Leu | Lys | Phe | Phe | Glu | Ile | Asp | Leu | Thr | Ser | Arg | Pro | Ala | His | Gly | Gly | |
| 480 | | | | | 485 | | | | | 490 | | | | | 495 | |
| AAG | ACA | GAG | CAA | GGC | TTA | AGT | CCA | AAA | TCA | AAA | CCA | TTT | GCT | ACT | GAT | 1536 |
| Lys | Thr | Glu | Gln | Gly | Leu | Ser | Pro | Lys | Ser | Lys | Pro | Phe | Ala | Thr | Asp | |
| | | | | 500 | | | | | 505 | | | | | 510 | | |
| AGT | GGC | GCG | ATG | CCA | CAT | AAA | CTT | GAA | AAA | GCT | GAC | TTA | CTA | AAG | GCT | 1584 |
| Ser | Gly | Ala | Met | Pro | His | Lys | Leu | Glu | Lys | Ala | Asp | Leu | Leu | Lys | Ala | |
| | | | 515 | | | | | 520 | | | | | 525 | | | |
| ATT | CAA | GAA | CAA | TTG | ATC | GCT | AAC | GTC | CAC | AGT | AAC | GAC | GAC | TAC | TTT | 1632 |
| Ile | Gln | Glu | Gln | Leu | Ile | Ala | Asn | Val | His | Ser | Asn | Asp | Asp | Tyr | Phe | |
| | | 530 | | | | | 535 | | | | | 540 | | | | |
| GAG | GTC | ATT | GAT | TTT | GCA | AGC | GAT | GCA | ACC | ATT | ACT | GAT | CGA | AAC | GGC | 1680 |
| Glu | Val | Ile | Asp | Phe | Ala | Ser | Asp | Ala | Thr | Ile | Thr | Asp | Arg | Asn | Gly | |
| | 545 | | | | | 550 | | | | | 555 | | | | | |
| AAG | GTC | TAC | TTT | GCT | GAC | AAA | GAT | GGT | TCG | GTA | ACC | TTG | CCG | ACC | CAA | 1728 |
| Lys | Val | Tyr | Phe | Ala | Asp | Lys | Asp | Gly | Ser | Val | Thr | Leu | Pro | Thr | Gln | |
| 560 | | | | | 565 | | | | | 570 | | | | | 575 | |
| CCT | GTC | CAA | GAA | TTT | TTG | CTA | AGC | GGA | CAT | GTG | CGC | GTT | AGA | CCA | TAT | 1776 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Pro | Val | Gln | Glu | Phe | Leu | Leu | Ser | Gly | His | Val | Arg | Val | Arg | Pro | Tyr |      |
|     |     |     | 580 |     |     |     |     | 585 |     |     |     |     |     | 590 |     |      |
| AAA | GAA | AAA | CCA | ATA | CAA | AAT | CAA | GCG | AAA | TCT | GTT | GAT | GTG | GAA | TAT | 1824 |
| Lys | Glu | Lys | Pro | Ile | Gln | Asn | Gln | Ala | Lys | Ser | Val | Asp | Val | Glu | Tyr |      |
|     |     |     | 595 |     |     |     |     | 600 |     |     |     |     | 605 |     |     |      |
| ACT | GTA | CAG | TTT | ACT | CCC | TTA | AAC | CCT | GAT | GAC | GAT | TTC | AGA | CCA | GGT | 1872 |
| Thr | Val | Gln | Phe | Thr | Pro | Leu | Asn | Pro | Asp | Asp | Asp | Phe | Arg | Pro | Gly |      |
|     |     | 610 |     |     |     |     | 615 |     |     |     |     | 620 |     |     |     |      |
| CTC | AAA | GAT | ACT | AAG | CTA | TTG | AAA | ACA | CTA | GCT | ATC | GGT | GAC | ACC | ATC | 1920 |
| Leu | Lys | Asp | Thr | Lys | Leu | Leu | Lys | Thr | Leu | Ala | Ile | Gly | Asp | Thr | Ile |      |
|     | 625 |     |     |     |     | 630 |     |     |     |     | 635 |     |     |     |     |      |
| ACA | TCT | CAA | GAA | TTA | CTA | GCT | CAA | GCA | CAA | AGC | ATT | TTA | AAC | AAA | ACC | 1968 |
| Thr | Ser | Gln | Glu | Leu | Leu | Ala | Gln | Ala | Gln | Ser | Ile | Leu | Asn | Lys | Thr |      |
| 640 |     |     |     | 645 |     |     |     |     | 650 |     |     |     |     |     | 655 |      |
| CAT | CCA | GGC | TAT | ACG | ATT | TAT | GAA | CGT | GAC | TCC | TCA | ATC | GTC | ACT | CAT | 2016 |
| His | Pro | Gly | Tyr | Thr | Ile | Tyr | Glu | Arg | Asp | Ser | Ser | Ile | Val | Thr | His |      |
|     |     |     | 660 |     |     |     |     | 665 |     |     |     |     |     | 670 |     |      |
| GAC | AAT | GAC | ATT | TTC | CGT | ACG | ATT | TTA | CCA | ATG | GAT | CAA | GAG | TTT | ACT | 2064 |
| Asp | Asn | Asp | Ile | Phe | Arg | Thr | Ile | Leu | Pro | Met | Asp | Gln | Glu | Phe | Thr |      |
|     |     |     | 675 |     |     |     |     | 680 |     |     |     |     | 685 |     |     |      |
| TAC | CAT | GTC | AAA | AAT | CGG | GAA | CAA | GCT | TAT | GAG | ATC | AAT | AAA | AAA | TCT | 2112 |
| Tyr | His | Val | Lys | Asn | Arg | Glu | Gln | Ala | Tyr | Glu | Ile | Asn | Lys | Lys | Ser |      |
|     |     | 690 |     |     |     |     | 695 |     |     |     |     | 700 |     |     |     |      |
| GGT | CTG | AAT | GAA | GAA | ATA | AAC | AAC | ACT | GAC | CTG | ATC | TCT | GAG | AAA | TAT | 2160 |
| Gly | Leu | Asn | Glu | Glu | Ile | Asn | Asn | Thr | Asp | Leu | Ile | Ser | Glu | Lys | Tyr |      |
|     | 705 |     |     |     |     | 710 |     |     |     |     | 715 |     |     |     |     |      |
| TAC | GTC | CTT | AAA | AAA | GGG | GAA | AAG | CCG | TAT | GAT | CCC | TTT | GAT | CGC | AGT | 2208 |
| Tyr | Val | Leu | Lys | Lys | Gly | Glu | Lys | Pro | Tyr | Asp | Pro | Phe | Asp | Arg | Ser |      |
| 720 |     |     |     |     | 725 |     |     |     |     | 730 |     |     |     |     | 735 |      |
| CAC | TTG | AAA | CTG | TTC | ACC | ATC | AAA | TAC | GTT | GAT | GTC | AAC | ACC | AAC | GAA | 2256 |
| His | Leu | Lys | Leu | Phe | Thr | Ile | Lys | Tyr | Val | Asp | Val | Asn | Thr | Asn | Glu |      |
|     |     |     |     | 740 |     |     |     |     | 745 |     |     |     |     | 750 |     |      |
| TTG | CTA | AAA | AGC | GAG | CAG | CTC | TTA | ACA | GCT | AGC | GAA | CGT | AAC | TTA | GAC | 2304 |
| Leu | Leu | Lys | Ser | Glu | Gln | Leu | Leu | Thr | Ala | Ser | Glu | Arg | Asn | Leu | Asp |      |
|     |     |     | 755 |     |     |     |     | 760 |     |     |     |     | 765 |     |     |      |
| TTC | AGA | GAT | TTA | TAC | GAT | CCT | CGT | GAT | AAG | GCT | AAA | CTA | CTC | TAC | AAC | 2352 |
| Phe | Arg | Asp | Leu | Tyr | Asp | Pro | Arg | Asp | Lys | Ala | Lys | Leu | Leu | Tyr | Asn |      |
|     |     | 770 |     |     |     |     | 775 |     |     |     |     | 780 |     |     |     |      |
| AAT | CTC | GAT | GCT | TTT | GGT | ATT | ATG | GAC | TAT | ACC | TTA | ACT | GGA | AAA | GTA | 2400 |
| Asn | Leu | Asp | Ala | Phe | Gly | Ile | Met | Asp | Tyr | Thr | Leu | Thr | Gly | Lys | Val |      |
|     | 785 |     |     |     |     | 790 |     |     |     |     | 795 |     |     |     |     |      |
| GAA | GAT | AAT | CAC | GAT | GAC | ACC | AAC | CGT | ATC | ATA | ACC | GTT | TAT | ATG | GGC | 2448 |
| Glu | Asp | Asn | His | Asp | Asp | Thr | Asn | Arg | Ile | Ile | Thr | Val | Tyr | Met | Gly |      |
| 800 |     |     |     |     | 805 |     |     |     |     | 810 |     |     |     |     | 815 |      |
| AAG | CGA | CCC | GAA | GGA | GAG | AAT | GCT | AGC | TAT | CAT | TTA | GCC | TAT | GAT | AAA | 2496 |
| Lys | Arg | Pro | Glu | Gly | Glu | Asn | Ala | Ser | Tyr | His | Leu | Ala | Tyr | Asp | Lys |      |
|     |     |     |     | 820 |     |     |     |     | 825 |     |     |     |     | 830 |     |      |
| GAT | CGT | TAT | ACC | GAA | GAA | GAA | CGA | GAA | GTT | TAC | AGC | TAC | CTG | CGT | TAT | 2544 |
| Asp | Arg | Tyr | Thr | Glu | Glu | Glu | Arg | Glu | Val | Tyr | Ser | Tyr | Leu | Arg | Tyr |      |
|     |     |     | 835 |     |     |     |     | 840 |     |     |     |     | 845 |     |     |      |
| ACA | GGG | ACA | CCT | ATA | CCT | GAT | AAC | CCT | AAC | GAC | AAA | TAAGGATCC |   |   |   | 2589 |
| Thr | Gly | Thr | Pro | Ile | Pro | Asp | Asn | Pro | Asn | Asp | Lys |     |     |     |     |      |
|     |     | 850 |     |     |     |     | 855 |     |     |     |     |     |     |     |     |      |

( 2 ) INFORMATION FOR SEQ ID NO:35:

( i ) SEQUENCE CHARACTERISTICS:
        ( A ) LENGTH: 859 amino acids
        ( B ) TYPE: amino acid
        ( D ) TOPOLOGY: linear ( i i ) MOLECULE TYPE: protein ( x i ) SEQUENCE DESCRIPTION: SEQ ID NO:35:

| | | | | | | | | | | | | | | |
|---|---|---|---|---|---|---|---|---|---|---|---|---|---|---|
| Met<br>1 | Lys | Lys | Thr | Ala<br>5 | Ile | Ala | Ile | Ala | Val<br>10 | Ala | Leu | Ala | Gly | Phe<br>15 | Ala |
| Thr | Val | Ala | Gln<br>20 | Ala | Ile | Ala | Gly | Pro<br>25 | Glu | Trp | Leu | Leu | Asp<br>30 | Arg | Pro |
| Ser | Val | Asn<br>35 | Asn | Ser | Gln | Leu | Val<br>40 | Val | Ser | Val | Ala | Gly<br>45 | Thr | Val | Glu |
| Gly | Thr<br>50 | Asn | Gln | Asp | Ile | Ser<br>55 | Leu | Lys | Phe | Phe | Glu<br>60 | Ile | Asp | Leu | Thr |
| Ser<br>65 | Arg | Pro | Ala | His | Gly<br>70 | Gly | Lys | Thr | Glu | Gln<br>75 | Gly | Leu | Ser | Pro | Lys<br>80 |
| Ser | Lys | Pro | Phe | Ala<br>85 | Thr | Asp | Ser | Gly | Ala<br>90 | Met | Pro | His | Lys | Leu<br>95 | Glu |
| Lys | Ala | Asp | Leu<br>100 | Leu | Lys | Ala | Ile | Gln<br>105 | Glu | Gln | Leu | Ile | Ala<br>110 | Asn | Val |
| His | Ser | Asn<br>115 | Asp | Asp | Tyr | Phe | Glu<br>120 | Val | Ile | Asp | Phe | Ala<br>125 | Ser | Asp | Ala |
| Thr | Ile<br>130 | Thr | Asp | Arg | Asn | Gly<br>135 | Lys | Val | Tyr | Phe | Ala<br>140 | Asp | Lys | Asp | Gly |
| Ser<br>145 | Val | Thr | Leu | Pro | Thr<br>150 | Gln | Pro | Val | Gln | Glu<br>155 | Phe | Leu | Leu | Ser | Gly<br>160 |
| His | Val | Arg | Val | Arg<br>165 | Pro | Tyr | Lys | Glu | Lys<br>170 | Pro | Ile | Gln | Asn | Gln<br>175 | Ala |
| Lys | Ser | Val | Asp<br>180 | Val | Glu | Tyr | Thr | Val<br>185 | Gln | Phe | Thr | Pro | Leu<br>190 | Asn | Pro |
| Asp | Asp | Asp<br>195 | Phe | Arg | Pro | Gly | Leu<br>200 | Lys | Asp | Thr | Lys | Leu<br>205 | Leu | Lys | Thr |
| Leu | Ala<br>210 | Ile | Gly | Asp | Thr | Ile<br>215 | Thr | Ser | Gln | Glu | Leu<br>220 | Leu | Ala | Gln | Ala |
| Gln<br>225 | Ser | Ile | Leu | Asn | Lys<br>230 | Thr | His | Pro | Gly | Tyr<br>235 | Thr | Ile | Tyr | Glu | Arg<br>240 |
| Asp | Ser | Ser | Ile | Val<br>245 | Thr | His | Asp | Asn | Asp<br>250 | Ile | Phe | Arg | Thr | Ile<br>255 | Leu |
| Pro | Met | Asp | Gln<br>260 | Glu | Phe | Thr | Tyr | His<br>265 | Val | Lys | Asn | Arg | Glu<br>270 | Gln | Ala |
| Tyr | Glu | Ile<br>275 | Asn | Lys | Lys | Ser | Gly<br>280 | Leu | Asn | Glu | Glu | Ile<br>285 | Asn | Asn | Thr |
| Asp | Leu<br>290 | Ile | Ser | Glu | Lys | Tyr<br>295 | Tyr | Val | Leu | Lys | Lys<br>300 | Gly | Glu | Lys | Pro |
| Tyr<br>305 | Asp | Pro | Phe | Asp | Arg<br>310 | Ser | His | Leu | Lys | Leu<br>315 | Phe | Thr | Ile | Lys | Tyr<br>320 |
| Val | Asp | Val | Asn | Thr<br>325 | Asn | Glu | Leu | Leu | Lys<br>330 | Ser | Glu | Gln | Leu | Leu<br>335 | Thr |
| Ala | Ser | Glu | Arg<br>340 | Asn | Leu | Asp | Phe | Arg<br>345 | Asp | Leu | Tyr | Asp | Pro<br>350 | Arg | Asp |
| Lys | Ala | Lys<br>355 | Leu | Leu | Tyr | Asn | Asn<br>360 | Leu | Asp | Ala | Phe | Gly<br>365 | Ile | Met | Asp |
| Tyr | Thr<br>370 | Leu | Thr | Gly | Lys | Val<br>375 | Glu | Asp | Asn | His | Asp<br>380 | Asp | Thr | Asn | Arg |
| Ile<br>385 | Ile | Thr | Val | Tyr | Met<br>390 | Gly | Lys | Arg | Pro | Glu<br>395 | Gly | Glu | Asn | Ala | Ser<br>400 |
| Tyr | His | Leu | Ala | Tyr<br>405 | Asp | Lys | Asp | Arg | Tyr<br>410 | Thr | Glu | Glu | Glu | Arg<br>415 | Glu |
| Val | Tyr | Ser | Tyr<br>420 | Leu | Arg | Tyr | Thr | Gly<br>425 | Thr | Pro | Ile | Pro | Asp<br>430 | Asn | Pro |

```
Asn Asp Lys Val Glu Leu Gln Gly Val Val Pro Arg Gly Ile Ala Gly
        435                 440                 445
Pro Glu Trp Leu Leu Asp Arg Pro Ser Val Asn Asn Ser Gln Leu Val
        450                 455                 460
Val Ser Val Ala Gly Thr Val Glu Gly Thr Asn Gln Asp Ile Ser Leu
465                 470                 475                 480
Lys Phe Phe Glu Ile Asp Leu Thr Ser Arg Pro Ala His Gly Gly Lys
                485                 490                 495
Thr Glu Gln Gly Leu Ser Pro Lys Ser Lys Pro Phe Ala Thr Asp Ser
            500                 505                 510
Gly Ala Met Pro His Lys Leu Glu Lys Ala Asp Leu Leu Lys Ala Ile
            515                 520                 525
Gln Glu Gln Leu Ile Ala Asn Val His Ser Asn Asp Asp Tyr Phe Glu
        530                 535                 540
Val Ile Asp Phe Ala Ser Asp Ala Thr Ile Thr Asp Arg Asn Gly Lys
545                 550                 555                 560
Val Tyr Phe Ala Asp Lys Asp Gly Ser Val Thr Leu Pro Thr Gln Pro
                565                 570                 575
Val Gln Glu Phe Leu Leu Ser Gly His Val Arg Val Arg Pro Tyr Lys
            580                 585                 590
Glu Lys Pro Ile Gln Asn Gln Ala Lys Ser Val Asp Val Glu Tyr Thr
        595                 600                 605
Val Gln Phe Thr Pro Leu Asn Pro Asp Asp Phe Arg Pro Gly Leu
610                 615                 620
Lys Asp Thr Lys Leu Leu Lys Thr Leu Ala Ile Gly Asp Thr Ile Thr
625                 630                 635                 640
Ser Gln Glu Leu Leu Ala Gln Ala Gln Ser Ile Leu Asn Lys Thr His
                645                 650                 655
Pro Gly Tyr Thr Ile Tyr Glu Arg Asp Ser Ser Ile Val Thr His Asp
            660                 665                 670
Asn Asp Ile Phe Arg Thr Ile Leu Pro Met Asp Gln Glu Phe Thr Tyr
            675                 680                 685
His Val Lys Asn Arg Glu Gln Ala Tyr Glu Ile Asn Lys Lys Ser Gly
        690                 695                 700
Leu Asn Glu Glu Ile Asn Asn Thr Asp Leu Ile Ser Glu Lys Tyr Tyr
705                 710                 715                 720
Val Leu Lys Lys Gly Glu Lys Pro Tyr Asp Pro Phe Asp Arg Ser His
                725                 730                 735
Leu Lys Leu Phe Thr Ile Lys Tyr Val Asp Val Asn Thr Asn Glu Leu
            740                 745                 750
Leu Lys Ser Glu Gln Leu Leu Thr Ala Ser Glu Arg Asn Leu Asp Phe
            755                 760                 765
Arg Asp Leu Tyr Asp Pro Arg Asp Lys Ala Lys Leu Leu Tyr Asn Asn
        770                 775                 780
Leu Asp Ala Phe Gly Ile Met Asp Tyr Thr Leu Thr Gly Lys Val Glu
785                 790                 795                 800
Asp Asn His Asp Asp Thr Asn Arg Ile Ile Thr Val Tyr Met Gly Lys
                805                 810                 815
Arg Pro Glu Gly Glu Asn Ala Ser Tyr His Leu Ala Tyr Asp Lys Asp
            820                 825                 830
Arg Tyr Thr Glu Glu Glu Arg Glu Val Tyr Ser Tyr Leu Arg Tyr Thr
            835                 840                 845
Gly Thr Pro Ile Pro Asp Asn Pro Asn Asp Lys
            850                 855
```

( 2 ) INFORMATION FOR SEQ ID NO:36:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..63
        ( D ) OTHER INFORMATION: /note="oligonucleotide BB2938"

( x i ) SEQUENCE DESCRIPTION: SEQ ID NO:36:

```
GATAACCCTA ACGACAAAGT AGAGCTGCAG GGAGTAGTTC CTCGTGGAAT TGCTGGACCT      60

GAG                                                                   63
```

( 2 ) INFORMATION FOR SEQ ID NO:37:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..17
        ( D ) OTHER INFORMATION: /note="oligonucleotide BB2754"

( x i ) SEQUENCE DESCRIPTION: SEQ ID NO:37:

```
GCTATCGGTG ACACCAT                                                    17
```

( 2 ) INFORMATION FOR SEQ ID NO:38:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..17
        ( D ) OTHER INFORMATION: /note="oligonucleotide BB3639"

( x i ) SEQUENCE DESCRIPTION: SEQ ID NO:38:

```
GCTGCAGGGA GTAGTTC                                                    17
```

( 2 ) INFORMATION FOR SEQ ID NO:39:

( i ) SEQUENCE CHARACTERISTICS:
        ( A ) LENGTH: 2253 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..2253
        ( D ) OTHER INFORMATION: /note=
            " Met-corestreptokinase-corestreptokinase fusion
            linked by thrombin-cleavable VELQGVVPRG"

( i x ) FEATURE:
        ( A ) NAME/KEY: CDS
        ( B ) LOCATION: 4..2244

( i x ) FEATURE:
    ( A ) NAME/KEY: mat_peptide
    ( B ) LOCATION: 4..2244

( x i ) SEQUENCE DESCRIPTION: SEQ ID NO:39:

```
CAT ATG AGC CAA TTA GTT GTT AGC GTT GCT GGT ACT GTT GAG GGG ACG        48
    Met Ser Gln Leu Val Val Ser Val Ala Gly Thr Val Glu Gly Thr
    1               5                   10                  15

AAT CAA GAC ATT AGT CTT AAA TTT TTT GAA ATT GAC CTA ACA TCA CGA        96
Asn Gln Asp Ile Ser Leu Lys Phe Phe Glu Ile Asp Leu Thr Ser Arg
                20                  25                  30

CCT GCT CAT GGA GGA AAG ACA GAG CAA GGC TTA AGT CCA AAA TCA AAA       144
Pro Ala His Gly Gly Lys Thr Glu Gln Gly Leu Ser Pro Lys Ser Lys
            35                  40                  45

CCA TTT GCT ACT GAT AGT GGC GCG ATG CCA CAT AAA CTT GAA AAA GCT       192
Pro Phe Ala Thr Asp Ser Gly Ala Met Pro His Lys Leu Glu Lys Ala
        50                  55                  60

GAC TTA CTA AAG GCT ATT CAA GAA CAA TTG ATC GCT AAC GTC CAC AGT       240
Asp Leu Leu Lys Ala Ile Gln Glu Gln Leu Ile Ala Asn Val His Ser
    65                  70                  75

AAC GAC GAC TAC TTT GAG GTC ATT GAT TTT GCA AGC GAT GCA ACC ATT       288
Asn Asp Asp Tyr Phe Glu Val Ile Asp Phe Ala Ser Asp Ala Thr Ile
80                  85                  90                  95

ACT GAT CGA AAC GGC AAG GTC TAC TTT GCT GAC AAA GAT GGT TCG GTA       336
Thr Asp Arg Asn Gly Lys Val Tyr Phe Ala Asp Lys Asp Gly Ser Val
                100                 105                 110

ACC TTG CCG ACC CAA CCT GTC CAA GAA TTT TTG CTA AGC GGA CAT GTG       384
Thr Leu Pro Thr Gln Pro Val Gln Glu Phe Leu Leu Ser Gly His Val
            115                 120                 125

CGC GTT AGA CCA TAT AAA GAA AAA CCA ATA CAA AAT CAA GCG AAA TCT       432
Arg Val Arg Pro Tyr Lys Glu Lys Pro Ile Gln Asn Gln Ala Lys Ser
        130                 135                 140

GTT GAT GTG GAA TAT ACT GTA CAG TTT ACT CCC TTA AAC CCT GAT GAC       480
Val Asp Val Glu Tyr Thr Val Gln Phe Thr Pro Leu Asn Pro Asp Asp
    145                 150                 155

GAT TTC AGA CCA GGT CTC AAA GAT ACT AAG CTA TTG AAA ACA CTA GCT       528
Asp Phe Arg Pro Gly Leu Lys Asp Thr Lys Leu Leu Lys Thr Leu Ala
160                 165                 170                 175

ATC GGT GAC ACC ATC ACA TCT CAA GAA TTA CTA GCT CAA GCA CAA AGC       576
Ile Gly Asp Thr Ile Thr Ser Gln Glu Leu Leu Ala Gln Ala Gln Ser
                180                 185                 190

ATT TTA AAC AAA ACC CAT CCA GGC TAT ACG ATT TAT GAA CGT GAC TCC       624
Ile Leu Asn Lys Thr His Pro Gly Tyr Thr Ile Tyr Glu Arg Asp Ser
            195                 200                 205

TCA ATC GTC ACT CAT GAC AAT GAC ATT TTC CGT ACG ATT TTA CCA ATG       672
Ser Ile Val Thr His Asp Asn Asp Ile Phe Arg Thr Ile Leu Pro Met
        210                 215                 220

GAT CAA GAG TTT ACT TAC CAT GTC AAA AAT CGG GAA CAA GCT TAT GAG       720
Asp Gln Glu Phe Thr Tyr His Val Lys Asn Arg Glu Gln Ala Tyr Glu
    225                 230                 235

ATC AAT AAA AAA TCT GGT CTG AAT GAA GAA ATA AAC AAC ACT GAC CTG       768
Ile Asn Lys Lys Ser Gly Leu Asn Glu Glu Ile Asn Asn Thr Asp Leu
240                 245                 250                 255

ATC TCT GAG AAA TAT TAC GTC CTT AAA AAA GGG GAA AAG CCG TAT GAT       816
Ile Ser Glu Lys Tyr Tyr Val Leu Lys Lys Gly Glu Lys Pro Tyr Asp
                260                 265                 270

CCC TTT GAT CGC AGT CAC TTG AAA CTG TTC ACC ATC AAA TAC GTT GAT       864
Pro Phe Asp Arg Ser His Leu Lys Leu Phe Thr Ile Lys Tyr Val Asp
            275                 280                 285

GTC AAC ACC AAC GAA TTG CTA AAA AGC GAG CAG CTC TTA ACA GCT AGC       912
Val Asn Thr Asn Glu Leu Leu Lys Ser Glu Gln Leu Leu Thr Ala Ser
        290                 295                 300
```

| | | | | | | | | | | | | | | | | |
|---|---|---|---|---|---|---|---|---|---|---|---|---|---|---|---|---|
| GAA | CGT | AAC | TTA | GAC | TTC | AGA | GAT | TTA | TAC | GAT | CCT | CGT | GAT | AAG | GCT | 960 |
| Glu | Arg | Asn | Leu | Asp | Phe | Arg | Asp | Leu | Tyr | Asp | Pro | Arg | Asp | Lys | Ala | |
| | 305 | | | | 310 | | | | | 315 | | | | | | |
| AAA | CTA | CTC | TAC | AAC | AAT | CTC | GAT | GCT | TTT | GGT | ATT | ATG | GAC | TAT | ACC | 1008 |
| Lys | Leu | Leu | Tyr | Asn | Asn | Leu | Asp | Ala | Phe | Gly | Ile | Met | Asp | Tyr | Thr | |
| 320 | | | | | 325 | | | | | 330 | | | | | 335 | |
| TTA | ACT | GGA | AAA | GTA | GAA | GAT | AAT | CAC | GAT | GAC | ACC | AAC | CGT | ATC | ATA | 1056 |
| Leu | Thr | Gly | Lys | Val | Glu | Asp | Asn | His | Asp | Asp | Thr | Asn | Arg | Ile | Ile | |
| | | | | 340 | | | | 345 | | | | | | 350 | | |
| ACC | GTT | TAT | ATG | GGC | AAG | CGA | CCC | GAA | GGA | GAG | AAT | GCT | AGC | TAT | CAT | 1104 |
| Thr | Val | Tyr | Met | Gly | Lys | Arg | Pro | Glu | Gly | Glu | Asn | Ala | Ser | Tyr | His | |
| | | | 355 | | | | | 360 | | | | | 365 | | | |
| TTA | GCC | GTA | GAG | CTG | CAG | GGA | GTA | GTT | CCT | CGT | GGA | AGC | CAA | TTA | GTT | 1152 |
| Leu | Ala | Val | Glu | Leu | Gln | Gly | Val | Val | Pro | Arg | Gly | Ser | Gln | Leu | Val | |
| | | 370 | | | | | 375 | | | | | | 380 | | | |
| GTT | AGC | GTT | GCT | GGT | ACT | GTT | GAG | GGG | ACG | AAT | CAA | GAC | ATT | AGT | CTT | 1200 |
| Val | Ser | Val | Ala | Gly | Thr | Val | Glu | Gly | Thr | Asn | Gln | Asp | Ile | Ser | Leu | |
| | 385 | | | | | 390 | | | | | 395 | | | | | |
| AAA | TTT | TTT | GAA | ATT | GAC | CTA | ACA | TCA | CGA | CCT | GCT | CAT | GGA | GGA | AAG | 1248 |
| Lys | Phe | Phe | Glu | Ile | Asp | Leu | Thr | Ser | Arg | Pro | Ala | His | Gly | Gly | Lys | |
| 400 | | | | | 405 | | | | | 410 | | | | | 415 | |
| ACA | GAG | CAA | GGC | TTA | AGT | CCA | AAA | TCA | AAA | CCA | TTT | GCT | ACT | GAT | AGT | 1296 |
| Thr | Glu | Gln | Gly | Leu | Ser | Pro | Lys | Ser | Lys | Pro | Phe | Ala | Thr | Asp | Ser | |
| | | | | 420 | | | | | 425 | | | | | 430 | | |
| GGC | GCG | ATG | CCA | CAT | AAA | CTT | GAA | AAA | GCT | GAC | TTA | CTA | AAG | GCT | ATT | 1344 |
| Gly | Ala | Met | Pro | His | Lys | Leu | Glu | Lys | Ala | Asp | Leu | Leu | Lys | Ala | Ile | |
| | | | 435 | | | | | 440 | | | | | 445 | | | |
| CAA | GAA | CAA | TTG | ATC | GCT | AAC | GTC | CAC | AGT | AAC | GAC | GAC | TAC | TTT | GAG | 1392 |
| Gln | Glu | Gln | Leu | Ile | Ala | Asn | Val | His | Ser | Asn | Asp | Asp | Tyr | Phe | Glu | |
| | | 450 | | | | | 455 | | | | | 460 | | | | |
| GTC | ATT | GAT | TTT | GCA | AGC | GAT | GCA | ACC | ATT | ACT | GAT | CGA | AAC | GGC | AAG | 1440 |
| Val | Ile | Asp | Phe | Ala | Ser | Asp | Ala | Thr | Ile | Thr | Asp | Arg | Asn | Gly | Lys | |
| | 465 | | | | | 470 | | | | | 475 | | | | | |
| GTC | TAC | TTT | GCT | GAC | AAA | GAT | GGT | TCG | GTA | ACC | TTG | CCG | ACC | CAA | CCT | 1488 |
| Val | Tyr | Phe | Ala | Asp | Lys | Asp | Gly | Ser | Val | Thr | Leu | Pro | Thr | Gln | Pro | |
| 480 | | | | | 485 | | | | | 490 | | | | | 495 | |
| GTC | CAA | GAA | TTT | TTG | CTA | AGC | GGA | CAT | GTG | CGC | GTT | AGA | CCA | TAT | AAA | 1536 |
| Val | Gln | Glu | Phe | Leu | Leu | Ser | Gly | His | Val | Arg | Val | Arg | Pro | Tyr | Lys | |
| | | | | 500 | | | | | 505 | | | | | 510 | | |
| GAA | AAA | CCA | ATA | CAA | AAT | CAA | GCG | AAA | TCT | GTT | GAT | GTG | GAA | TAT | ACT | 1584 |
| Glu | Lys | Pro | Ile | Gln | Asn | Gln | Ala | Lys | Ser | Val | Asp | Val | Glu | Tyr | Thr | |
| | | | 515 | | | | | 520 | | | | | 525 | | | |
| GTA | CAG | TTT | ACT | CCC | TTA | AAC | CCT | GAT | GAC | GAT | TTC | AGA | CCA | GGT | CTC | 1632 |
| Val | Gln | Phe | Thr | Pro | Leu | Asn | Pro | Asp | Asp | Asp | Phe | Arg | Pro | Gly | Leu | |
| | | 530 | | | | | 535 | | | | | 540 | | | | |
| AAA | GAT | ACT | AAG | CTA | TTG | AAA | ACA | CTA | GCT | ATC | GGT | GAC | ACC | ATC | ACA | 1680 |
| Lys | Asp | Thr | Lys | Leu | Leu | Lys | Thr | Leu | Ala | Ile | Gly | Asp | Thr | Ile | Thr | |
| | 545 | | | | | 550 | | | | | 555 | | | | | |
| TCT | CAA | GAA | TTA | CTA | GCT | CAA | GCA | CAA | AGC | ATT | TTA | AAC | AAA | ACC | CAT | 1728 |
| Ser | Gln | Glu | Leu | Leu | Ala | Gln | Ala | Gln | Ser | Ile | Leu | Asn | Lys | Thr | His | |
| 560 | | | | | 565 | | | | | 570 | | | | | 575 | |
| CCA | GGC | TAT | ACG | ATT | TAT | GAA | CGT | GAC | TCC | TCA | ATC | GTC | ACT | CAT | GAC | 1776 |
| Pro | Gly | Tyr | Thr | Ile | Tyr | Glu | Arg | Asp | Ser | Ser | Ile | Val | Thr | His | Asp | |
| | | | | 580 | | | | | 585 | | | | | 590 | | |
| AAT | GAC | ATT | TTC | CGT | ACG | ATT | TTA | CCA | ATG | GAT | CAA | GAG | TTT | ACT | TAC | 1824 |
| Asn | Asp | Ile | Phe | Arg | Thr | Ile | Leu | Pro | Met | Asp | Gln | Glu | Phe | Thr | Tyr | |
| | | | 595 | | | | | 600 | | | | | 605 | | | |
| CAT | GTC | AAA | AAT | CGG | GAA | CAA | GCT | TAT | GAG | ATC | AAT | AAA | AAA | TCT | GGT | 1872 |
| His | Val | Lys | Asn | Arg | Glu | Gln | Ala | Tyr | Glu | Ile | Asn | Lys | Lys | Ser | Gly | |
| | | 610 | | | | | 615 | | | | | 620 | | | | |
| CTG | AAT | GAA | GAA | ATA | AAC | AAC | ACT | GAC | CTG | ATC | TCT | GAG | AAA | TAT | TAC | 1920 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | Leu | Asn | Glu | Glu | Ile | Asn | Asn | Thr | Asp | Leu | Ile | Ser | Glu | Lys | Tyr | Tyr |
|     | 625 |     |     |     |     | 630 |     |     |     |     |     | 635 |     |     |     |     |
| GTC | CTT | AAA | AAA | GGG | GAA | AAG | CCG | TAT | GAT | CCC | TTT | GAT | CGC | AGT | CAC | 1968 |
| Val | Leu | Lys | Lys | Gly | Glu | Lys | Pro | Tyr | Asp | Pro | Phe | Asp | Arg | Ser | His |      |
| 640 |     |     |     |     | 645 |     |     |     |     | 650 |     |     |     |     | 655 |      |
| TTG | AAA | CTG | TTC | ACC | ATC | AAA | TAC | GTT | GAT | GTC | AAC | ACC | AAC | GAA | TTG | 2016 |
| Leu | Lys | Leu | Phe | Thr | Ile | Lys | Tyr | Val | Asp | Val | Asn | Thr | Asn | Glu | Leu |      |
|     |     |     |     | 660 |     |     |     |     | 665 |     |     |     |     | 670 |     |      |
| CTA | AAA | AGC | GAG | CAG | CTC | TTA | ACA | GCT | AGC | GAA | CGT | AAC | TTA | GAC | TTC | 2064 |
| Leu | Lys | Ser | Glu | Gln | Leu | Leu | Thr | Ala | Ser | Glu | Arg | Asn | Leu | Asp | Phe |      |
|     |     |     | 675 |     |     |     |     | 680 |     |     |     |     | 685 |     |     |      |
| AGA | GAT | TTA | TAC | GAT | CCT | CGT | GAT | AAG | GCT | AAA | CTA | CTC | TAC | AAC | AAT | 2112 |
| Arg | Asp | Leu | Tyr | Asp | Pro | Arg | Asp | Lys | Ala | Lys | Leu | Leu | Tyr | Asn | Asn |      |
|     |     | 690 |     |     |     |     | 695 |     |     |     |     | 700 |     |     |     |      |
| CTC | GAT | GCT | TTT | GGT | ATT | ATG | GAC | TAT | ACC | TTA | ACT | GGA | AAA | GTA | GAA | 2160 |
| Leu | Asp | Ala | Phe | Gly | Ile | Met | Asp | Tyr | Thr | Leu | Thr | Gly | Lys | Val | Glu |      |
|     | 705 |     |     |     |     | 710 |     |     |     |     | 715 |     |     |     |     |      |
| GAT | AAT | CAC | GAT | GAC | ACC | AAC | CGT | ATC | ATA | ACC | GTT | TAT | ATG | GGC | AAG | 2208 |
| Asp | Asn | His | Asp | Asp | Thr | Asn | Arg | Ile | Ile | Thr | Val | Tyr | Met | Gly | Lys |      |
| 720 |     |     |     |     | 725 |     |     |     |     | 730 |     |     |     |     | 735 |      |
| CGA | CCC | GAA | GGA | GAG | AAT | GCT | AGC | TAT | CAT | TTA | GCC | TAAGGATCC |  |  |  | 2253 |
| Arg | Pro | Glu | Gly | Glu | Asn | Ala | Ser | Tyr | His | Leu | Ala |           |  |  |  |      |
|     |     |     |     | 740 |     |     |     |     | 745 |     |     |           |  |  |  |      |

( 2 ) INFORMATION FOR SEQ ID NO:40:

( i ) SEQUENCE CHARACTERISTICS:
        ( A ) LENGTH: 747 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

|     |     |     |     |     |     |     |     |     |     |     |     |     |     |     |
| --- | --- | --- | --- | --- | --- | --- | --- | --- | --- | --- | --- | --- | --- | --- |
| Met | Ser | Gln | Leu | Val | Val | Ser | Val | Ala | Gly | Thr | Val | Glu | Gly | Thr | Asn |
| 1   |     |     |     | 5   |     |     |     |     | 10  |     |     |     |     | 15  |     |
| Gln | Asp | Ile | Ser | Leu | Lys | Phe | Phe | Glu | Ile | Asp | Leu | Thr | Ser | Arg | Pro |
|     |     |     | 20  |     |     |     |     | 25  |     |     |     |     | 30  |     |     |
| Ala | His | Gly | Gly | Lys | Thr | Glu | Gln | Gly | Leu | Ser | Pro | Lys | Ser | Lys | Pro |
|     |     | 35  |     |     |     |     | 40  |     |     |     |     | 45  |     |     |     |
| Phe | Ala | Thr | Asp | Ser | Gly | Ala | Met | Pro | His | Lys | Leu | Glu | Lys | Ala | Asp |
|     | 50  |     |     |     |     | 55  |     |     |     |     | 60  |     |     |     |     |
| Leu | Leu | Lys | Ala | Ile | Gln | Glu | Gln | Leu | Ile | Ala | Asn | Val | His | Ser | Asn |
| 65  |     |     |     |     | 70  |     |     |     |     | 75  |     |     |     |     | 80  |
| Asp | Asp | Tyr | Phe | Glu | Val | Ile | Asp | Phe | Ala | Ser | Asp | Ala | Thr | Ile | Thr |
|     |     |     |     | 85  |     |     |     |     | 90  |     |     |     |     | 95  |     |
| Asp | Arg | Asn | Gly | Lys | Val | Tyr | Phe | Ala | Asp | Lys | Asp | Gly | Ser | Val | Thr |
|     |     |     | 100 |     |     |     |     | 105 |     |     |     |     | 110 |     |     |
| Leu | Pro | Thr | Gln | Pro | Val | Gln | Glu | Phe | Leu | Leu | Ser | Gly | His | Val | Arg |
|     |     | 115 |     |     |     |     | 120 |     |     |     |     | 125 |     |     |     |
| Val | Arg | Pro | Tyr | Lys | Glu | Lys | Pro | Ile | Gln | Asn | Gln | Ala | Lys | Ser | Val |
|     | 130 |     |     |     |     | 135 |     |     |     |     | 140 |     |     |     |     |
| Asp | Val | Glu | Tyr | Thr | Val | Gln | Phe | Thr | Pro | Leu | Asn | Pro | Asp | Asp | Asp |
| 145 |     |     |     |     | 150 |     |     |     |     | 155 |     |     |     |     | 160 |
| Phe | Arg | Pro | Gly | Leu | Lys | Asp | Thr | Lys | Leu | Leu | Lys | Thr | Leu | Ala | Ile |
|     |     |     |     | 165 |     |     |     |     | 170 |     |     |     |     | 175 |     |
| Gly | Asp | Thr | Ile | Thr | Ser | Gln | Glu | Leu | Leu | Ala | Gln | Ala | Gln | Ser | Ile |
|     |     |     | 180 |     |     |     |     | 185 |     |     |     |     | 190 |     |     |
| Leu | Asn | Lys | Thr | His | Pro | Gly | Tyr | Thr | Ile | Tyr | Glu | Arg | Asp | Ser | Ser |
|     |     | 195 |     |     |     |     | 200 |     |     |     |     | 205 |     |     |     |

```
Ile Val Thr His Asp Asn Asp Ile Phe Arg Thr Ile Leu Pro Met Asp
    210                 215                 220
Gln Glu Phe Thr Tyr His Val Lys Asn Arg Glu Gln Ala Tyr Glu Ile
225                 230                 235                 240
Asn Lys Lys Ser Gly Leu Asn Glu Glu Ile Asn Asn Thr Asp Leu Ile
                245                 250                 255
Ser Glu Lys Tyr Tyr Val Leu Lys Lys Gly Glu Lys Pro Tyr Asp Pro
                260                 265                 270
Phe Asp Arg Ser His Leu Lys Leu Phe Thr Ile Lys Tyr Val Asp Val
            275                 280                 285
Asn Thr Asn Glu Leu Leu Lys Ser Glu Gln Leu Leu Thr Ala Ser Glu
    290                 295                 300
Arg Asn Leu Asp Phe Arg Asp Leu Tyr Asp Pro Arg Asp Lys Ala Lys
305                 310                 315                 320
Leu Leu Tyr Asn Asn Leu Asp Ala Phe Gly Ile Met Asp Tyr Thr Leu
                325                 330                 335
Thr Gly Lys Val Glu Asp Asn His Asp Asp Thr Asn Arg Ile Ile Thr
                340                 345                 350
Val Tyr Met Gly Lys Arg Pro Glu Gly Glu Asn Ala Ser Tyr His Leu
            355                 360                 365
Ala Val Glu Leu Gln Gly Val Val Pro Arg Gly Ser Gln Leu Val Val
    370                 375                 380
Ser Val Ala Gly Thr Val Glu Gly Thr Asn Gln Asp Ile Ser Leu Lys
385                 390                 395                 400
Phe Phe Glu Ile Asp Leu Thr Ser Arg Pro Ala His Gly Gly Lys Thr
                405                 410                 415
Glu Gln Gly Leu Ser Pro Lys Ser Lys Pro Phe Ala Thr Asp Ser Gly
            420                 425                 430
Ala Met Pro His Lys Leu Glu Lys Ala Asp Leu Leu Lys Ala Ile Gln
    435                 440                 445
Glu Gln Leu Ile Ala Asn Val His Ser Asn Asp Asp Tyr Phe Glu Val
    450                 455                 460
Ile Asp Phe Ala Ser Asp Ala Thr Ile Thr Asp Arg Asn Gly Lys Val
465                 470                 475                 480
Tyr Phe Ala Asp Lys Asp Gly Ser Val Thr Leu Pro Thr Gln Pro Val
            485                 490                 495
Gln Glu Phe Leu Leu Ser Gly His Val Arg Val Arg Pro Tyr Lys Glu
            500                 505                 510
Lys Pro Ile Gln Asn Gln Ala Lys Ser Val Asp Val Glu Tyr Thr Val
        515                 520                 525
Gln Phe Thr Pro Leu Asn Pro Asp Asp Phe Arg Pro Gly Leu Lys
530                 535                 540
Asp Thr Lys Leu Leu Lys Thr Leu Ala Ile Gly Asp Thr Ile Thr Ser
545                 550                 555                 560
Gln Glu Leu Leu Ala Gln Ala Gln Ser Ile Leu Asn Lys Thr His Pro
                565                 570                 575
Gly Tyr Thr Ile Tyr Glu Arg Asp Ser Ser Ile Val Thr His Asp Asn
            580                 585                 590
Asp Ile Phe Arg Thr Ile Leu Pro Met Asp Gln Glu Phe Thr Tyr His
            595                 600                 605
Val Lys Asn Arg Glu Gln Ala Tyr Glu Ile Asn Lys Lys Ser Gly Leu
    610                 615                 620
Asn Glu Glu Ile Asn Asn Thr Asp Leu Ile Ser Glu Lys Tyr Tyr Val
625                 630                 635                 640
Leu Lys Lys Gly Glu Lys Pro Tyr Asp Pro Phe Asp Arg Ser His Leu
```

|     |     |     |     | 645 |     |     |     |     | 650 |     |     |     |     | 655 |
| --- | --- | --- | --- | --- | --- | --- | --- | --- | --- | --- | --- | --- | --- | --- |

Lys Leu Phe Thr Ile Lys Tyr Val Asp Val Asn Thr Asn Glu Leu Leu
            660             665             670

Lys Ser Glu Gln Leu Leu Thr Ala Ser Glu Arg Asn Leu Asp Phe Arg
        675             680             685

Asp Leu Tyr Asp Pro Arg Asp Lys Ala Lys Leu Leu Tyr Asn Asn Leu
        690             695             700

Asp Ala Phe Gly Ile Met Asp Tyr Thr Leu Thr Gly Lys Val Glu Asp
705             710             715             720

Asn His Asp Asp Thr Asn Arg Ile Ile Thr Val Tyr Met Gly Lys Arg
            725             730             735

Pro Glu Gly Glu Asn Ala Ser Tyr His Leu Ala
            740             745

( 2 ) INFORMATION FOR SEQ ID NO:41:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..61
        ( D ) OTHER INFORMATION: /note="oligonucleotide BB3861"

( x i ) SEQUENCE DESCRIPTION: SEQ ID NO:41:

GCTATCATTT AGCCGTAGAG CTGCAGGGAG TAGTTCCTCG TGGAAGCCAA TTAGTTGTTA    60

G    61

( 2 ) INFORMATION FOR SEQ ID NO:42:

( i ) SEQUENCE CHARACTERISTICS:
        ( A ) LENGTH: 1458 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..1458
        ( D ) OTHER INFORMATION: /note="Hirudin-streptokinase
                fusion linked by Factor Xa cleavable IEGR"

( i x ) FEATURE:
        ( A ) NAME/KEY: CDS
        ( B ) LOCATION: 1..1449

( i x ) FEATURE:
        ( A ) NAME/KEY: mat_peptide
        ( B ) LOCATION: 1..1449

( x i ) SEQUENCE DESCRIPTION: SEQ ID NO:42:

GTT GTT TAC ACC GAC TGT ACT GAA TCC GGA CAA AAC CTG TGT TTG TGT    48
Val Val Tyr Thr Asp Cys Thr Glu Ser Gly Gln Asn Leu Cys Leu Cys
1                   5                   10                  15

GAG GGT TCT AAC GTC TGT GGT CAG GGT AAC AAA TGC ATC CTG GGT TCC    96
Glu Gly Ser Asn Val Cys Gly Gln Gly Asn Lys Cys Ile Leu Gly Ser
            20                  25                  30

GAC GGT GAA AAG AAC CAA TGT GTC ACT GGT GAA GGT ACC CCA AAG CCG    144
Asp Gly Glu Lys Asn Gln Cys Val Thr Gly Glu Gly Thr Pro Lys Pro
        35                  40                  45

CAG TCC CAC AAC GAT GGA GAT TTC GAA GAA ATC CCA GAA GAA TAT CTG    192

```
    Gln  Ser  His  Asn  Asp  Gly  Asp  Phe  Glu  Glu  Ile  Pro  Glu  Glu  Tyr  Leu
         50                       55                       60

CAG  ATC  GAA  GGT  AGA  ATT  GCT  GGA  CCT  GAG  TGG  CTG  CTA  GAC  CGT  CCA         240
Gln  Ile  Glu  Gly  Arg  Ile  Ala  Gly  Pro  Glu  Trp  Leu  Leu  Asp  Arg  Pro
65                       70                       75                       80

TCT  GTC  AAC  AAC  AGC  CAA  TTA  GTT  GTT  AGC  GTT  GCT  GGT  ACT  GTT  GAG         288
Ser  Val  Asn  Asn  Ser  Gln  Leu  Val  Val  Ser  Val  Ala  Gly  Thr  Val  Glu
                    85                       90                       95

GGG  ACG  AAT  CAA  GAC  ATT  AGT  CTT  AAA  TTT  TTT  GAA  ATT  GAC  CTA  ACA         336
Gly  Thr  Asn  Gln  Asp  Ile  Ser  Leu  Lys  Phe  Phe  Glu  Ile  Asp  Leu  Thr
               100                      105                      110

TCA  CGA  CCT  GCT  CAT  GGA  GGA  AAG  ACA  GAG  CAA  GGC  TTA  AGT  CCA  AAA         384
Ser  Arg  Pro  Ala  His  Gly  Gly  Lys  Thr  Glu  Gln  Gly  Leu  Ser  Pro  Lys
          115                      120                      125

TCA  AAA  CCA  TTT  GCT  ACT  GAT  AGT  GGC  GCG  ATG  CCA  CAT  AAA  CTT  GAA         432
Ser  Lys  Pro  Phe  Ala  Thr  Asp  Ser  Gly  Ala  Met  Pro  His  Lys  Leu  Glu
     130                      135                      140

AAA  GCT  GAC  TTA  CTA  AAG  GCT  ATT  CAA  GAA  CAA  TTG  ATC  GCT  AAC  GTC         480
Lys  Ala  Asp  Leu  Leu  Lys  Ala  Ile  Gln  Glu  Gln  Leu  Ile  Ala  Asn  Val
145                      150                      155                      160

CAC  AGT  AAC  GAC  GAC  TAC  TTT  GAG  GTC  ATT  GAT  TTT  GCA  AGC  GAT  GCA         528
His  Ser  Asn  Asp  Asp  Tyr  Phe  Glu  Val  Ile  Asp  Phe  Ala  Ser  Asp  Ala
                    165                      170                      175

ACC  ATT  ACT  GAT  CGA  AAC  GGC  AAG  GTC  TAC  TTT  GCT  GAC  AAA  GAT  GGT         576
Thr  Ile  Thr  Asp  Arg  Asn  Gly  Lys  Val  Tyr  Phe  Ala  Asp  Lys  Asp  Gly
               180                      185                      190

TCG  GTA  ACC  TTG  CCG  ACC  CAA  CCT  GTC  CAA  GAA  TTT  TTG  CTA  AGC  GGA         624
Ser  Val  Thr  Leu  Pro  Thr  Gln  Pro  Val  Gln  Glu  Phe  Leu  Leu  Ser  Gly
          195                      200                      205

CAT  GTG  CGC  GTT  AGA  CCA  TAT  AAA  GAA  AAA  CCA  ATA  CAA  AAT  CAA  GCG         672
His  Val  Arg  Val  Arg  Pro  Tyr  Lys  Glu  Lys  Pro  Ile  Gln  Asn  Gln  Ala
     210                      215                      220

AAA  TCT  GTT  GAT  GTG  GAA  TAT  ACT  GTA  CAG  TTT  ACT  CCC  TTA  AAC  CCT         720
Lys  Ser  Val  Asp  Val  Glu  Tyr  Thr  Val  Gln  Phe  Thr  Pro  Leu  Asn  Pro
225                      230                      235                      240

GAT  GAC  GAT  TTC  AGA  CCA  GGT  CTC  AAA  GAT  ACT  AAG  CTA  TTG  AAA  ACA         768
Asp  Asp  Asp  Phe  Arg  Pro  Gly  Leu  Lys  Asp  Thr  Lys  Leu  Leu  Lys  Thr
                    245                      250                      255

CTA  GCT  ATC  GGT  GAC  ACC  ATC  ACA  TCT  CAA  GAA  TTA  CTA  GCT  CAA  GCA         816
Leu  Ala  Ile  Gly  Asp  Thr  Ile  Thr  Ser  Gln  Glu  Leu  Leu  Ala  Gln  Ala
               260                      265                      270

CAA  AGC  ATT  TTA  AAC  AAA  ACC  CAT  CCA  GGC  TAT  ACG  ATT  TAT  GAA  CGT         864
Gln  Ser  Ile  Leu  Asn  Lys  Thr  His  Pro  Gly  Tyr  Thr  Ile  Tyr  Glu  Arg
          275                      280                      285

GAC  TCC  TCA  ATC  GTC  ACT  CAT  GAC  AAT  GAC  ATT  TTC  CGT  ACG  ATT  TTA         912
Asp  Ser  Ser  Ile  Val  Thr  His  Asp  Asn  Asp  Ile  Phe  Arg  Thr  Ile  Leu
     290                      295                      300

CCA  ATG  GAT  CAA  GAG  TTT  ACT  TAC  CAT  GTC  AAA  AAT  CGG  GAA  CAA  GCT         960
Pro  Met  Asp  Gln  Glu  Phe  Thr  Tyr  His  Val  Lys  Asn  Arg  Glu  Gln  Ala
305                      310                      315                      320

TAT  GAG  ATC  AAT  AAA  AAA  TCT  GGT  CTG  AAT  GAA  GAA  ATA  AAC  AAC  ACT        1008
Tyr  Glu  Ile  Asn  Lys  Lys  Ser  Gly  Leu  Asn  Glu  Glu  Ile  Asn  Asn  Thr
                    325                      330                      335

GAC  CTG  ATC  TCT  GAG  AAA  TAT  TAC  GTC  CTT  AAA  AAA  GGG  GAA  AAG  CCG        1056
Asp  Leu  Ile  Ser  Glu  Lys  Tyr  Tyr  Val  Leu  Lys  Lys  Gly  Glu  Lys  Pro
               340                      345                      350

TAT  GAT  CCC  TTT  GAT  CGC  AGT  CAC  TTG  AAA  CTG  TTC  ACC  ATC  AAA  TAC        1104
Tyr  Asp  Pro  Phe  Asp  Arg  Ser  His  Leu  Lys  Leu  Phe  Thr  Ile  Lys  Tyr
          355                      360                      365

GTT  GAT  GTC  AAC  ACC  AAC  GAA  TTG  CTA  AAA  AGC  GAG  CAG  CTC  TTA  ACA        1152
Val  Asp  Val  Asn  Thr  Asn  Glu  Leu  Leu  Lys  Ser  Glu  Gln  Leu  Leu  Thr
     370                      375                      380
```

```
GCT AGC GAA CGT AAC TTA GAC TTC AGA GAT TTA TAC GAT CCT CGT GAT    1200
Ala Ser Glu Arg Asn Leu Asp Phe Arg Asp Leu Tyr Asp Pro Arg Asp
385             390                 395                 400

AAG GCT AAA CTA CTC TAC AAC AAT CTC GAT GCT TTT GGT ATT ATG GAC    1248
Lys Ala Lys Leu Leu Tyr Asn Asn Leu Asp Ala Phe Gly Ile Met Asp
            405                 410                 415

TAT ACC TTA ACT GGA AAA GTA GAA GAT AAT CAC GAT GAC ACC AAC CGT    1296
Tyr Thr Leu Thr Gly Lys Val Glu Asp Asn His Asp Asp Thr Asn Arg
                420                 425                 430

ATC ATA ACC GTT TAT ATG GGC AAG CGA CCC GAA GGA GAG AAT GCT AGC    1344
Ile Ile Thr Val Tyr Met Gly Lys Arg Pro Glu Gly Glu Asn Ala Ser
        435                 440                 445

TAT CAT TTA GCC TAT GAT AAA GAT CGT TAT ACC GAA GAA GAA CGA GAA    1392
Tyr His Leu Ala Tyr Asp Lys Asp Arg Tyr Thr Glu Glu Glu Arg Glu
    450                 455                 460

GTT TAC AGC TAC CTG CGT TAT ACA GGG ACA CCT ATA CCT GAT AAC CCT    1440
Val Tyr Ser Tyr Leu Arg Tyr Thr Gly Thr Pro Ile Pro Asp Asn Pro
465                 470                 475                 480

AAC GAC AAA TAAGGATCC                                              1458
Asn Asp Lys
```

( 2 ) INFORMATION FOR SEQ ID NO:43:

( i ) SEQUENCE CHARACTERISTICS:
    ( A ) LENGTH: 483 amino acids
    ( B ) TYPE: amino acid
    ( D ) TOPOLOGY: linear ( i i ) MOLECULE TYPE: protein ( x i ) SEQUENCE DESCRIPTION: SEQ ID NO:43:

```
Val Val Tyr Thr Asp Cys Thr Glu Ser Gly Gln Asn Leu Cys Leu Cys
  1             5                  10                  15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
         35                  40                  45

Gln Ser His Asn Asp Gly Asp Phe Glu Glu Ile Pro Glu Glu Tyr Leu
     50                  55                  60

Gln Ile Glu Gly Arg Ile Ala Gly Pro Glu Trp Leu Leu Asp Arg Pro
 65                  70                  75                  80

Ser Val Asn Asn Ser Gln Leu Val Val Ser Val Ala Gly Thr Val Glu
                85                  90                  95

Gly Thr Asn Gln Asp Ile Ser Leu Lys Phe Phe Glu Ile Asp Leu Thr
            100                 105                 110

Ser Arg Pro Ala His Gly Gly Lys Thr Glu Gln Gly Leu Ser Pro Lys
        115                 120                 125

Ser Lys Pro Phe Ala Thr Asp Ser Gly Ala Met Pro His Lys Leu Glu
    130                 135                 140

Lys Ala Asp Leu Leu Lys Ala Ile Gln Glu Gln Leu Ile Ala Asn Val
145                 150                 155                 160

His Ser Asn Asp Asp Tyr Phe Glu Val Ile Asp Phe Ala Ser Asp Ala
                165                 170                 175

Thr Ile Thr Asp Arg Asn Gly Lys Val Tyr Phe Ala Asp Lys Asp Gly
            180                 185                 190

Ser Val Thr Leu Pro Thr Gln Pro Val Gln Glu Phe Leu Leu Ser Gly
        195                 200                 205

His Val Arg Val Arg Pro Tyr Lys Glu Lys Pro Ile Gln Asn Gln Ala
    210                 215                 220
```

| Lys | Ser | Val | Asp | Val | Glu | Tyr | Thr | Val | Gln | Phe | Thr | Pro | Leu | Asn | Pro |
|---|---|---|---|---|---|---|---|---|---|---|---|---|---|---|---|
| 225 | | | | 230 | | | | | 235 | | | | | | 240 |

| Asp | Asp | Asp | Phe | Arg | Pro | Gly | Leu | Lys | Asp | Thr | Lys | Leu | Leu | Lys | Thr |
|---|---|---|---|---|---|---|---|---|---|---|---|---|---|---|---|
| | | | | 245 | | | | 250 | | | | | 255 | | |

| Leu | Ala | Ile | Gly | Asp | Thr | Ile | Thr | Ser | Gln | Glu | Leu | Leu | Ala | Gln | Ala |
|---|---|---|---|---|---|---|---|---|---|---|---|---|---|---|---|
| | | | 260 | | | | 265 | | | | | | 270 | | |

| Gln | Ser | Ile | Leu | Asn | Lys | Thr | His | Pro | Gly | Tyr | Thr | Ile | Tyr | Glu | Arg |
|---|---|---|---|---|---|---|---|---|---|---|---|---|---|---|---|
| | | 275 | | | | | 280 | | | | | 285 | | | |

| Asp | Ser | Ser | Ile | Val | Thr | His | Asp | Asn | Asp | Ile | Phe | Arg | Thr | Ile | Leu |
|---|---|---|---|---|---|---|---|---|---|---|---|---|---|---|---|
| | 290 | | | | | 295 | | | | | 300 | | | | |

| Pro | Met | Asp | Gln | Glu | Phe | Thr | Tyr | His | Val | Lys | Asn | Arg | Glu | Gln | Ala |
|---|---|---|---|---|---|---|---|---|---|---|---|---|---|---|---|
| 305 | | | | | 310 | | | | | 315 | | | | | 320 |

| Tyr | Glu | Ile | Asn | Lys | Ser | Gly | Leu | Asn | Glu | Glu | Ile | Asn | Asn | Thr |
|---|---|---|---|---|---|---|---|---|---|---|---|---|---|---|
| | | | | 325 | | | | 330 | | | | | 335 | |

| Asp | Leu | Ile | Ser | Glu | Lys | Tyr | Tyr | Val | Leu | Lys | Lys | Gly | Glu | Lys | Pro |
|---|---|---|---|---|---|---|---|---|---|---|---|---|---|---|---|
| | | | 340 | | | | | 345 | | | | 350 | | | |

| Tyr | Asp | Pro | Phe | Asp | Arg | Ser | His | Leu | Lys | Leu | Phe | Thr | Ile | Lys | Tyr |
|---|---|---|---|---|---|---|---|---|---|---|---|---|---|---|---|
| | | 355 | | | | | 360 | | | | | 365 | | | |

| Val | Asp | Val | Asn | Thr | Asn | Glu | Leu | Leu | Lys | Ser | Glu | Gln | Leu | Leu | Thr |
|---|---|---|---|---|---|---|---|---|---|---|---|---|---|---|---|
| | 370 | | | | 375 | | | | | 380 | | | | | |

| Ala | Ser | Glu | Arg | Asn | Leu | Asp | Phe | Arg | Asp | Leu | Tyr | Asp | Pro | Arg | Asp |
|---|---|---|---|---|---|---|---|---|---|---|---|---|---|---|---|
| 385 | | | | | 390 | | | | 395 | | | | | | 400 |

| Lys | Ala | Lys | Leu | Leu | Tyr | Asn | Asn | Leu | Asp | Ala | Phe | Gly | Ile | Met | Asp |
|---|---|---|---|---|---|---|---|---|---|---|---|---|---|---|---|
| | | | | 405 | | | | | 410 | | | | | 415 | |

| Tyr | Thr | Leu | Thr | Gly | Lys | Val | Glu | Asp | Asn | His | Asp | Asp | Thr | Asn | Arg |
|---|---|---|---|---|---|---|---|---|---|---|---|---|---|---|---|
| | | | 420 | | | | | 425 | | | | | 430 | | |

| Ile | Ile | Thr | Val | Tyr | Met | Gly | Lys | Arg | Pro | Glu | Gly | Glu | Asn | Ala | Ser |
|---|---|---|---|---|---|---|---|---|---|---|---|---|---|---|---|
| | | 435 | | | | | 440 | | | | | 445 | | | |

| Tyr | His | Leu | Ala | Tyr | Asp | Lys | Asp | Arg | Tyr | Thr | Glu | Glu | Glu | Arg | Glu |
|---|---|---|---|---|---|---|---|---|---|---|---|---|---|---|---|
| | 450 | | | | | 455 | | | | | 460 | | | | |

| Val | Tyr | Ser | Tyr | Leu | Arg | Tyr | Thr | Gly | Thr | Pro | Ile | Pro | Asp | Asn | Pro |
|---|---|---|---|---|---|---|---|---|---|---|---|---|---|---|---|
| 465 | | | | | 470 | | | | | 475 | | | | | 480 |

| Asn | Asp | Lys |
|---|---|---|

(2) INFORMATION FOR SEQ ID NO:44:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..46
        (D) OTHER INFORMATION: /note="oligonucleotide BB3317"

(xi) SEQUENCE DESCRIPTION: SEQ ID NO:44:

CACTCAGGTC CAGCAATTCT ACCTTCGATC TGCAGATATT CTTCTG      46

(2) INFORMATION FOR SEQ ID NO:45:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (ix) FEATURE:

(A) NAME/KEY: misc_feature
(B) LOCATION: 1..17
(D) OTHER INFORMATION: /note="oligonucleotiede BB3510"

(xi) SEQUENCE DESCRIPTION: SEQ ID NO:45:

CACTATCAGT AGCAAAT                                                                                  17

(2) INFORMATION FOR SEQ ID NO:46:

(i) SEQUENCE CHARACTERISTICS:
      (A) LENGTH: 1467 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: misc_feature
      (B) LOCATION: 1..1467
      (D) OTHER INFORMATION: /note="Streptokinase-hirudin
          fusion linked by Factor Xa-cleavable IEGR"

(ix) FEATURE:
      (A) NAME/KEY: CDS
      (B) LOCATION: 1..1449

(ix) FEATURE:
      (A) NAME/KEY: mat_peptide
      (B) LOCATION: 1..1449

(xi) SEQUENCE DESCRIPTION: SEQ ID NO:46:

```
ATT GCT GGA CCT GAG TGG CTG CTA GAC CGT CCA TCT GTC AAC AAC AGC      48
Ile Ala Gly Pro Glu Trp Leu Leu Asp Arg Pro Ser Val Asn Asn Ser
 1           5                  10                  15

CAA TTA GTT GTT AGC GTT GCT GGT ACT GTT GAG GGG ACG AAT CAA GAC      96
Gln Leu Val Val Ser Val Ala Gly Thr Val Glu Gly Thr Asn Gln Asp
                 20                  25                  30

ATT AGT CTT AAA TTT TTT GAA ATT GAC CTA ACA TCA CGA CCT GCT CAT     144
Ile Ser Leu Lys Phe Phe Glu Ile Asp Leu Thr Ser Arg Pro Ala His
             35                  40                  45

GGA GGA AAG ACA GAG CAA GGC TTA AGT CCA AAA TCA AAA CCA TTT GCT     192
Gly Gly Lys Thr Glu Gln Gly Leu Ser Pro Lys Ser Lys Pro Phe Ala
 50                  55                  60

ACT GAT AGT GGC GCG ATG CCA CAT AAA CTT GAA AAA GCT GAC TTA CTA     240
Thr Asp Ser Gly Ala Met Pro His Lys Leu Glu Lys Ala Asp Leu Leu
 65                  70                  75                  80

AAG GCT ATT CAA GAA CAA TTG ATC GCT AAC GTC CAC AGT AAC GAC GAC     288
Lys Ala Ile Gln Glu Gln Leu Ile Ala Asn Val His Ser Asn Asp Asp
                 85                  90                  95

TAC TTT GAG GTC ATT GAT TTT GCA AGC GAT GCA ACC ATT ACT GAT CGA     336
Tyr Phe Glu Val Ile Asp Phe Ala Ser Asp Ala Thr Ile Thr Asp Arg
                100                 105                 110

AAC GGC AAG GTC TAC TTT GCT GAC AAA GAT GGT TCG GTA ACC TTG CCG     384
Asn Gly Lys Val Tyr Phe Ala Asp Lys Asp Gly Ser Val Thr Leu Pro
            115                 120                 125

ACC CAA CCT GTC CAA GAA TTT TTG CTA AGC GGA CAT GTG CGC GTT AGA     432
Thr Gln Pro Val Gln Glu Phe Leu Leu Ser Gly His Val Arg Val Arg
130                 135                 140

CCA TAT AAA GAA AAA CCA ATA CAA AAT CAA GCG AAA TCT GTT GAT GTG     480
Pro Tyr Lys Glu Lys Pro Ile Gln Asn Gln Ala Lys Ser Val Asp Val
145                 150                 155                 160

GAA TAT ACT GTA CAG TTT ACT CCC TTA AAC CCT GAT GAC GAT TTC AGA     528
Glu Tyr Thr Val Gln Phe Thr Pro Leu Asn Pro Asp Asp Asp Phe Arg
                165                 170                 175

CCA GGT CTC AAA GAT ACT AAG CTA TTG AAA ACA CTA GCT ATC GGT GAC     576
Pro Gly Leu Lys Asp Thr Lys Leu Leu Lys Thr Leu Ala Ile Gly Asp
            180                 185                 190
```

| | | | | | | | | | | | | | | | | |
|---|---|---|---|---|---|---|---|---|---|---|---|---|---|---|---|---|
| ACC | ATC | ACA | TCT | CAA | GAA | TTA | CTA | GCT | CAA | GCA | CAA | AGC | ATT | TTA | AAC | 624 |
| Thr | Ile | Thr 195 | Ser | Gln | Glu | Leu | Leu 200 | Ala | Gln | Ala | Gln | Ser 205 | Ile | Leu | Asn | |
| AAA | ACC | CAT | CCA | GGC | TAT | ACG | ATT | TAT | GAA | CGT | GAC | TCC | TCA | ATC | GTC | 672 |
| Lys | Thr 210 | His | Pro | Gly | Tyr | Thr 215 | Ile | Tyr | Glu | Arg | Asp 220 | Ser | Ser | Ile | Val | |
| ACT | CAT | GAC | AAT | GAC | ATT | TTC | CGT | ACG | ATT | TTA | CCA | ATG | GAT | CAA | GAG | 720 |
| Thr 225 | His | Asp | Asn | Asp | Ile 230 | Phe | Arg | Thr | Ile | Leu 235 | Pro | Met | Asp | Gln | Glu 240 | |
| TTT | ACT | TAC | CAT | GTC | AAA | AAT | CGG | GAA | CAA | GCT | TAT | GAG | ATC | AAT | AAA | 768 |
| Phe | Thr | Tyr | His | Val 245 | Lys | Asn | Arg | Glu | Gln 250 | Ala | Tyr | Glu | Ile | Asn 255 | Lys | |
| AAA | TCT | GGT | CTG | AAT | GAA | GAA | ATA | AAC | AAC | ACT | GAC | CTG | ATC | TCT | GAG | 816 |
| Lys | Ser | Gly | Leu 260 | Asn | Glu | Glu | Ile | Asn 265 | Asn | Thr | Asp | Leu | Ile 270 | Ser | Glu | |
| AAA | TAT | TAC | GTC | CTT | AAA | AAA | GGG | GAA | AAG | CCG | TAT | GAT | CCC | TTT | GAT | 864 |
| Lys | Tyr | Tyr 275 | Val | Leu | Lys | Lys | Gly 280 | Glu | Lys | Pro | Tyr | Asp 285 | Pro | Phe | Asp | |
| CGC | AGT | CAC | TTG | AAA | CTG | TTC | ACC | ATC | AAA | TAC | GTT | GAT | GTC | AAC | ACC | 912 |
| Arg | Ser | His 290 | Leu | Lys | Leu | Phe | Thr 295 | Ile | Lys | Tyr | Val | Asp 300 | Val | Asn | Thr | |
| AAC | GAA | TTG | CTA | AAA | AGC | GAG | CAG | CTC | TTA | ACA | GCT | AGC | GAA | CGT | AAC | 960 |
| Asn 305 | Glu | Leu | Leu | Lys | Ser 310 | Glu | Gln | Leu | Leu | Thr 315 | Ala | Ser | Glu | Arg | Asn 320 | |
| TTA | GAC | TTC | AGA | GAT | TTA | TAC | GAT | CCT | CGT | GAT | AAG | GCT | AAA | CTA | CTC | 1008 |
| Leu | Asp | Phe | Arg | Asp 325 | Leu | Tyr | Asp | Pro | Arg 330 | Asp | Lys | Ala | Lys | Leu 335 | Leu | |
| TAC | AAC | AAT | CTC | GAT | GCT | TTT | GGT | ATT | ATG | GAC | TAT | ACC | TTA | ACT | GGA | 1056 |
| Tyr | Asn | Asn | Leu 340 | Asp | Ala | Phe | Gly | Ile 345 | Met | Asp | Tyr | Thr | Leu 350 | Thr | Gly | |
| AAA | GTA | GAA | GAT | AAT | CAC | GAT | GAC | ACC | AAC | CGT | ATC | ATA | ACC | GTT | TAT | 1104 |
| Lys | Val | Glu | Asp 355 | Asn | His | Asp | Asp | Thr 360 | Asn | Arg | Ile | Ile | Thr 365 | Val | Tyr | |
| ATG | GGC | AAG | CGA | CCC | GAA | GGA | GAG | AAT | GCT | AGC | TAT | CAT | TTA | GCC | TAT | 1152 |
| Met | Gly 370 | Lys | Arg | Pro | Glu | Gly 375 | Glu | Asn | Ala | Ser | Tyr 380 | His | Leu | Ala | Tyr | |
| GAT | AAA | GAT | CGT | TAT | ACC | GAA | GAA | GAA | CGA | GAA | GTT | TAC | AGC | TAC | CTG | 1200 |
| Asp 385 | Lys | Asp | Arg | Tyr | Thr 390 | Glu | Glu | Glu | Arg | Glu 395 | Val | Tyr | Ser | Tyr | Leu 400 | |
| CGT | TAT | ACA | GGG | ACA | CCT | ATA | CCT | GAT | AAC | CCT | AAC | GAC | AAA | ATC | GAA | 1248 |
| Arg | Tyr | Thr | Gly | Thr 405 | Pro | Ile | Pro | Asp | Asn 410 | Pro | Asn | Asp | Lys | Ile 415 | Glu | |
| GGT | AGA | GTT | GTT | TAC | ACC | GAC | TGT | ACT | GAA | TCC | GGA | CAA | AAC | CTG | TGT | 1296 |
| Gly | Arg | Val | Val 420 | Tyr | Thr | Asp | Cys | Thr 425 | Glu | Ser | Gly | Gln | Asn 430 | Leu | Cys | |
| TTG | TGT | GAG | GGT | TCT | AAC | GTC | TGT | GGT | CAG | GGT | AAC | AAA | TGC | ATC | CTG | 1344 |
| Leu | Cys | Glu 435 | Gly | Ser | Asn | Val | Cys 440 | Gly | Gln | Gly | Asn | Lys 445 | Cys | Ile | Leu | |
| GGT | TCC | GAC | GGT | GAA | AAG | AAC | CAA | TGT | GTC | ACT | GGT | GAA | GGT | ACC | CCA | 1392 |
| Gly | Ser | Asp 450 | Gly | Glu | Lys | Asn | Gln 455 | Cys | Val | Thr | Gly | Glu 460 | Gly | Thr | Pro | |
| AAG | CCG | CAG | TCC | CAC | AAC | GAT | GGA | GAT | TTC | GAA | GAA | ATC | CCA | GAA | GAA | 1440 |
| Lys | Pro | Gln | Ser | His 470 | Asn | Asp | Gly | Asp | Phe 475 | Glu | Glu | Ile | Pro | Glu 480 | Glu | |
| TAT | CTG | CAG | TAATAGGGAT | CCGAATTC | | | | | | | | | | | | 1467 |
| Tyr | Leu | Gln | | | | | | | | | | | | | | |

(2) INFORMATION FOR SEQ ID NO:47:

(i) SEQUENCE CHARACTERISTICS:
    (A) LENGTH: 483 amino acids
    (B) TYPE: amino acid -continued ( D ) TOPOLOGY: linear ( i i ) MOLECULE TYPE: protein ( x i ) SEQUENCE DESCRIPTION: SEQ ID NO:47:

```
Ile Ala Gly Pro Glu Trp Leu Leu Asp Arg Pro Ser Val Asn Asn Ser
 1               5                  10                  15

Gln Leu Val Val Ser Val Ala Gly Thr Val Glu Gly Thr Asn Gln Asp
            20                  25                  30

Ile Ser Leu Lys Phe Phe Glu Ile Asp Leu Thr Ser Arg Pro Ala His
            35                  40                  45

Gly Gly Lys Thr Glu Gln Gly Leu Ser Pro Lys Ser Lys Pro Phe Ala
        50                  55                  60

Thr Asp Ser Gly Ala Met Pro His Lys Leu Glu Lys Ala Asp Leu Leu
 65                  70                  75                  80

Lys Ala Ile Gln Glu Gln Leu Ile Ala Asn Val His Ser Asn Asp Asp
                85                  90                  95

Tyr Phe Glu Val Ile Asp Phe Ala Ser Asp Ala Thr Ile Thr Asp Arg
               100                 105                 110

Asn Gly Lys Val Tyr Phe Ala Asp Lys Asp Gly Ser Val Thr Leu Pro
           115                 120                 125

Thr Gln Pro Val Gln Glu Phe Leu Leu Ser Gly His Val Arg Val Arg
       130                 135                 140

Pro Tyr Lys Glu Lys Pro Ile Gln Asn Gln Ala Lys Ser Val Asp Val
145                 150                 155                 160

Glu Tyr Thr Val Gln Phe Thr Pro Leu Asn Pro Asp Asp Asp Phe Arg
               165                 170                 175

Pro Gly Leu Lys Asp Thr Lys Leu Leu Lys Thr Leu Ala Ile Gly Asp
           180                 185                 190

Thr Ile Thr Ser Gln Glu Leu Leu Ala Gln Ala Gln Ser Ile Leu Asn
       195                 200                 205

Lys Thr His Pro Gly Tyr Thr Ile Tyr Glu Arg Asp Ser Ser Ile Val
210                 215                 220

Thr His Asp Asn Asp Ile Phe Arg Thr Ile Leu Pro Met Asp Gln Glu
225                 230                 235                 240

Phe Thr Tyr His Val Lys Asn Arg Glu Gln Ala Tyr Glu Ile Asn Lys
               245                 250                 255

Lys Ser Gly Leu Asn Glu Glu Ile Asn Asn Thr Asp Leu Ile Ser Glu
           260                 265                 270

Lys Tyr Tyr Val Leu Lys Lys Gly Glu Lys Pro Tyr Asp Pro Phe Asp
       275                 280                 285

Arg Ser His Leu Lys Leu Phe Thr Ile Lys Tyr Val Asp Val Asn Thr
290                 295                 300

Asn Glu Leu Leu Lys Ser Glu Gln Leu Leu Thr Ala Ser Glu Arg Asn
305                 310                 315                 320

Leu Asp Phe Arg Asp Leu Tyr Asp Pro Arg Asp Lys Ala Lys Leu Leu
               325                 330                 335

Tyr Asn Asn Leu Asp Ala Phe Gly Ile Met Asp Tyr Thr Leu Thr Gly
           340                 345                 350

Lys Val Glu Asp Asn His Asp Asp Thr Asn Arg Ile Ile Thr Val Tyr
       355                 360                 365

Met Gly Lys Arg Pro Glu Gly Glu Asn Ala Ser Tyr His Leu Ala Tyr
       370                 375                 380

Asp Lys Asp Arg Tyr Thr Glu Glu Glu Arg Glu Val Tyr Ser Tyr Leu
385                 390                 395                 400

Arg Tyr Thr Gly Thr Pro Ile Pro Asp Asn Pro Asn Asp Lys Ile Glu
```

|     |     |     |     |     |     |     | 405 |     |     |     |     |     | 410 |     |     |     |     |     | 415 |
| --- | --- | --- | --- | --- | --- | --- | --- | --- | --- | --- | --- | --- | --- | --- | --- | --- | --- | --- | --- |

Gly Arg Val Val Tyr Thr Asp Cys Thr Glu Ser Gly Gln Asn Leu Cys
            420                     425                 430

Leu Cys Glu Gly Ser Asn Val Cys Gly Gln Gly Asn Lys Cys Ile Leu
        435                 440                 445

Gly Ser Asp Gly Glu Lys Asn Gln Cys Val Thr Gly Glu Gly Thr Pro
    450             455                 460

Lys Pro Gln Ser His Asn Asp Gly Asp Phe Glu Glu Ile Pro Glu Glu
465             470             475                         480

Tyr Leu Gln ( 2 ) INFORMATION FOR SEQ ID NO:48:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..47
        ( D ) OTHER INFORMATION: /note="oligonucleotide BB3318"

( x i ) SEQUENCE DESCRIPTION: SEQ ID NO:48:

TCGGTGTAAA CAACTCTTCT ACCTTCGATT TTGTCGTTAG GGTTATC    47

( 2 ) INFORMATION FOR SEQ ID NO:49:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..21
        ( D ) OTHER INFORMATION: /note="oligonucleotide BB3623"

( x i ) SEQUENCE DESCRIPTION: SEQ ID NO:49:

GTGTAAACAA CTCTACCTTC G    21

( 2 ) INFORMATION FOR SEQ ID NO:50:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..41
        ( D ) OTHER INFORMATION: /note="oligonucleotide BB2011"

( x i ) SEQUENCE DESCRIPTION: SEQ ID NO:50:

AGCTTACCTG CCATGGTTGT TTACACCGAC TGTACTGAAT C    41

( 2 ) INFORMATION FOR SEQ ID NO:51:

( i ) SEQUENCE CHARACTERISTICS:
        ( A ) LENGTH: 44 base pairs
        ( B ) TYPE: nucleic acid ( C ) STRANDEDNESS: single
( D ) TOPOLOGY: linear ( i i ) MOLECULE TYPE: cDNA ( i x ) FEATURE:
( A ) NAME/KEY: misc_feature
( B ) LOCATION: 1..44
( D ) OTHER INFORMATION: /note="oligonucleotide BB2012"

( x i ) SEQUENCE DESCRIPTION: SEQ ID NO:51:

TTGTCCGGAT TCAGTACAGT CGGTGTAAAC AACCATGGCA GGTA 44

( 2 ) INFORMATION FOR SEQ ID NO:52:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: misc_feature
( B ) LOCATION: 1..37
( D ) OTHER INFORMATION: /note="oligonucleotide BB2013"

( x i ) SEQUENCE DESCRIPTION: SEQ ID NO:52:

CGGACAAAAC CTGTGTTTGT GTGAGGGTTC TAACGTC 37

( 2 ) INFORMATION FOR SEQ ID NO:53:

( i ) SEQUENCE CHARACTERISTICS:
( A ) LENGTH: 37 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: misc_feature
( B ) LOCATION: 1..37
( D ) OTHER INFORMATION: /note="oligonucleotide BB2014"

( x i ) SEQUENCE DESCRIPTION: SEQ ID NO:53:

GACCACAGAC GTTAGAACCC TCACACAAAC ACAGGTT 37

( 2 ) INFORMATION FOR SEQ ID NO:54:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: misc_feature
( B ) LOCATION: 1..40
( D ) OTHER INFORMATION: /note="oligonucleotide BB2015"

( x i ) SEQUENCE DESCRIPTION: SEQ ID NO:54:

TGTGGTCAGG GTAACAAATG CATCCTGGGT TCCGACGGTG 40

( 2 ) INFORMATION FOR SEQ ID NO:55:

( i ) SEQUENCE CHARACTERISTICS:
( A ) LENGTH: 40 base pairs
( B ) TYPE: nucleic acid
( C ) STRANDEDNESS: single
( D ) TOPOLOGY: linear ( i i ) MOLECULE TYPE: cDNA ( i x ) FEATURE:
    ( A ) NAME/KEY: misc_feature
    ( B ) LOCATION: 1..40
    ( D ) OTHER INFORMATION: /note="oligonucleotide BB2016"

( x i ) SEQUENCE DESCRIPTION: SEQ ID NO:55:

TTCTTTTCAC CGTCGGAACC CAGGATGCAT TTGTTACCCT     40

( 2 ) INFORMATION FOR SEQ ID NO:56:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..35
        ( D ) OTHER INFORMATION: /note="oligonucleotide BB2017"

( x i ) SEQUENCE DESCRIPTION: SEQ ID NO:56:

AAAAGAACCA ATGTGTCACT GGTGAAGGTA CCCCA     35

( 2 ) INFORMATION FOR SEQ ID NO:57:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..35
        ( D ) OTHER INFORMATION: /note="oligonucleotide BB2018"

( x i ) SEQUENCE DESCRIPTION: SEQ ID NO:57:

GCGGCTTTGG GGTACCTTCA CCAGTGACAC ATTGG     35

( 2 ) INFORMATION FOR SEQ ID NO:58:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..39
        ( D ) OTHER INFORMATION: /note="oligonucleotide BB2019"

( x i ) SEQUENCE DESCRIPTION: SEQ ID NO:58:

AAGCCGCAGT CCCACAACGA TGGAGATTTC GAAGAAATC     39

( 2 ) INFORMATION FOR SEQ ID NO:59:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
  ( A ) NAME/KEY: misc_feature
  ( B ) LOCATION: 1..39
  ( D ) OTHER INFORMATION: /note="oligonucleotide BB2020"

( x i ) SEQUENCE DESCRIPTION: SEQ ID NO:59:

CTTCTGGGAT TTCTTCGAAA TCTCCATCGT TGTGGGACT 39

( 2 ) INFORMATION FOR SEQ ID NO:60:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_feature
    ( B ) LOCATION: 1..31
    ( D ) OTHER INFORMATION: /note="oligonucleotide BB2021"

( x i ) SEQUENCE DESCRIPTION: SEQ ID NO:60:

CCAGAAGAAT ATCTGCAGTA ATAGGGATCC G 31

( 2 ) INFORMATION FOR SEQ ID NO:61:

( i ) SEQUENCE CHARACTERISTICS:
    ( A ) LENGTH: 28 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_feature
    ( B ) LOCATION: 1..28
    ( D ) OTHER INFORMATION: /note="oligonucleotide BB2022"

( x i ) SEQUENCE DESCRIPTION: SEQ ID NO:61:

AATTCGGATC CCTATTACTG CAGATATT 28

( 2 ) INFORMATION FOR SEQ ID NO:62:

( i ) SEQUENCE CHARACTERISTICS:
    ( A ) LENGTH: 16 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_feature
    ( B ) LOCATION: 1..16
    ( D ) OTHER INFORMATION: /note="oligonucleotide BB2136"

( x i ) SEQUENCE DESCRIPTION: SEQ ID NO:62:

TGGTCTAACG CGCACT 16

( 2 ) INFORMATION FOR SEQ ID NO:63:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:

( A ) NAME/KEY: misc_feature
            ( B ) LOCATION: 1..17
            ( D ) OTHER INFORMATION: /note="oligonucleotide BB3509"

( x i ) SEQUENCE DESCRIPTION: SEQ ID NO:63:

GAGTAAACTG TACAGTA                                                               17

( 2 ) INFORMATION FOR SEQ ID NO:64:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: cDNA ( i x ) FEATURE:
            ( A ) NAME/KEY: misc_feature
            ( B ) LOCATION: 1..17
            ( D ) OTHER INFORMATION: /note="oligonucleotide BB3508"

( x i ) SEQUENCE DESCRIPTION: SEQ ID NO:64:

GATCTCATAA GCTTGTT                                                               17

( 2 ) INFORMATION FOR SEQ ID NO:65:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: cDNA ( i x ) FEATURE:
            ( A ) NAME/KEY: misc_feature
            ( B ) LOCATION: 1..17
            ( D ) OTHER INFORMATION: /note="oligonucleotide BB2135"

( x i ) SEQUENCE DESCRIPTION: SEQ ID NO:65:

TTTAGCCTTA TCACGAG                                                               17

( 2 ) INFORMATION FOR SEQ ID NO:66:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: cDNA ( i x ) FEATURE:
            ( A ) NAME/KEY: misc_feature
            ( B ) LOCATION: 1..17
            ( D ) OTHER INFORMATION: /note="oligonucleotide BB3718"

( x i ) SEQUENCE DESCRIPTION: SEQ ID NO:66:

CGTTGATGTC AACACCA                                                               17

( 2 ) INFORMATION FOR SEQ ID NO:67:

( i ) SEQUENCE CHARACTERISTICS:
            ( A ) LENGTH: 17 base pairs
            ( B ) TYPE: nucleic acid
            ( C ) STRANDEDNESS: single
            ( D ) TOPOLOGY: linear ( i i ) MOLECULE TYPE: cDNA ( i x ) FEATURE:
            ( A ) NAME/KEY: misc_feature
            ( B ) LOCATION: 1..17

(D) OTHER INFORMATION: /note="oligonucleotide BB2755"

(xi) SEQUENCE DESCRIPTION: SEQ ID NO:67:

GACGACTACT TTGAGGT 17

(2) INFORMATION FOR SEQ ID NO:68:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..17
        (D) OTHER INFORMATION: /note="oligonucleotide BB2134"

(xi) SEQUENCE DESCRIPTION: SEQ ID NO:68:

CCCAACCTGT CCAAGAA 17

(2) INFORMATION FOR SEQ ID NO:69:

(i) SEQUENCE CHARACTERISTICS:
        (A) LENGTH: 10 amino acids
        (B) TYPE: amino acid
        (D) TOPOLOGY: linear (ii) MOLECULE TYPE: protein (ix) FEATURE:
        (A) NAME/KEY: misc_feature
        (B) LOCATION: 1..10
        (D) OTHER INFORMATION: /note="thrombin cleavable linker"

(xi) SEQUENCE DESCRIPTION: SEQ ID NO:69:

Val Glu Leu Gln Gly Val Val Pro Arg Gly 10
 1              5                10

(2) INFORMATION FOR SEQ ID NO:70:

(i) SEQUENCE CHARACTERISTICS:
        (A) LENGTH: 5 amino acids
        (B) TYPE: amino acid
        (D) TOPOLOGY: linear (ii) MOLECULE TYPE: protein (ix) FEATURE:
        (A) NAME/KEY: misc_feature
        (B) LOCATION: 1..5
        (D) OTHER INFORMATION: /note="N-terminal amino acids of
                native hirudin"

(xi) SEQUENCE DESCRIPTION: SEQ ID NO:70:

Val Val Tyr Thr Asp 5
 1              5

(2) INFORMATION FOR SEQ ID NO:71:

(i) SEQUENCE CHARACTERISTICS:
        (A) LENGTH: 4 amino acids
        (B) TYPE: amino acid
        (D) TOPOLOGY: linear (ii) MOLECULE TYPE: protein (ix) FEATURE:
        (A) NAME/KEY: misc_feature
        (B) LOCATION: 1..4
        (D) OTHER INFORMATION: /note="Factor Xa cleavable
                linker"

( x i ) SEQUENCE DESCRIPTION: SEQ ID NO:71:

Ile Glu Gly Arg
1                                                                                                4

( 2 ) INFORMATION FOR SEQ ID NO:72:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( i x ) FEATURE:
        ( A ) NAME/KEY: misc_feature
        ( B ) LOCATION: 1..2
        ( D ) OTHER INFORMATION: /note="each is independently a hydrobphobic residue"

( i x ) FEATURE:
        ( A ) NAME/KEY: misc_feature
        ( B ) LOCATION: 5..6
        ( D ) OTHER INFORMATION: /note="each is independently a non-acidic residue"

( x i ) SEQUENCE DESCRIPTION: SEQ ID NO:72:

Xaa Xaa Pro Arg Xaa Xaa
1                   5                                                                            6

( 2 ) INFORMATION FOR SEQ ID NO:73:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: protein ( i x ) FEATURE:
        ( A ) NAME/KEY: misc_feature
        ( B ) LOCATION: 1..2
        ( D ) OTHER INFORMATION: /note="The first amino acid is a hydrobphobic residue and the second is an acidic residue."

( x i ) SEQUENCE DESCRIPTION: SEQ ID NO:73:

Xaa Xaa Gly Arg
1                                                                                                4